(12) United States Patent
Wang

(10) Patent No.: US 12,156,894 B2
(45) Date of Patent: Dec. 3, 2024

(54) RECOMBINANTLY-MODIFIED ADENO-ASSOCIATED VIRUS (rAAV) HAVING IMPROVED PACKAGING EFFICIENCY

(71) Applicant: CHARLES RIVER LABORATORIES, INC., Wilmington, MA (US)

(72) Inventor: Qizhao Wang, Rockville, MD (US)

(73) Assignee: CHARLES RIVER LABORATORIES, INC., Wilmington, MA (US)

( * ) Notice: Subject to any disclaimer, the term of this patent is extended or adjusted under 35 U.S.C. 154(b) by 394 days.

(21) Appl. No.: 17/627,165

(22) PCT Filed: Mar. 12, 2020

(86) PCT No.: PCT/US2020/022326
§ 371 (c)(1),
(2) Date: Jan. 14, 2022

(87) PCT Pub. No.: WO2021/011034
PCT Pub. Date: Jan. 21, 2021

(65) Prior Publication Data
US 2022/0257678 A1 Aug. 18, 2022

Related U.S. Application Data

(63) Continuation of application No. 16/512,051, filed on Jul. 15, 2019, now Pat. No. 10,653,731.

(51) Int. Cl.
*A61K 35/761* (2015.01)
*C07K 14/075* (2006.01)
*C12N 15/86* (2006.01)

(52) U.S. Cl.
CPC .......... *A61K 35/761* (2013.01); *C07K 14/075* (2013.01); *C12N 15/86* (2013.01); *C12N 2710/10343* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 6,566,118 B1 | 5/2003 | Atkinson et al. |
| 6,723,551 B2 | 4/2004 | Kotin et al. |
| 6,733,757 B2 | 5/2004 | Patel et al. |
| 6,753,419 B1 | 6/2004 | Toniatti et al. |
| 6,759,050 B1 | 7/2004 | Sista et al. |
| 6,764,845 B2 | 7/2004 | Sista et al. |
| 6,821,511 B2 | 11/2004 | Kotin et al. |
| 6,841,357 B1 | 1/2005 | Vaillancourt et al. |
| 6,846,665 B1 | 1/2005 | Borer et al. |
| 6,962,815 B2 | 11/2005 | Bartlett |
| 6,984,517 B1 | 1/2006 | Chiorini et al. |
| 6,989,264 B2 | 1/2006 | Atkinson et al. |
| 6,995,006 B2 | 2/2006 | Atkinson et al. |
| 7,105,345 B2 | 9/2006 | Wilson et al. |
| 7,115,391 B1 | 10/2006 | Chen et al. |
| 7,122,348 B2 | 10/2006 | Wong et al. |
| 7,186,552 B2 | 3/2007 | Wilson et al. |
| 7,208,315 B2 | 4/2007 | Miller et al. |
| 7,271,002 B2 | 9/2007 | Kotin et al. |
| 7,419,817 B2 | 9/2008 | Chiorini et al. |
| 7,439,065 B2 | 10/2008 | Ferrari et al. |
| 7,479,554 B2 | 1/2009 | Chiorini et al. |
| 7,598,070 B2 | 10/2009 | Sista et al. |
| 7,625,570 B1 | 12/2009 | Schaffer et al. |
| 7,906,111 B2 | 3/2011 | Wilson et al. |

(Continued)

FOREIGN PATENT DOCUMENTS

| WO | 2014/143932 A1 | 9/2014 |
| WO | 2017/112948 A1 | 6/2017 |
| WO | 2021/011034 A1 | 1/2021 |

OTHER PUBLICATIONS

Adamson-Small, L et al. (2017) "Sodium Chloride Enhances Recombinant Adeno-Associated Virus Production in a Serum-Free Suspension Manufacturing Platform Using the Herpes Simplex Virus System," Hum. Gene Ther. Meth. 28(1):1-14.
Artusi, S. et al. (2015) "The Herpes Simplex Virus-1 Genome Contains Multiple Clusters of Repeated G-Quadruplex: Implications for the Antiviral Activity of a G-Quadruplex Ligand," Antivir. Res. 118:123-131.
Auricchio, A. et al. (2001) "Isolation of Highly Infectious and Pure Adeno-Associated Virus Type 2 Vectors With a Single-Step Gravity-Flow Column," Hum. Gene Ther. 12:71-76.
Ayuso, E. (2016) "Manufacturing of Recombinant Adeno-Associated Viral Vectors: New Technologies are Welcome," Methods & Clinical Development 3:15049.
Balakrishnan, B. et al. (2014) "Basic Biology of Adeno-Associated Virus (AAV) Vectors Used in Gene Therapy," Curr. Gene Ther. 14(2):86-100.

(Continued)

*Primary Examiner* — Robert M Kelly
(74) *Attorney, Agent, or Firm* — MEDLER FERRO WOODHOUSE & MILLS PLLC

(57) ABSTRACT

The present invention is directed to recombinantly-modified adeno-associated virus (rAAV) having improved packaging efficiency, pharmaceutical compositions comprising such rAAV, and methods for their production and use. The present invention is particularly directed to recombinantly-modified adeno-associated virus (rAAV) that have been further modified to comprise Cis-Elements, including replication origins, promoters and enhancers, that are capable of regulating the replication of an rAAV genome and that improve rAAV replication. Preferably, such Cis-Elements are provided within domains of the rAAV that precede and/or follow the 5' and/or 3' inverted terminal repeated sequences (ITR) of an rAAV. The invention particularly concerns the presence and the use of polynucleotide Cis-Elements that comprise actual or potential G-Quadruplex Sequences, polynucleotide Cis-Elements that comprise DNA sequences from wild-type AAV (wt AAV) and polynucleotide Cis-Elements that comprise DNA sequences from other viral genomes or from the human genome.

17 Claims, 13 Drawing Sheets

Specification includes a Sequence Listing.

(56) References Cited

U.S. PATENT DOCUMENTS

| | | |
|---|---|---|
| 8,163,543 B2 | 4/2012 | Urabe et al. |
| 8,192,975 B2 | 6/2012 | Sista et al. |
| 8,507,267 B2 | 8/2013 | Chiorini et al. |
| 8,697,359 B1 | 4/2014 | Zhang |
| 8,846,389 B2 | 9/2014 | Chiorini et al. |
| 8,852,607 B2 | 10/2014 | Sista et al. |
| 8,945,918 B2 | 2/2015 | Chen |
| 9,193,956 B2 | 11/2015 | Schaffer et al. |
| 9,441,206 B2 | 9/2016 | Grieger et al. |
| 9,441,244 B2 | 9/2016 | Schaffer et al. |
| 9,457,103 B2 | 10/2016 | Schaffer et al. |
| 9,458,517 B2 | 10/2016 | Schaffer et al. |
| 9,598,703 B2 | 3/2017 | Garcia et al. |
| 9,677,089 B2 | 6/2017 | Gao et al. |
| 9,737,618 B2 | 8/2017 | Wilson et al. |
| 9,856,539 B2 | 1/2018 | Schaffer et al. |
| 9,879,279 B2 | 1/2018 | Chen |
| 9,879,282 B2 | 1/2018 | Chen |
| 9,884,071 B2 | 2/2018 | Wilson et al. |
| 10,000,772 B2 | 6/2018 | Doudna et al. |
| 10,017,746 B2 | 7/2018 | Sheldon et al. |
| 10,046,016 B2 | 8/2018 | Schaffer et al. |
| 10,113,167 B2 | 10/2018 | Doudna et al. |
| 10,161,011 B2 | 12/2018 | Akashika et al. |
| 10,202,657 B2 | 2/2019 | Schaffer et al. |
| 10,214,566 B2 | 2/2019 | Schaffer et al. |
| 10,214,730 B2 | 2/2019 | Bahou et al. |
| 10,214,785 B2 | 2/2019 | Schaffer et al. |
| 10,227,611 B2 | 3/2019 | Doudna et al. |
| 10,265,417 B2 | 4/2019 | Wilson et al. |
| 10,266,846 B2 | 4/2019 | Gao et al. |
| 10,294,452 B2 | 5/2019 | He |
| 10,301,650 B2 | 5/2019 | Gao et al. |
| 10,653,731 B1 | 5/2020 | Wang |
| 2005/0266567 A1 | 12/2005 | Atkinson et al. |
| 2006/0205079 A1 | 9/2006 | Lynch et al. |
| 2011/0151434 A1 | 6/2011 | Gao et al. |
| 2011/0207226 A1 | 8/2011 | Ni et al. |
| 2014/0242671 A1 | 8/2014 | Grieger et al. |
| 2019/0211357 A1 | 7/2019 | Arts |

OTHER PUBLICATIONS

Bedrat, A. et al. (2016) "Re-evaluation of G-Quadruplex propensity with G4Hunter," Nucleic Acids Res. 44(4):1746-1759.

Ben-Israel, H. et al. (2002) "Adenovirus and Cell Cycle Control," Front. Biosci. 7:d1369-d1395.

Berns, K. I. et al. (2017) "AAV: An Overview of Unanswered Questions," Human Gene Ther. 28(4):308-313.

Berry, G.E. et al. (2016) "Cellular Transduction Mechanisms of Adeno-Associated Viral Vectors," Curr. Opin. Virol. 21:54-60.

Besnard, E. et al. (2012) "Unraveling Cell Type-Specific and Reprogrammable Human Replication Origin Signatures Associated With G-Quadruplex Consensus Motifs," Nat. Struct. Mol. Biol. 19:837-844.

Blessing, D. et al. (2016) "Adeno-Associated Virus and Lentivirus Vectors: A Refined Toolkit for the Central Nervous System," 21:61-66.

Brument, N. et al. (2002) "A Versatile and Scalable Two-Step Ion-Exchange Chromatography Process for the Purification of Recombinant Adeno-Associated Virus Serotypes-2 and -5," Mol. Ther. 6:678-686.

Buning, H. et al. (2019) "Capsid Modifications for Targeting and Improving the Efficacy of AAV Vectors," Mol. Ther. Meth. Clin. Devel. 12:248-265.

Cao, M. et al. (2014) "The X Gene of Adeno-Associated Virus 2 (AAV2) Is Involved in Viral DNA Replication," PLoS One 9, e104596:1-10.

Chiorini, J.A. et al. (1997) "Cloning of Adeno-Associated Virus Type 4 (AAV4) and Generation of Recombinant AAV4 Particles," J. Virol. 71(9):6823-6833.

Chopra, A. (2007) "Recombinant Adenovirus With Enhanced Green Fluorescent Protein," In: Molecular Imaging and Contrast Agent Database (MICAD) [Internet]. Bethesda (MD): National Center for Biotechnology Information (pp. 1-5).

Cinelli, R.A. et al. (2000) "The Enhanced Green Fluorescent Protein as a Tool for the Analysis of Protein Dynamics and Localization: Local Fluorescence Study at the Single-Molecule Level," Photochem. Photobiol. 71(6):771-776.

Clement, N. et al. (2016) "Manufacturing of Recombinant Adeno-Associated Viral Vectors for Clinical Trials," Meth. Clin. Develop. 3:16002:1-7.

Colella, P. et al. (2018) "Emerging Issues in AAV-Mediated In Vivo Gene Therapy," Molec. Ther. Meth. Clin. Develop. 8:87-104.

Davidoff, A.M. et al. (2004) "Purification of Recombinant Adeno-Associated Virus Type 8 Vectors by Ion Exchange Chromatography Generates Clinical Grade Vector Stock," J. Virol. Methods 121:209-215.

Duan, D. (2016) "Systemic Delivery of Adeno-Associated Viral Vectors," Curr. Opin. Virol. 21:16-25.

During, M.J. et al. (1998) "In Vivo Expression of Therapeutic Human Genes for Dopamine Production in the Caudates of MPTP-Treated Monkeys Using an AAV Vector," Gene The. 5:820-827.

Durocher, Y. et al. (2007) "Scalable Serum-Free Production of Recombinant Adeno-Associated Virus Type 2 by Transfection of 293 Suspension Cells," J. Virol. Meth. 144:32-40.

Eddy, J. et al. (2006) "Gene Function Correlates With Potential for G4 DNA Formation in the Human Genome," Nucleic Acids Res. 34:3887-3896.

Egelie, K.J. et al. (2016) "The Emerging Patent Landscape of CRISPR-Cas Gene Editing Technology," Nature Biotechnol. 34(10):1025-1031.

Ferreira, V. et al. (2014) "Immune Responses to AAV-Vectors, The Glybera Example From Bench to Bedside" Front. Immunol. 5(82):1-15.

Francois, A. et al. (2018) "Accurate Titration of Infectious AAV Particles Requires Measurement of Biologically Active Vector Genomes and Suitable Controls," Molec. Ther. Meth. Clin. Develop. 10:223-236.

Gallo, A. et al. (2012) "Structure of Nucleophosmin DNA-binding Domain and Analysis of Its Complex with a G-Quadruplex Sequence from the c-MYC Promoter," J. Biol. Chem. 287(32):26539-26548.

Gambotto, A. et al. (2000) "Immunogenicity of Enhanced Green Fluorescent Protein (EGFP) in BALB/C Mice: Identification of an H2-Kd-Resfricted CTL Epitope," Gene Ther. 7(23):2036-2040.

Gao, G.P. et al. (2002) "Novel Adeno Associated Viruses From Rhesus Monkeys as Vectors for Human Gene Therapy," Proc. Natl. Acad. Sci. (U.S.A.) 99(18):11854-11859.

Ghosh, A. et al. (2007) "Expanding Adeno-Associated Viral Vector Capacity: A Tale of Two Vectors," Biotechnol. Genet. Eng. Rev. 24:165-177.

Grieger, J.C. et al. (2012) "Adeno-Associated Virus Vectorology, Manufacturing, and Clinical Applications," Meth. Enzymol. 507:229-254.

Grimm, D. et al. (1998) "Novel Tools for Production and Purification of Recombinant Adeno-Associated Virus Vectors," Hum. Gene Ther. 9:2745-2760.

Guggino, W.B. et al. (2017) "AAV Gene Therapy for Cystic Fibrosis: Current Barriers and Recent Developments," Expert Opin Biol Ther. 17(10): 1265-1273.

Harris, L.M. et al. (2015) "G-Quadruplexes in Pathogens: A Common Route to Virulence Control?" PLoS Pathog. 11(2):e1004562.

Hastie, E. et al. (2015) "Adeno-Associated Virus at 50: A Golden Anniversary of Discovery, Research, and Gene Therapy Success—A Personal Perspective," Human Gene Ther. 26:257-265.

Hauck, B. et al. (2003) "Generation and Characterization of Chimeric Recombinant AAV Vectors," Mol. Ther. 7:419-425.

Hocquemiller, M. et al. (2016) "Adeno-Associated Virus-Based Gene Therapy for CNS Diseases," Hum. Gene Ther. 27(7):478-496.

Hoeben, R.C. et al. (2013) "Adenovirus DNA Replication," Cold Spring Barb. Perspect. Biol. 5:a013003.

Huppert, J.L. et al. (2005) "Prevalence of Quadruplexes in the Human Genome," Nucleic Acids Res. 33:2908-29168.

(56) References Cited

OTHER PUBLICATIONS

Huppert, J.L. et al. (2007) "G-Quadruplexes in Promoters Throughout the Human Genome," Nucleic Acids Res. 35:406-413.
Johnson, F.B. et al. (1972) "Immunological Reactivity of Antisera Prepared Against the Sodium Dodecyl Sulfate-Treated Structural Polypeptides of Adenovirus-Associated Virus," J. Virol. 9(6):1017-1026.
Kay, M. et al. (2017) "Future of rAAV Gene Therapy: Platform for RNAi, Gene Editing and Beyond," Human Gene Ther. 28:361-372.
Kotterman, M.A. et al. (2014) "Engineering Adeno-Associated Viruses for Clinical Gene Therapy," Nat. Rev. Genet. 15(7):445-451.
Kwon, I. et al. (2007) "Designer Gene Delivery Vectors: Molecular Engineering and Evolution of Adeno-Associated Viral Vectors for Enhanced Gene Transfer," Pharm. Res. 25(3):489-499.
Lackner, D.F. et al. (2002) "Studies of the Mechanism of Transactivation of the Adeno-Associated Virus p19 Promoter by Rep Protein," J. Virol. 76(16):8225-8235.
Le, H.T. et al. (2005) "Utility of Pegylated Recombinant Adeno-Associated Viruses for Gene Transfer," J. Control. Release 108:161-177.
Lee, G.K. et al. (2005) "PEG Conjugation Moderately Protects Adeno-Associated Viral Vectors Against Antibody Neutralization," Biotechnol. Bioeng. 92:24-34.
Lino, C.A. et al. (2018) "Delivering CRISPR: A Review of the Challenges and Approaches," Drug Deliv. 25(1):1234-1237.
Lisowski, L. et al. (2015) "Adeno-Associated Virus Serotypes for Gene Therapeutics," 24:59-67.
Liu, Q. et al. (2014) "Neutralizing Antibodies Against AAV2, AAV5 and AAV8 in Healthy and HIV-1-Infected Subjects in China: Implications for Gene Therapy Using AAV Vectors," Gene Ther. 21:732-738.
Lock, M. et al. (2010) "Rapid, Simple, and Versatile Manufacturing of Recombinant Adeno-Associated Viral Vectors at Scale," Hum. Gene Ther. 21:1259-1271.
Lopes, J. et al. (2011) "G-Quadruplex-Induced Instability During Leading-Strand Replication," EMBO J. 30:4033-4046.
Lykken, E.A. et al. (2018) "Recent Progress and Considerations for AAV Gene Therapies Targeting the Central Nervous System," J. Neurodevelop. Dis. 10:16:1-10.
Matsushita, T. et al. (1998) "Adeno-Associated Virus Vectors Can be Efficiently Produced Without Helper Virus," Gene Ther. 5:938-945.
McClements, M.E. et a. (2017) "Adeno-associated Virus (AAV) Dual Vector Strategies for Gene Therapy Encoding Large Transgenes," Yale J. Biol. Med. 90:611-623.
Metifiot, M. et al. (2014) "G-Quadruplexes in Viruses: Function and Potential Therapeutic Applications," Nucleic Acids Res. 42(20):12352-12366.
Millevoi, S. et al. (2012) "G-Quadruplexes in RNA Biology," Wiley interdiscip. Rev. RNA 3:495-507.
Monahan, p. E et al. (2000) "AAV Vectors: Is Clinical Success on the Horizon?," Gene Ther. 7:24-30.
Murphy, M. et al. (2007) "Adeno Associated Virus Type 2 p5 Promoter: a Rep-Regulated DNA Switch Element Functioning in Transcription, Replication, and Site-Specific Integration," J. Virol. 81(8):3721-3730.
Nash, K. et al. (2009) "Identification of Cellular Proteins That Interact With the Adeno Associated Virus Rep Protein," J. Virol. 83(1):454-469.
Naso, M.F. et al. (2017) "Adeno-Associated Virus (AAV) as a Vector for Gene Therapy," BioDrugs 31:317-334.
Ni, T.H. et al. (1998) "Cellular Proteins Required for Adeno-Associated Virus DNA Replication in the Absence of Adenovirus Coinfection," J. Virol. 72(4):2777-2787.
Nicolas, A. et al. (2012) "Factors Influencing Helper-Independent Adeno-Associated Virus Replication," Virology 432(1):1-9.
Ogasawara, Y. et al. (1998) "The Use of Heterologous Promoters for Adeno-Associated Virus (AAV) Protein Expression in AAV Vector Production," Microbiol. Immunol. 42(3):177-185.

Paeschke, K. et al. (2011) "DNA Replication Through G-Quadruplex Motifs Is Promoted by the *Saccharomyces cerevisiae* Pif1 DNA Helicase," Cell 145:678-691.
Penaud-Budloo, M. et al. (2018) "Pharmacology of Recombinant Adeno-associated Virus Production," Molec. Ther. Meth. Clin. Develop. 8:166-180.
Piekna-Przybylska, D. et al. (2014) "U3 Region in the HIV-1 Genome Adopts a G-Quadruplex Structure in Its RNA and DNA Sequence," Biochemistry 53(16):2581-2593.
Rabinowitz, I.E. et al. (2004) "Crossdressing the Virion: The Transcapsidation of Adeno-Associated Virus Serotypes Functionally Defines Subgroups," J. Virol. 78:4421-4432.
Rastall, D.P.W. (2017) "Current and Future Treatments for Lysosomal Storage Disorders," Curr. Treat Options Neurol. 19(12):45.
Salganik, M. et al. (2015) "Adeno-Associated Virus As a Mammalian DNA Vector," Microbiol. Spectr. 3(4):1-32.
Santiago-Ortiz, J.L. (2016) "Adeno-Associated Virus (AAV) Vectors in Cancer Gene Therapy," J. Control Release 240:287-301.
Satkunanathan, S. et al. (2017) "The Function of DNA Binding Protein Nucleophosmin in AAV Replication," Virol. 510:46-54.
Siddiqui-Jain, A. et al. (2002) "Direct Evidence for a G-Quadruplex in a Promoter Region and Its Targeting With a Small Molecule to Repress c-MYC Transcription," Proc. Natl. Acad. Sci. (U.S.A.) 99:11593-11598.
Smith, J.K. et al. (2018) "Creating an Arsenal of Adeno-Associated Virus (AAV) Gene Delivery Stealth Vehicles," PLoS Pathog. 14(5):1-6.
Smith, R.H. et al. (2009) "A Simplified Baculovirus-AAV Expression Vector System Coupled With One-Step Affinity Purification Yields High-Titer rAAV Stocks From Insect Cells," Mol. Ther. 17:1888-1896.
Tlučková, K. et al. (2013) "Human Papillomavirus G-Quadruplexes," Biochemistry 52(41):7207-7216.
Tsien, R.Y. (1998) "The Green Fluorescent Protein," Annu. Rev. Biochem. 67:509-544.
Valton, A.L. et al. (2014) "G4 Motifs Affect Origin Positioning and Efficiency in Two Vertebrate Replicators," EMBO J. 33:732-746.
Van Vliet K.M. et al. (2008) The Role of the Adeno-Associated Virus Capsid in Gene Transfer. In: Drug Delivery Systems, Jain, K.K. (eds.), Meth. Molec. Biol. 437:51-91.
Vandamme, C. et al. (2017) "Unraveling the Complex Story of Immune Responses to AAV Vectors Trial After Trial," Hum. Gene. Ther. 28(11):1061-1074.
Verma, A. et al. (2008) "Genome-Wide Computational and Expression Analyses Reveal G-Quadruplex DNA Motifs as Conserved Cis-Regulatory Elements in Human and Related Species," J. Med. Chem. 51:5641-5649.
Weitzman, M.D. (2005) "Functions of the Adenovirus E4 Proteins and Their Impact on Viral Vectors," Front. Biosci. 10:1106-1117.
Weitzman, M.D. (2006) "The Parvovirus Life Cycle: An Introduction to Molecular Interactions Important for Infection," In: Kerr, J.R. et al. (Eds.) Parvoviruses, Hodder Arnold, London, UK (pp. 143-156).
Wieland, M. et al. (2007) "RNA Quadruplex-Based Modulation of Gene Expression," Chem. Biol., 14:757-763.
Wu, Z. et al. (2010) "Effect of Genome Size on AAV Vector Packaging," Molec. Ther. 18:80-86.
Yao, T. et al. (2017) "Animal-Cell Culture Media: History, Characteristics, and Current Issues," Reproduc. Med. Biol. 16(2):99-117.
Zen, Z. et al. (2004) "Infectious Titer Assay for Adeno-Associated Virus Vectors With Sensitivity Sufficient to Detect Single Infectious Events," Hum. Gene Ther. 15:709-715.
Zinn, E. et al. (2014) "Adeno-Associated Virus: Fit to Serve," Curr. Opin. Virol. 0:90-97.
Zolotukhin, S. et al. (1999) "Recombinant Adeno-Associated Virus Purification Using Novel Methods Improves Infectious Titer and Yield," Gene Ther. 6:973-985.
Zolotukhin, S. et al. (2002) "Production and Purification of Serotype 1, 2, and 5 Recombinant Adeno-Associated Viral Vectors," Methods 28:158-167.
International Search Report issued in PCT/US20/22326, dated Jun. 17, 2020.

(56) References Cited

OTHER PUBLICATIONS

Conway et al. (1999) "High-titer recombinant adeno-associated virus production utilizing a recombinant herpes simplex virus type I vector expressing AAV-2 Rep and Cap," Gene Therapy 6(6):986-993.

Xu, Z.X. et al. (2009) "A 16-bp RBE element mediated Rep-dependent site-specific integration in AAVS1 transgenic mice for expression of hFIX," Gene Therapy 16(5):589-595.

Non-final Office Action issued in U.S. Appl. No. 16/512,051, dated Nov. 29, 2019.

Notice of Allowance issued in U.S. Appl. No. 16/512,051, dated Jan. 23, 2020.

Corrected Notice of Allowance issued in U.S. Appl. No. 16/512,051, dated Mar. 24, 2020.

Chen, "Adeno-associated virus vectors for human gene therapy," World Journal of Medical Genetics 5(3):28-45 (2015).

Thomas et al., "Scalable Recombinant Adeno-Associated Virus Production Using Recombinant Herpes Simplex Virus Type 1 Coinfection of Suspension-Adapted Mammalian Cells," Human Gene Therapy 20(8):861-870 (2009).

Rhodes et al., "G-quadruplexes and their regulatory roles in biology," Nucleic Acids Res. 43(18):8627-8637 (2015).

Satkunanathan et al., "The function of DNA binding protein nucleophosmin in AAV replication," Virology 510:46-54 (2017).

SEQUENCE LISTING

```
<160> NUMBER OF SEQ ID NOS: 74

<210> SEQ ID NO 1
<211> LENGTH: 7415
<212> TYPE: DNA
<213> ORGANISM: Artificial Sequence
<220> FEATURE:
<223> OTHER INFORMATION: Coding Strand of Plasmid pAAV-RC2

<400> SEQUENCE: 1
ccgggccccc cctcgaggtc gacggtatcg ggggagctcg cagggtctcc attttgaagc      60
gggaggtttg aacgcgcagc cgccatgccg gggttttacg agattgtgat taaggtcccc     120
```

```
agcgaccttg acgagcatct gcccggcatt tctgacagct ttgtgaactg ggtggccgag      180
aaggaatggg agttgccgcc agattctgac atggatctga atctgattga gcaggcaccc      240
ctgaccgtgg ccgagaagct gcagcgcgac tttctgacgg aatggcgccg tgtgagtaag      300
gccccggagg ctcttttctt tgtgcaattt gagaagggag agagctactt ccacatgcac      360
gtgctcgtgg aaaccaccgg ggtgaaatcc atggttttgg gacgtttcct gagtcagatt      420
cgcgaaaaac tgattcagag aatttaccgc gggatcgagc cgactttgcc aaactggttc      480
gcggtcacaa agaccagaaa tggcgccgga ggcgggaaca aggtggtgga tgagtgctac      540
atccccaatt acttgctccc caaaacccag cctgagctcc agtgggcgtg gactaatatg      600
gaacagtatt taagcgcctg tttgaatctc acggagcgta aacggttggt ggcgcagcat      660
ctgacgcacg tgtcgcagac gcaggagcag aacaaagaga atcagaatcc caattctgat      720
gcgccggtga tcagatcaaa aacttcagcc aggtacatgg agctggtcgg gtggctcgtg      780
gacaagggga ttacctcgga gaagcagtgg atccaggagg accaggcctc atacatctcc      840
ttcaatgcgg cctccaactc gcggtcccaa atcaaggctg ccttggacaa tgcgggaaag      900
attatgagcc tgactaaaac cgcccccgac tacctggtgg gccagcagcc cgtggaggac      960
atttccagca atcggattta taaaattttg gaactaaacg ggtacgatcc ccaatatgcg     1020
gcttccgtct ttctgggatg ggccacgaaa aagttcggca agaggaacac catctggctg     1080
tttgggcctg caactaccgg gaagaccaac atcgcggagg ccatagccca cactgtgccc     1140
ttctacgggt gcgtaaactg gaccaatgag aactttccct tcaacgactg tgtcgacaag     1200
atggtgatct ggtgggagga ggggaagatg accgccaagg tcgtggagtc ggccaaagcc     1260
attctcggag gaagcaaggt gcgcgtggac cagaaatgca agtcctcggc ccagatagac     1320
ccgactcccg tgatcgtcac ctccaacacc aacatgtgcg ccgtgattga cgggaactca     1380
acgaccttcg aacaccagca gccgttgcaa gaccggatgt tcaaatttga actcacccgc     1440
cgtctggatc atgactttgg gaaggtcacc aagcaggaag tcaaagactt tttccggtgg     1500
gcaaaggatc acgtggttga ggtggagcat gaattctacg tcaaaaaggg tggagccaag     1560
aaaagacccg cccccagtga cgcagatata agtgagccca acgggtgcg cgagtcagtt     1620 gcgcagccat cgacgtcaga cgcggaagct tcgatcaact acgcagacag gtaccaaaac     1680
aaatgttctc gtcacgtggg catgaatctg atgctgtttc cctgcagaca atgcgagaga     1740
atgaatcaga attcaaatat ctgcttcact cacggacaga aagactgttt agagtgcttt     1800
cccgtgtcag aatctcaacc cgtttctgtc gtcaaaaagg cgtatcagaa actgtgctac     1860
attcatcata tcatgggaaa ggtgccagac gcttgcactg cctgcgatct ggtcaatgtg     1920
gatttggatg actgcatctt tgaacaataa atgatttaaa tcaggtatgg ctgccgatgg     1980
ttatcttcca gattggctcg aggacactct ctctgaagga ataagacagt ggtggaagct     2040
caaacctggc ccaccaccac caaagcccgc agagcggcat aaggacgaca gcagggggtct     2100 tgtgcttcct gggtacaagt acctcggacc cttcaacgga ctcgacaagg gagagccggt     2160
caacgaggca gacgccgcgg ccctcgagca cgacaaagcc tacgaccggc agctcgacag     2220
cggagacaac ccgtacctca gtacaacca cgccgacgcg gagtttcagg agcgccttaa     2280
agaagatacg tcttttgggg gcaacctcgg acagcagtc ttccaggcga aaaagagggt     2340
tcttgaacct ctgggcctgg ttgaggaacc tgttaagacg gctccgggaa aaaagaggcc     2400
ggtagagcac tctcctgtgg agccagactc ctcctcggga accggaaagg cgggccagca     2460
gcctgcaaga aaaagattga attttggtca gactggagac gcagactcag tacctgaccc     2520
```

```
ccagcctctc ggacagccac cagcagcccc ctctggtctg ggaactaata cgatggctac   2580
aggcagtggc gcaccaatgg cagacaataa cgagggcgcc gacggagtgg gtaattcctc   2640
gggaaattgg cattgcgatt ccacatggat gggcgacaga gtcatcacca ccagcacccg   2700
aacctgggcc ctgccacct acaacaacca cctctacaaa caaatttcca gccaatcagg    2760
agcctcgaac gacaatcact actttggcta cagcacccct tgggggtatt ttgacttcaa   2820
cagattccac tgccactttt caccacgtga ctggcaaaga ctcatcaaca caactgggg    2880 attccgaccc aagagactca acttcaagct ctttaacatt caagtcaaag aggtcacgca   2940
gaatgacggt acgacgacga ttgccaataa ccttaccagc acggttcagg tgtttactga   3000
ctcggagtac cagctcccgt acgtcctcgg ctcggcgcat caaggatgcc tcccgccgtt   3060
cccagcagac gtcttcatgg tgccacagta tggatacctc accctgaaca acggagtca   3120 ggcagtagga cgctcttcat tttactgcct ggagtacttt ccttctcaga tgctgcgtac   3180
cggaaacaac tttaccttca gctacacttt tgaggacgtt cctttccaca gcagctacgc   3240
tcacagccag agtctggacc gtctcatgaa tcctctcatc gaccagtacc tgtattactt   3300
gagcagaaca aacactccaa gtggaaccac cacgcagtca aggcttcagt tttctcaggc   3360
cggagcgagt gacattcggg accagtctag gaactggctt cctggaccct gttaccgcca   3420
gcagcgagta tcaaagacat ctgcggataa caacaacagt gaatactcgt ggactggagc   3480
taccaagtac cacctcaatg gcagagactc tctggtgaat ccgggcccgg ccatggcaag   3540
ccacaaggac gatgaagaaa agttttttcc tcagagcggg gttctcatct ttgggaagca   3600
aggctcagag aaaacaaatg tggacattga aaggtcatg attacagacg aagaggaaat    3660
caggacaacc aatcccgtgg ctacggagca gtatggttct gtatctacca acctccagag   3720
aggcaacaga caagcagcta ccgcagatgt caacacacaa ggcgttcttc caggcatggt   3780
ctggcaggac agagatgtgt accttcaggg gcccatctgg gcaaagatte cacacacgga   3840 cggacatttt caccccctct ccctcatggg tggattcgga cttaaacacc tcctccaca    3900 gattctcatc aagaacaccc cggtacctgc gaatccttcg accaccttca gtgcggcaaa   3960
gtttgcttcc ttcatcacac agtactccac gggacaggtc agcgtggaga tcgagtggga   4020
gctgcagaag gaaaacagca aacgctggaa tcccgaaatt cagtacactt ccaactacaa   4080
caagtctgtt aatgtggact ttactgtgga cactaatggc gtgtattcag agcctcgccc   4140
cattggcacc agatacctga ctcgtaatct gtaattgctt gttaatcaat aaaccgttta   4200
attcgtttca gttgaacttt ggtctctgcg tatttctttc ttatctagtt tccatgctct   4260
aggatccact agtaacggcc gccagtgtgc tggaattcgg ctttgtagtt aatgattaac   4320
ccgccatgct acttatctac gtagccatgc tctagaggtc ctgtattaga ggtcacgtga   4380
gtgttttgcg acattttgcg acaccatgtg gtcacgctgg gtatttaagc ccgagtgagc   4440
acgcagggtc tccattttga agcgggaggt ttgaacgcgc agccgccaag ccgaattctg   4500
cagatatcca aacactggcg gccgctcgac tagagcggcc gccaccgcgg tggagctcca   4560
gcttttgttc cctttagtga gggttaattg cgcgcttggc gtaatcatgg tcatagctgt   4620
ttcctgtgtg aaattgttat ccgctcacaa ttccacacaa catacgagcc ggaagcataa   4680
agtgtaaagc ctggggtgcc taatgagtga gctaactcac attaattgcg ttgcgctcac   4740
tgcccgcttt ccagtcggga aacctgtcgt gccagctgca ttaatgaatc ggccaacgcg   4800
cggggagagg cggtttgcgt attgggcgct cttccgcttc ctcgctcact gactcgctgc   4860
```

```
gctcggtcgt tcggctgcgg cgagcggtat cagctcactc aaaggcggta atacggttat    4920
ccacagaatc aggggataac gcaggaaaga acatgtgagc aaaaggccag caaaaggcca    4980
ggaaccgtaa aaaggccgcg ttgctggcgt ttttccatag gctccgcccc cctgacgagc    5040
atcacaaaaa tcgacgctca agtcagaggt ggcgaaaccc gacaggacta taaagatacc    5100
aggcgtttcc ccctggaagc tccctcgtgc gctctcctgt tccgaccctg ccgcttaccg    5160
gatacctgtc cgcctttctc ccttcgggaa gcgtggcgct ttctcatagc tcacgctgta    5220
ggtatctcag ttcggtgtag gtcgttcgct ccaagctggg ctgtgtgcac gaaccccccg    5280
ttcagcccga ccgctgcgcc ttatccggta actatcgtct tgagtccaac ccggtaagac    5340
acgacttatc gccactggca gcagccactg gtaacaggat tagcagagcg aggtatgtag    5400
gcggtgctac agagttcttg aagtggtggc ctaactacgg ctacactaga agaacagtat    5460
ttggtatctg cgctctgctg aagccagtta ccttcggaaa aagagttggt agctcttgat    5520
ccggcaaaca aaccaccgct ggtagcggtg gttttttgt ttgcaagcag cagattacgc    5580
gcagaaaaaa aggatctcaa gaagatcctt tgatcttttc tacggggtct gacgctcagt    5640
ggaacgaaaa ctcacgttaa gggattttgg tcatgagatt atcaaaaagg atcttcacct    5700
agatcctttt aaattaaaaa tgaagtttta atcaatcta aagtatatat gagtaaactt    5760
ggtctgacag ttaccaatgc ttaatcagtg aggcacctat ctcagcgatc tgtctatttc    5820
gttcatccat agttgcctga ctccccgtcg tgtagataac tacgatacgg gagggcttac    5880
catctggccc cagtgctgca atgataccgc gagacccacg ctcaccggct ccagatttat    5940
cagcaataaa ccagccagcc ggaagggccg agcgcagaag tggtcctgca actttatccg    6000
cctccatcca gtctattaat tgttgccggg aagctagagt aagtagttcg ccagttaata    6060
gtttgcgcaa cgttgttgcc attgctacag gcatcgtggt gtcacgctcg tcgtttggta    6120
tggcttcatt cagctccggt tcccaacgat caaggcgagt tacatgatcc cccatgttgt    6180
gcaaaaaagc ggttagctcc ttcggtcctc cgatcgttgt cagaagtaag ttggccgcag    6240
tgttatcact catggttatg gcagcactgc ataattctct tactgtcatg ccatccgtaa    6300
gatgcttttc tgtgactggt gagtactcaa ccaagtcatt ctgagaatag tgtatgcggc    6360
gaccgagttg ctcttgcccg gcgtcaatac gggataatac cgcgccacat agcagaactt    6420
taaaagtgct catcattgga aaacgttctt cggggcgaaa actctcaagg atcttaccgc    6480
tgttgagatc cagttcgatg taacccactc gtgcacccaa ctgatcttca gcatctttta    6540
ctttcaccag cgtttctggg tgagcaaaaa caggaaggca aaatgccgca aaaaagggaa    6600
taagggcgac acggaaatgt tgaatactca tactcttcct ttttcaatat tattgaagca    6660
tttatcaggg ttattgtctc atgagcggat acatatttga atgtatttag aaaaataaac    6720
aaataggggt tccgcgcaca tttccccgaa aagtgccacc taaattgtaa gcgttaatat    6780
tttgttaaaa ttcgcgttaa attttttgtta atcagctca tttttaacc aataggccga    6840
aatcggcaaa atcccttata aatcaaaaga atagaccgag atagggttga gtgttgttcc    6900
agtttggaac aagagtccac tattaaagaa cgtggactcc aacgtcaaag ggcgaaaaac    6960
cgtctatcag ggcgatggcc cactacgtga accatcaccc taatcaagtt ttttggggtc    7020
gaggtgccgt aaagcactaa atcggaaccc taaagggagc ccccgattta gagcttgacg    7080
gggaaagccg gcgaacgtgg cgagaaagga agggaagaaa gcgaaaggag cgggcgctag    7140
ggcgctggca agtgtagcgg tcacgctgcg cgtaaccacc acaccccgcc gcttaatgc    7200
gccgctacag ggcgcgtccc attcgccatt caggctcgcg aactgttggg aagggcgatc    7260
```

```
ggtgcgggcc tcttcgctat tacgccagct ggcgaaaggg ggatgtgctg caaggcgatt    7320
aagttgggta acgccagggt tttcccagtc acgacgttgt aaaacgacgg ccagtgagcg    7380
cgcgtaatac gactcactat agggcgaatt gggta                               7415

<210> SEQ ID NO 2
<211> LENGTH: 11569
<212> TYPE: DNA
<213> ORGANISM: Artificial Sequence
<220> FEATURE:
<223> OTHER INFORMATION: Coding Strand of Plasmid pHelper-Kan

<400> SEQUENCE: 2
ggtacccaac tccatgctta acagtcccca ggtacagccc accctgcgtc gcaaccagga      60
acagctctac agcttcctgg agcgccactc gccctacttc cgcagccaca gtgcgcagat     120
taggagcgcc acttcttttt gtcacttgaa aaacatgtaa aaataatgta ctaggagaca     180
ctttcaataa aggcaaatgt ttttatttgt acactctcgg gtgattattt acccccccacc    240 cttgccgtct gcgccgttta aaaatcaaag gggttctgcc gcgcatcgct atgcgccact     300
ggcagggaca cgttgcgata ctggtgttta gtgctccact taaactcagg cacaaccatc     360
cgcggcagct cggtgaagtt ttcactccac aggctgcgca ccatcaccaa cgcgtttagc     420
aggtcgggcg ccgatatctt gaagtcgcag ttggggcctc cgccctgcgc gcgcgagttg     480
cgatacacag ggttgcagca ctggaacact atcagcgccg ggtggtgcac gctggccagc     540
acgctcttgt cggagatcag atccgcgtcc aggtcctccg cgttgctcag ggcgaacgga     600
gtcaactttg gtagctgcct tcccaaaaag ggtgcatgcc caggctttga gttgcactcg     660
caccgtagtg gcatcagaag gtgaccgtgc ccggtctggg cgttaggata cagcgcctgc     720
atgaaagcct tgatctgctt aaaagccacc tgagcctttg cgccttcaga aagaacatg      780 ccgcaagact tgccggaaaa ctgattggcc ggacaggccg cgtcatgcac gcagcacctt     840
gcgtcggtgt tggagatctg caccacattt cggcccacc ggttcttcac gatcttggcc      900
ttgctagact gctccttcag cgcgcgctgc ccgttttcgc tcgtcacatc catttcaatc     960
acgtgctcct tatttatcat aatgctcccg tgtagacact taagctcgcc ttcgatctca   1020
gcgcagcggt gcagccacaa cgcgcagccc gtgggctcgt ggtgcttgta ggttacctct   1080
gcaaacgact gcaggtacgc ctgcaggaat cgccccatca tcgtcacaaa ggtcttgttg   1140
ctggtgaagg tcagctgcaa cccgcggtgc tcctcgttta gccaggtctt gcatacggcc   1200
gccagagctt ccacttggtc aggcagtagc ttgaagtttg cctttagatc gttatccacg   1260
tggtacttgt ccatcaacgc gcgcgcagcc tccatgccct tctcccacgc agacacgatc   1320
ggcaggctca gcgggtttat caccgtgctt tcactttccg cttcactgga ctcttccttt   1380
tcctcttgcg tccgcatacc ccgcgccact gggtcgtctt cattcagccg ccgcaccgtg   1440
cgcttacctc ccttgccgtg cttgattagc accggtgggt tgctgaaacc caccatttgt   1500
agcgccacat cttctctttc ttcctcgctg tccacgatca cctctgggga tggcgggcgc   1560
tcgggcttgg gagaggggcg cttctttttc ttttggacg caatggccaa atccgccgtc    1620
gaggtcgatg gccgcgggct gggtgtgcgc ggcaccagcg catcttgtga cgagtcttct   1680
tcgtcctcgg actcgagacg ccgcctcagc cgcttttttg gggcgcgcg gggaggcggc    1740 ggcgacggcg acgggacga cacgtcctcc atggttggtg gacgtcgcgc cgcaccgcgt    1800
ccgcgctcgg gggtggtttc gcgctgctcc tcttcccgac tggccatttc cttctcctat   1860
```

```
aggcagaaaa agatcatgga gtcagtcgag aaggaggaca gcctaaccgc cccctttgag   1920
ttcgccacca ccgcctccac cgatgccgcc aacgcgccta ccaccttccc cgtcgaggca   1980
cccccgcttg aggaggagga agtgattatc gagcaggacc caggttttgt aagcgaagac   2040
gacgaggatc gctcagtacc aacagaggat aaaaagcaag accaggacga cgcagaggca   2100
aacgaggaac aagtcgggcg gggggaccaa aggcatggcg actacctaga tgtgggagac   2160
gacgtgctgt tgaagcatct gcagcgccag tgcgccatta tctgcgacgc gttgcaagag   2220
cgcagcgatg tgcccctcgc catagcggat gtcagccttg cctacgaacg ccacctgttc   2280
tcaccgcgcg tacccccaa acgccaagaa acggcacat gcgagcccaa cccgcgcctc     2340
aacttctacc ccgtatttgc cgtgccagag gtgcttgcca cctatcacat cttttttccaa  2400 aactgcaaga taccctatc ctgccgtgcc aaccgcagcc gagcggacaa gcagctggcc    2460
ttgcggcagg gcgctgtcat acctgatatc gcctcgctcg acgaagtgcc aaaaatcttt   2520
gagggtcttg gacgcgacga gaaacgcgcg gcaaacgctc tgcaacaaga aaacagcgaa   2580
aatgaaagtc actgtggagt gctggtgaa cttgagggtg acaacgcgcg cctagccgtg    2640
ctgaaacgca gcatcgaggt cacccacttt gcctacccgg cacttaacct acccccaag    2700 gttatgagca cagtcatgag cgagctgatc gtgcgccgtg cacgacccct ggagagggat   2760
gcaaacttgc aagaacaaac cgaggagggc ctacccgcag ttggcgatga gcagctggcg   2820
cgctggcttg agacgcgcga gcctgccgac ttggaggagc gacgcaagct aatgatggcc   2880
gcagtgcttg ttaccgtgga gcttgagtgc atgcagcggt tctttgctga cccggagatg   2940
cagcgcaagc tagaggaaac gttgcactac acctttcgcc agggctacgt gcgccaggcc   3000
tgcaaaattt ccaacgtgga gctctgcaac ctggtctcct accttggaat tttgcacgaa   3060
aaccgcctcg gcaaaaacgt gcttcattcc acgtcaagg gcgaggcgcg ccgcgactac     3120
gtccgcgact gcgtttactt atttctgtgc tacacctggc aaacggccat gggcgtgtgg   3180
cagcaatgcc tggaggagcg caacctaaag gagctgcaga agctgctaaa gcaaaacttg   3240
aaggacctat ggacggcctt caacgagcgc tccgtggccg cgcacctggc ggacattatc   3300
ttccccgaac gcctgcttaa aaccctgcaa cagggtctgc cagacttcac cagtcaaagc   3360
atgttgcaaa actttaggaa cttttatccta gagcgttcag gaattctgcc cgccacctgc   3420
tgtgcgcttc ctagcgactt tgtgcccatt aagtaccgtg aatgccctcc gccgctttgg   3480
ggtcactgct accttctgca gctagccaac taccttgcct accactccga catcatggaa   3540
gacgtgagcg gtgacggcct actggagtgt cactgtcgct gcaacctatg caccccgcac   3600
cgctccctgg tctgcaattc gcaactgctt agcgaaagtc aaattatcgg tacctttgag   3660
ctgcagggtc cctcgcctga cgaaaagtcc gcggctccgg ggttgaaact cactccgggg   3720
ctgtggacgt cggcttacct tcgcaaattt gtacctgagg actaccacgc ccacgagatt   3780
aggttctacg aagaccaatc ccgcccgcca aatgcggagc ttaccgcctg cgtcattacc   3840
cagggccaca tccttggcca attgcaagcc atcaacaaag cccgcaagaa gtttctgcta   3900
cgaaagggac ggggggttta cctggacccc cagtccggcg aggagctcaa cccaatcccc   3960
ccgccgccgc agcccatca gcagccgcgg gcccttgctt cccaggatgg cacccaaaaa    4020
gaagctgcag ctgccgccgc cgccacccac ggacgaggag gaatactggg acagtcaggc   4080
agaggaggtt ttggacgagg aggaggagat gatggaagac tgggacagcc tagacgaagc   4140
ttccgaggcc gaagaggtgt cagacgaaac accgtcaccc tcggtcgcat tcccctcgcc   4200
ggcgccccag aaattggcaa ccgttcccag catcgctaca acctccgctc ctcaggcgcc   4260
```

```
gccggcactg cctgttcgcc gacccaaccg tagatgggac accactggaa ccagggccgg    4320
taagtctaag cagccgccgc cgttagccca agagcaacaa cagcgccaag gctaccgctc    4380
gtggcgcggg cacaagaacg ccatagttgc ttgcttgcaa gactgtgggg gcaacatctc    4440
cttcgcccgc cgctttcttc tctaccatca cggcgtggcc ttcccccgta acatcctgca    4500
ttactaccgt catctctaca gcccctactg caccggcggc agcggcagcg gcagcaacag    4560
cagcggtcac acagaagcaa aggcgaccgg atagcaagac tctgacaaag cccaagaaat    4620
ccacagcggc ggcagcagca ggaggaggag cgctgcgtct ggcgcccaac gaacccgtat    4680
cgacccgcga gcttagaaat aggatttttc ccactctgta tgctatattt caacaaagca    4740
ggggccaaga acaagagctg aaaataaaaa acaggtctct gcgctccctc acccgcagct    4800
gcctgtatca caaagcgaa gatcagcttc ggcgcacgct ggaagacgcg gaggctctct    4860
tcagcaaata ctgcgcgctg actcttaagg actagtttcg cgccctttct caaatttaag    4920
cgcgaaaact acgtcatctc cagcggccac acccggcgcc agcacctgtc gtcagcgcca    4980
ttatgagcaa ggaaattccc acgccctaca tgtggagtta ccagccacaa atgggacttg    5040
cggctggagc tgcccaagac tactcaaccc gaataaacta catgagcgcg ggaccccaca    5100
tgatatcccg ggtcaacgga atccgcgccc accgaaaccg aattctcctc gaacaggcgg    5160
ctattaccac cacacctcgt aataaccta atccccgtag ttggcccgct gcctggtgt    5220 accaggaaag tcccgctccc accactgtgg tacttcccag agacgcccag gccgaagttc    5280
agatgactaa ctcaggggcg cagcttgcgg cggcttttcg tcacagggtg cggtcgcccg    5340
ggcgttttag ggcggagtaa cttgcatgta ttgggaattg tagttttttt aaaatgggaa    5400
gtgacgtatc gtgggaaaac ggaagtgaag atttgaggaa gttgtgggtt ttttggcttt    5460
cgtttctggg cgtaggttcg cgtgcggttt tctgggtgtt ttttgtggac tttaaccgtt    5520
acgtcatttt ttagtcctat atatactcgc tctgtacttg gccctttta cactgtgact    5580 gattgagctg gtgccgtgtc gagtggtgtt ttttaatagg tttttttact ggtaaggctg    5640
actgttatgg ctgccgctgt ggaagcgctg tatgttgttc tggagcggga gggtgctatt    5700
ttgcctaggc aggagggttt ttcaggtgtt tatgtgtttt tctctcctat taattttgtt    5760
atacctccta tggggctgt aatgttgtct ctacgcctgc gggtatgtat tccccgggc    5820 tatttcggtc gcttttagc actgaccgat gttaaccaac ctgatgtgtt taccgagtct    5880
tacattatga ctccggacat gaccgaggaa ctgtcggtgg tgcttttaa tcacggtgac    5940 cagttttttt acggtcacgc cggcatggcc gtagtccgtc ttatgcttat aagggttgtt    6000
tttcctgttg taagacaggc ttctaatgtt taaatgtttt ttttttgtt attttatttt    6060 gtgtttaatg caggaacccg cagacatgtt tgagagaaaa atggtgtctt ttctcgtggt    6120
ggttccggaa cttacctgcc tttatctgca tgagcatgac tacgatgtgc ttgctttttt    6180
gcgcgaggct ttgcctgatt ttttgagcag caccttgcat tttatatcgc cgcccatgca    6240
acaagcttac atagggcta cgctggttag catagctccg agtatgcgtg tcataatcag    6300
tgtgggttct tttgtcatgg ttcctggcgg ggaagtggcc gcgctggtcc gtgcagacct    6360
gcacgattat gttcagctgg ccctgcgaag ggacctacgg gatcgcggta ttttgttaa    6420 tgttccgctt ttgaatctta tacaggtctg tgaggaacct gaattttgc aatcatgatt    6480 cgctgcttga ggctgaaggt ggagggcgct ctggagcaga tttttacaat ggccggactt    6540
aatattcggg atttgcttag agacatattg ataaggtggc gagatgaaaa ttatttgggc    6600
```

-continued

| | |
|---|---|
| atggttgaag gtgctggaat gtttatagag gagattcacc ctgaagggtt tagcctttac | 6660 |
| gtccacttgg acgtgagggc agtttgcctt ttggaagcca ttgtgcaaca tcttacaaat | 6720 |
| gccattatct gttctttggc tgtagagttt gaccacgcca ccggagggga gcgcgttcac | 6780 |
| ttaatagatc ttcattttga ggttttggat aatcttttgg aataaaaaaa aaaaaacatg | 6840 |
| gttcttccag ctcttcccgc tcctcccgtg tgtgactcgc agaacgaatg tgtaggttgg | 6900 |
| ctgggtgtgg cttattctgc ggtggtggat gttatcaggg cagcggcgca tgaaggagtt | 6960 |
| tacatagaac ccgaagccag ggggcgcctg gatgctttga gagagtggat atactacaac | 7020 |
| tactacacag agcgagctaa cgacgagac cggagacgca gatctgtttg tcacgcccgc | 7080 |
| acctggtttt gcttcaggaa atatgactac gtccggcgtt ccatttggca tgacactacg | 7140 |
| accaacacga tctcggttgt ctcggcgcac tccgtacagt agggatcgcc tacctccttt | 7200 |
| tgagacagag accgcgcta ccatactgga ggatcatccg ctgctgcccg aatgtaacac | 7260 |
| tttgacaatg cacaacgtga gttacgtgcg aggtcttccc tgcagtgtgg gatttacgct | 7320 |
| gattcaggaa tgggttgttc cctgggatat ggttctgacg cggaggagc ttgtaatcct | 7380 |
| gaggaagtgt atgcacgtgt gcctgtgttg tgccaacatt gatatcatga cgagcatgat | 7440 |
| gatccatggt tacgagtcct gggctctcca ctgtcattgt tccagtcccg gttcctgca | 7500 |
| gtgcatagcc ggcgggcagg ttttggccag ctggtttagg atggtggtgg atggcgccat | 7560 |
| gtttaatcag aggtttatat ggtaccggga ggtggtgaat tacaacatgc aaaagaggt | 7620 |
| aatgtttatg tccagcgtgt ttatgagggg tcgccactta atctacctgc gcttgtggta | 7680 |
| tgatggccac gtgggttctg tggtcccgc catgagcttt ggatacagcg ccttgcactg | 7740 |
| tgggattttg aacaatattg tggtgctgtg ctgcagttac tgtgctgatt taagtgagat | 7800 |
| cagggtgcgc tgctgtgccc ggaggacaag gcgtctcatg ctgcgggcgg tgcgaatcat | 7860 |
| cgctgaggag accactgcca tgttgtattc ctgcaggacg gagcggcggc ggcagcagtt | 7920 |
| tattcgcgcg ctgctgcagc accaccgccc tatcctgatg cacgattatg actctacccc | 7980 |
| catgtaggcg tggacttccc cttcgccgcc cgttgagcaa ccgcaagttg gacagcagcc | 8040 |
| tgtggctcag cagctggaca gcgacatgaa cttaagcgag ctgcccgggg agtttattaa | 8100 |
| tatcactgat gagcgtttgg ctcgacagga aaccgtgtgg aatataacac taagaatat | 8160 |
| gtctgttacc catgatatga tgcttttttaa ggccagccgg ggagaaagga ctgtgtactc | 8220 |
| tgtgtgttgg gagggaggtg gcaggttgaa tactagggtt ctgtgagttt gattaaggta | 8280 |
| cggtgatcaa tataagctat gtggtggtgg ggctatacta ctgaatgaaa aatgacttga | 8340 |
| aattttctgc aattgaaaaa taaacacgtt gaaacataac atgcaacagg ttcacgattc | 8400 |
| tttattcctg ggcaatgtag gagaaggtgt aagagttggt agcaaaagtt tcagtggtgt | 8460 |
| attttccact ttcccaggac catgtaaaag acatagagta agtgcttacc tcgctagttt | 8520 |
| ctgtggattc actagaatcg atgtaggatg ttgcccctcc tgacgcggta ggagaagggg | 8580 |
| agggtgccct gcatgtctgc cgctgctctt gctcttgccg ctgctgagga gggggcgca | 8640 |
| tctgccgcag caccggatgc atctgggaaa agcaaaaaag gggctcgtcc ctgtttccgg | 8700 |
| aggaatttgc aagcggggtc ttgcatgacg gggaggcaaa ccccgttcg ccgcagtccg | 8760 |
| gccggcccga gactcgaacc ggggggtcctg cgactcaacc cttggaaaat aaccctccgg | 8820 |
| ctacagggag cgagccactt aatgctttcg cttttccagcc taaccgctta cgccgcgcgc | 8880 |
| ggccagtggc caaaaaagct agcgcagcag ccgccgcgcc tggaaggaag ccaaaaggag | 8940 |
| cgctccccg ttgtctgacg tcgcacacct gggttcgaca cgcgggcggt aaccgcatgg | 9000 |

```
atcacggcgg acggccggat ccggggttcg aacccggtc gtccgccatg ataccttgc    9060
gaatttatcc accagaccac ggaagagtgc ccgcttacag gctctccttt tgcacggtct   9120
agagcgtcaa cgactgcgca cgcctcaccg gccagagcgt cccgaccatg gagcactttt   9180
tgccgctgcg caacatctgg aaccgcgtcc gcgactttcc gcgcgcctcc accaccgccg   9240
ccggcatcac ctggatgtcc aggtacatct acggattacg tcgacgttta aaccatatga   9300
tcagctcact caaaggcggt aatacggtta tccacagaat caggggataa cgcaggaaag   9360
aacatgtgag caaaaggcca gcaaaaggcc aggaaccgta aaaaggccgc gttgctggcg   9420
tttttccata ggctccgccc ccctgacgag catcacaaaa atcgacgctc aagtcagagg   9480
tggcgaaacc cgacaggact ataaagatac caggcgtttc ccctggaag ctccctcgtg   9540
cgctctcctg ttccgaccct gccgcttacc ggatacctgt ccgcctttct cccttcggga   9600
agcgtggcgc tttctcatag ctcacgctgt aggtatctca gttcggtgta ggtcgttcgc   9660
tccaagctgg gctgtgtgca cgaaccccc gttcagcccg accgctgcgc cttatccggt    9720
aactatcgtc ttgagtccaa cccggtaaga cacgacttat cgccactggc agcagccact   9780
ggtaacagga ttagcagagc gaggtatgta ggcggtgcta cagagttctt gaagtggtgg   9840
cctaactacg gctacactag aagaacagta tttggtatct gcgctctgct gaagccagtt   9900
accttcggaa aaagagttgg tagctcttga tccggcaaac aaaccaccgc tggtagcggt   9960
ggtttttttg tttgcaagca gcagattacg cgcagaaaaa aaggatctca agaagatcct   10020
ttgatctttt ctacggggtc tgacgctcag tggaacgaaa actcacgtta agggattttg   10080
gtcatgagat tatcaaaaag gatcttcacc tagatccttt taaattaaaa atgaagtttt   10140
aaatcaatct aaagtatata tgagtaaact tggtctgaca gtcagaagaa ctcgtcaaga   10200
aggcgataga aggcgatgcg ctgcgaatcg ggagcggcga taccgtaaag cacgaggaag   10260
cggtcagccc attcgccgcc aagctcttca gcaatatcac gggtagccaa cgctatgtcc   10320
tgatagcggt ccgccacacc cagccggcca cagtcgatga atccagaaaa gcggccattt   10380
tccaccatga tattcggcaa gcaggcatcg ccatgggtca cgacgagatc ctcgccgtcg   10440
ggcatgctcg ccttgagcct ggcgaacagt tcggctggcg cgagcccctg atgctcttcg   10500
tccagatcat cctgatcgac aagaccggct tccatccgag tacgtgctcg ctcgatgcga   10560
tgtttcgctt ggtggtcgaa tgggcaggta gccggatcaa gcgtatgcag ccgccgcatt   10620
gcatcagcca tgatggatac tttctcggca ggagcaaggt gagatgacag gagatcctgc   10680
cccggcactt cgcccaatag cagccagtcc cttcccgctt cagtgacaac gtcgagtaca   10740
gctgcgcaag gaacgcccgt cgtggccagc cacgatagcc gcgctgcctc gtcttgcagt   10800
tcattcaggg caccggacag gtcggtcttg acaaaaagaa ccgggcgccc ctgcgctgac   10860
agccggaaca cggcggcatc agagcagccg attgtctgtt gtgcccagtc atagccgaat   10920
agcctctcca cccaagcggc cggagaacct gcgtgcaatc catcttgttc aatcatactc   10980
ttccttttc aatattattg aagcatttat cagggttatt gtctcatgag cggatacata   11040
tttgaatgta tttagaaaaa taaacaaata ggggttccgc gcacatttcc ccgaaaagtg   11100
ccacctaaat tgtaagcgtt aatattttgt taaaattcgc gttaaatttt tgttaaatca   11160
gctcattttt taaccaatag gccgaaatcg gcaaaatccc ttataaatca aagaataga   11220
ccgagatagg gttgagtgtt gttccagttt ggaacaagag tccactatta agaacgtgg   11280
actccaacgt caaagggcga aaaccgtct atcagggcga tggcccacta cgtgaaccat   11340
```

| | |
|---|---|
| cacccταatc aagttttttg gggtcgaggt gccgtaaagc actaaatcgg aaccctaaag | 11400 |
| ggagccccg atttagagct tgacggggaa agccggcgaa cgtggcgaga aggaaggga | 11460 |
| agaaagcgaa aggagcgggc gctagggcgc tggcaagtgt agcggtcacg ctgcgcgtaa | 11520 |
| ccaccacacc cgccgcgctt aatgcgccgc tacagggcgc gatggatcc | 11569 |

<210> SEQ ID NO 3
<211> LENGTH: 5030
<212> TYPE: DNA
<213> ORGANISM: Artificial Sequence
<220> FEATURE:
<223> OTHER INFORMATION: Coding Strand of Plasmid pAV-CMV-EGFP

<400> SEQUENCE: 3

| | |
|---|---|
| cctgcaggca gctgcgcgct cgctcgctca ctgaggccgc cgggcgtcg ggcgaccttt | 60 |
| ggtcgcccgg ccctccagtg agcgagcgcg cagagaggga gtggccaact ccatcactag | 120 |
| gggttcctgc ggccgcacgc gtctagttat taatagtaat cgaattcgtg ttactcataa | 180 |
| ctagtaaggt cgggcaggaa gagggcctat ttcccatgat tccttcatat ttgcatatac | 240 |
| gatacaaggc tgttagagag ataattagaa ttaatttgac tgtaaacaca agatattag | 300 |
| tacaaaatac gtgacgtaga aagtaataat ttcttgggta gtttgcagtt ttaaaattat | 360 |
| gttttaaaat ggactatcat atgcttaccg taacttgaaa gtatttcgat ttcttgggtt | 420 |
| tatatatctt gtggaaagga cgcgggatcc actggaccag gcagcagcgt cagaagactt | 480 |
| ttttggaaaa gcttgactag taatactgta atagtaatca attacggggt cattagttca | 540 |
| tagcccatat atggagttcc gcgttacata acttacggta aatggcccgc ctggctgacc | 600 |
| gcccaacgac ccccgcccat tgacgtcaat aatgacgtat gttcccatag taacgccaat | 660 |
| agggactttc cattgacgtc aatgggtgga gtatttacgg taaactgccc acttggcagt | 720 |
| acatcaagtg tatcatatgc caagtacgcc ccctattgac gtcaatgacg gtaaatggcc | 780 |
| cgcctggcat tatgcccagt acatgacctt atgggacttt cctacttggc agtacatcta | 840 |
| cgtattagtc atcgctatta ccatggtgat gcggttttgg cagtacatca atgggcgtgg | 900 |
| atagcggttt gactcacggg gatttccaag tctccacccc attgacgtca tgggagtttt | 960 |
| gttttgcacc aaaatcaacg ggactttcca aaatgtcgta caactccgc cccattgacg | 1020 |
| caaatgggcg gtaggcgtgt acggtgggag gtctatataa gcagagctgg tttagtgaac | 1080 |
| cgtcagatcc gctagagatc cggtaccgag gagatctgcc gccgcgatcg ccggcgcgcc | 1140 |
| agatctcacg cttaactagc tagcggaccg acgcgtacgc ggccgctcga gatggtgagc | 1200 |
| aagggcgagg agctgttcac cggggtggtg cccatcctgg tcgagctgga cggcgacgta | 1260 |
| aacggccaca gttcagcgt gtccggcgag ggcgagggcg atgccaccta cggcaagctg | 1320 |
| accctgaagt tcatctgcac caccggcaag ctgcccgtgc cctggcccac cctcgtgacc | 1380 |
| accctgacct acggcgtgca gtgcttcagc cgctacccg accacatgaa gcagcacgac | 1440 |
| ttcttcaagt ccgccatgcc cgaaggctac gtccaggagc gcaccatctt cttcaaggac | 1500 |
| gacggcaact acaagacccg cgccgaggtg aagttcgagg gcgacaccct ggtgaaccgc | 1560 |
| atcgagctga agggcatcga cttcaaggag gacggcaaca tcctggggca caagctggag | 1620 |
| tacaactaca acagccacaa cgtctatatc atggccgaca agcagaagaa cggcatcaag | 1680 |
| gtgaacttca agatccgcca caacatcgag gacggcagcg tgcagctcgc cgaccactac | 1740 |
| cagcagaaca cccccatcgg cgacggcccc gtgctgctgc ccgacaacca ctacctgagc | 1800 |
| acccagtccg ccctgagcaa agaccccaac gagaagcgcg atcacatggt cctgctggag | 1860 |

```
ttcgtgaccg ccgccgggat cactctcggc atggacgagc tgtacaagta agtcgaggat    1920
tataaggatg acgacgataa attcgtcgag caccaccacc accaccacta ataaggttta    1980
tccgatccac cggatctaga taagatatcc gatccaccgg atctagataa ctgatcataa    2040
tcagccatac cacatttgta gaggttttac ttgctttaaa aaacctccca cacctccccc    2100
tgaacctgaa acataaaatg aatgcaattg ttgttgttaa cttgtttatt gcagcttata    2160
atggttacaa ataaagcaat agcatcacaa atttcacaaa taaagcattt ttttcactgc    2220
attctagttg tggtttgtcc aaactcatca atgtatctta acgcggtaac cacgtgcgga    2280
ccgagcggcc gcaggaaccc ctagtgatgg agttggccac tccctctctg cgcgctcgct    2340
cgctcactga ggccgggcga ccaaaggtcg cccgacgccc gggctttgcc cgggcggcct    2400
cagtgagcga gcgagcgcgc agctgcctgc aggggcgcct gatgcggtat tttctcctta    2460
cgcatctgtg cggtatttca caccgcatac gtcaaagcaa ccatagtacg cccctgtag    2520 cggcgcatta agcgcggcgg gtgtggtggt tacgcgcagc gtgaccgcta cacctgccag    2580
cgccttagcg cccgctcctt tcgctttctt cccttccttt ctcgccacgt tcgccggctt    2640
tccccgtcaa gctctaaatc gggggctccc tttagggttc cgatttagtg ctttacggca    2700
cctcgacccc aaaaaacttg atttgggtga tggttcacgt agtgggccat cgccctgata    2760
gacggttttt cgccctttga cgttggagtc cacgttcttt aatagtggac tcttgttcca    2820
aactggaaca acactcaacc ctatctcggg ctattctttt gatttataag ggattttgcc    2880
gatttcggcc tattggttaa aaaatgagct gatttaacaa aaatttaacg cgaattttaa    2940
caaaatatta cgtttacaa ttttatggtg cactctcagt acaatctgct ctgatgccgc    3000
atagttaagc cagccccgac acccgccaac acccgctgac gcgccctgac gggcttgtct    3060
gctcccggca tccgcttaca dacaagctgt gaccgtctcc gggagctgca tgtgtcagag    3120
gttttcaccg tcatcaccga aacgcgcgag acgaaagggc ctcgtgatac gcctattttt    3180
ataggttaat gtcatgataa taatggtttc ttagacgtca ggtggcactt ttcggggaaa    3240
tgtgcgcgga accctattt gtttattttt ctaaatacat tcaaatatgt atccgctcat    3300
gagacaataa ccctgataaa tgcttcaata atattgaaaa aggaagagta tgagtattca    3360
acatttccgt gtcgccctta ttccctttt tgcggcattt tgccttcctg ttttgctca    3420 cccagaaacg ctggtgaaag taaaagatgc tgaagatcag ttgggtgcac gagtgggtta    3480
catcgaactg gatctcaaca gcggtaagat ccttgagagt tttcgccccg aagaacgttt    3540
tccaatgatg agcactttta aagttctgct atgtggcgcg gtattatccc gtattgacgc    3600
cgggcaagag caactcggtc gccgcataca ctattctcag aatgacttgg ttgagtactc    3660
accagtcaca gaaaagcatc ttacggatgg catgacagta agagaattat gcagtgctgc    3720
cataaccatg agtgataaca ctgcggccaa cttacttctg acaacgatcg gaggaccgaa    3780
ggagctaacc gcttttttgc acaacatggg ggatcatgta actcgccttg atcgttggga    3840
accggagctg aatgaagcca taccaaacga cgagcgtgac accacgatgc ctgtagcaat    3900
ggcaacaacg ttgcgcaaac tattaactgg cgaactactt actctagctt cccggcaaca    3960
attaatagac tggatggagg cggataaagt tgcaggacca cttctgcgct cggcccttcc    4020
ggctggctgg tttattgctg ataaatctgg agccggtgag cgtgggtctc gcggtatcat    4080
tgcagcactg gggccagatg gtaagccctc ccgtatcgta gttatctaca cgacggggag    4140
tcaggcaact atggatgaac gaaatagaca gatcgctgag ataggtgcct cactgattaa    4200
```

| | |
|---|---|
| gcattggtaa ctgtcagacc aagtttactc atatatactt tagattgatt taaaacttca | 4260 |
| tttttaattt aaaaggatct aggtgaagat ccttttttgat aatctcatga ccaaaatccc | 4320 |
| ttaacgtgag ttttcgttcc actgagcgtc agaccccgta gaaaagatca aaggatcttc | 4380 |
| ttgagatcct tttttctgc gcgtaatctg ctgcttgcaa acaaaaaaac caccgctacc | 4440 |
| agcggtggtt tgtttgccgg atcaagagct accaactctt tttccgaagg taactggctt | 4500 |
| cagcagagcg cagataccaa atactgtcct tctagtgtag ccgtagttag gccaccactt | 4560 |
| caagaactct gtagcaccgc ctacatacct cgctctgcta atcctgttac cagtggctgc | 4620 |
| tgccagtggc gataagtcgt gtcttaccgg gttggactca agacgatagt taccggataa | 4680 |
| ggcgcagcgg tcgggctgaa cggggggttc gtgcacacag cccagcttgg agcgaacgac | 4740 |
| ctacaccgaa ctgagatacc tacagcgtga gctatgagaa agcgccacgc ttcccgaagg | 4800 |
| gagaaaggcg gacaggtatc cggtaagcgg cagggtcgga acaggagagc gcacgaggga | 4860 |
| gcttccaggg ggaaacgcct ggtatcttta tagtcctgtc gggtttcgcc acctctgact | 4920 |
| tgagcgtcga ttttgtgat gctcgtcagg ggggcggagc ctatggaaaa acgccagcaa | 4980 |
| cgcggccttt ttacggttcc tggccttttg ctggcctttt gctcacatgt | 5030 |

<210> SEQ ID NO 4
<211> LENGTH: 4742
<212> TYPE: DNA
<213> ORGANISM: Artificial Sequence
<220> FEATURE:
<223> OTHER INFORMATION: Coding Strand of Plasmid pAV-TBG-EGFP

<400> SEQUENCE: 4

| | |
|---|---|
| cctgcaggca gctgcgcgct cgctcgctca ctgaggccgc ccgggcgtcg ggcgaccttt | 60 |
| ggtcgcccgg cctcagtgag cgagcgagcg cgcagagagg gagtggccaa ctccatcact | 120 |
| aggggttcct gcggccggtc gcgtctagta ctagtaggtt aattttaaa aagcagtcaa | 180 |
| aagtccaagt ggcccttggc agcatttact ctctctgttt gctctggtta ataatctcag | 240 |
| gagcacaaac attccagatc caggttaatt tttaaaaagc agtcaaaagt ccaagtggcc | 300 |
| cttggcagca tttactctct ctgtttgctc tggttaataa tctcaggagc acaaacattc | 360 |
| cagatccggc gcgccagggc tggaagctac ctttgacatc atttcctctg cgaatgcatg | 420 |
| tataatttct acagaaccta ttagaaagga tcacccagcc tctgcttttg tacaactttc | 480 |
| ccttaaaaaa ctgccaattc cactgctgtt tggcccaata gtgagaactt ttcctgctg | 540 |
| cctcttggtg cttttgccta tggccccctat tctgcctgct gaagacactc ttgccagcat | 600 |
| ggacttaaac ccctccagct ctgacaatcc tctttctctt ttgttttaca tgaagggtct | 660 |
| ggcagccaaa gcaatcactc aaagttcaaa cctatcatt ttttgctttg ttcctcttgg | 720 |
| ccttggtttt gtacatcagc tttgaaaata ccatcccagg gttaatgctg gggttaattt | 780 |
| ataactaaga gtgctctagt tttgcaatac aggacatgct ataaaaatgg aaagatgttg | 840 |
| ctttctgaga gacaggtacc gaggagatct gccgccgcga tcgccaccat ggtgagcaag | 900 |
| ggcgaggagc tgttcaccgg ggtggtgccc atcctggtcg agctggacgg cgacgtaaac | 960 |
| ggccacaagt tcagcgtgtc cggcgagggc gagggcgatg ccacttacgg caagctgacc | 1020 |
| ctgaagttca tctgcaccac cggcaagctg cccgtgccct ggcccaccct cgtgaccacc | 1080 |
| ctgacctacg gcgtgcagtg cttcagccgc taccccgacc acatgaagca gcacgacttc | 1140 |
| ttcaagtccg ccatgcccga aggctacgtc caggagcgca ccatcttctt caaggacgac | 1200 |
| ggcaactaca agacccgcgc cgaggtgaag ttcgagggcg acaccctggt gaaccgcatc | 1260 |

```
gagctgaagg gcatcgactt caaggaggac ggcaacatcc tggggcacaa gctggagtac    1320
aactacaaca gccacaacgt ctatatcatg gccgacaagc agaagaacgg catcaaggtg    1380
aacttcaaga tccgccacaa catcgaggac ggcagcgtgc agctcgccga ccactaccag    1440
cagaacaccc ccatcggcga cggccccgtg ctgctgcccg acaaccacta cctgagcacc    1500
cagtccgccc tgagcaaaga ccccaacgag aagcgcgatc acatggtcct gctggagttc    1560
gtgaccgccg ccgggatcac tctcggcatg gacgagctgt acaagtagac gcgtacgcgg    1620
ccgctcgagg attataagga tgacgacgat aaattcgtcg agcaccacca ccaccaccac    1680
taataaggtt tatccgatcc accggatcta gataagatat ccgatccacc ggatctagat    1740
aactgatcat aatcagccat accacatttg tagaggtttt acttgcttta aaaaacctcc    1800
cacacctccc cctgaacctg aaacataaaa tgaatgcaat tgttgttgtt aacttgttta    1860
ttgcagctta taatggttac aaataaagca atagcatcac aaatttcaca ataaagcat    1920 tttttcact gcattctagt tgtggtttgt ccaaactcat caatgtatct taacgcggta    1980
accacgtgcg gacccaacgg ccgcaggaac ccctagtgat ggagttggcc actccctctc    2040
tgcgcgctcg ctcgctcact gaggccgggc gaccaaaggt cgcccgacgc ccgggctttg    2100
cccgggcggc ctcagtgagc gagcgagcgc gcagctgcct gcaggggcgc ctgatgcggt    2160
attttctcct tacgcatctg tgcggtattt cacaccgcat acgtcaaagc aaccatagta    2220
cgcgccctgt agcggcacat taagcgcggc gggtgtggtg gttacgcgca gcgtgaccgc    2280
tacacctgcc agcgccttag cgcccgctcc tttcgctttc ttcccttcct ttctcgccac    2340
gttcgccggc tttccccgtc aagctctaaa tcggggggct ccctttagggt tccgatttag    2400 tgctttacgg cacctcgacc ccaaaaaact tgatttgggt gatggttcac gtagtgggcc    2460
atcgccctga tagacggttt ttcgcccttt gacgttggag tccacgttct ttaatagtgg    2520
actcttgttc caaactggaa caacactcaa ctctatctcg gctattctt ttgatttata    2580 agggattttg ccgatttcgg tctattggtt aaaaaatgag ctgatttaac aaaaatttaa    2640
cgcgaatttt aacaaaatat taacgtttac aattttatgg tgcactctca gtacaatctg    2700
ctctgatgcc gcatagttaa gccagccccg acacccgcca cacccgctg acgcgccctg    2760 acgggcttgt ctgctcccgg catccgctta cagacaagct gtgaccgtct ccgggagctg    2820
catgtgtcag aggttttcac cgtcatcacc gaaacgcgcg agacgaaagg gcctcgtgat    2880
acgcctattt ttataggtta atgtcatgat aataatggtt tcttagacgt caggtggcac    2940
ttttcgggga atgtgcgcg gaaccctat ttgtttattt ttctaaatac attcaaatat    3000
gtatccgctc atgagacaat aaccctgata aatgcttcaa taatattgaa aaggaagag    3060 tatgagtatt caacatttcc gtgtcgccct tattccctt tttgcggcat tttgccttcc    3120 tgttttgct cacccagaaa cgctggtgaa agtaaaagat gctgaagatc agttgggtgc    3180
acgagtgggt tacatcgaac tggatctcaa cagcggtaag atccttgaga gttttcgccc    3240
cgaagaacgt tttccaatga tgagcacttt taaagttctg ctatgtggcg cggtattatc    3300
ccgtattgac gccgggcaag agcaactcgg tcgccgcata cactattctc agaatgactt    3360
ggttgagtac tcaccagtca cagaaaagca tcttacggat ggcatgacag taagagaatt    3420
atgcagtgct gccataacca tgagtgataa cactgcggcc aacttacttc tgacaacgat    3480
cggaggaccg aaggagctaa ccgcttttt gcacaacatg ggggatcatg taactcgcct    3540
tgatcgttgg gaaccggagc tgaatgaagc cataccaaac gacgagcgtg acaccacgat    3600
```

-continued

```
gcctgtagca atggcaacaa cgttgcgcaa actattaact ggcgaactac ttactctagc    3660
ttcccggcaa caattaatag actggatgga ggcggataaa gttgcaggac cacttctgcg    3720
ctcggccctt ccggctggct ggtttattgc tgataaatct ggagccggtg agcgtgggtc    3780
tcgcggtatc attgcagcac tggggccaga tggtaagccc tcccgtatcg tagttatcta    3840
cacgacgggg agtcaggcaa ctatggatga acgaaataga cagatcgctg agataggtgc    3900
ctcactgatt aagcattggt aactgtcaga ccaagtttac tcatatatac tttagattga    3960
tttaaaacttc catttttaat ttaaaaggat ctaggtgaag atcctttttg ataatctcat    4020
gaccaaaatc ccttaacgtg agttttcgtt ccactgagcg tcagacccc g tagaaaagat    4080
caaaggatct tcttgagatc ctttttttct gcgcgtaatc tgctgcttgc aaacaaaaaa    4140
accaccgcta ccagcggtgg tttgtttgcc ggatcaagag ctaccaactc tttttccgaa    4200
ggtaactggc ttcagcagag cgcagatacc aaatactgtt cttctagtgt agccgtagtt    4260
aggccaccac ttcaagaact ctgtagcacc gcctacatac ctcgctctgc taatcctgtt    4320
accagtggct gctgccagtg gcgataagtc gtgtcttacc gggttggact caagacgata    4380
gttaccggat aaggcgcagc ggtcgggctg aacggggggt tcgtgcacac agcccagctt    4440
ggagcgaacg acctacaccg aactgagata cctacagcgt gagctatgag aaagcgccac    4500
gcttcccgaa gggagaaagg cggacaggta tccggtaagc ggcagggtcg gaacaggaga    4560
gcgcacgagg gagcttccag ggggaaacgc ctggtatctt tatagtcctg tcgggtttcg    4620
ccacctctga cttgagcgtc gatttttgtg atgctcgtca gggggggcgga gcctatggaa    4680
aaacgccagc aacgcggcct ttttacggtt cctggccttt tgctggcctt ttgctcacat    4740
gt                                                                   4742
```

<210> SEQ ID NO 5
<211> LENGTH: 20
<212> TYPE: DNA
<213> ORGANISM: Artificial Sequence
<220> FEATURE:
<223> OTHER INFORMATION: Cis Element CisE1 (GQ4)

<400> SEQUENCE: 5
gggtggccga gaaggaatgg                                                20

<210> SEQ ID NO 6
<211> LENGTH: 20
<212> TYPE: DNA
<213> ORGANISM: Artificial Sequence
<220> FEATURE:
<223> OTHER INFORMATION: Cis Element CisE1-Rev (GQ4-Rev)

<400> SEQUENCE: 6
ggtaaggaag agccggtggg                                                20

<210> SEQ ID NO 7
<211> LENGTH: 29
<212> TYPE: DNA
<213> ORGANISM: Artificial Sequence
<220> FEATURE:
<223> OTHER INFORMATION: Cis Element CisE2 (GQ5)

<400> SEQUENCE: 7
ggaatggcgc cgtgtgagta aggccccgg                                      29

<210> SEQ ID NO 8
<211> LENGTH: 29

```
<212> TYPE: DNA
<213> ORGANISM: Artificial Sequence
<220> FEATURE:
<223> OTHER INFORMATION: Cis Element CisE2-Rev (GQ5-Rev)

<400> SEQUENCE: 8
ggccccggaa tgagtgtgcc gcggtaagg                                       29

<210> SEQ ID NO 9
<211> LENGTH: 26
<212> TYPE: DNA
<213> ORGANISM: Artificial Sequence
<220> FEATURE:
<223> OTHER INFORMATION: Cis Element CisE3 (GQ6)

<400> SEQUENCE: 9
ggaaaccacc ggggtgaaat ccatgg                                          26

<210> SEQ ID NO 10
<211> LENGTH: 26
<212> TYPE: DNA
<213> ORGANISM: Artificial Sequence
<220> FEATURE:
<223> OTHER INFORMATION: Cis Element CisE3-Rev (GQ6-Rev)

<400> SEQUENCE: 10
ggtacctaaa gtggggccac caaagg                                          26

<210> SEQ ID NO 11
<211> LENGTH: 22
<212> TYPE: DNA
<213> ORGANISM: Artificial Sequence
<220> FEATURE:
<223> OTHER INFORMATION: Cis Element CisE4 (GQ7)

<400> SEQUENCE: 11
ggaggcggga acaaggtggt gg                                              22

<210> SEQ ID NO 12
<211> LENGTH: 22
<212> TYPE: DNA
<213> ORGANISM: Artificial Sequence
<220> FEATURE:
<223> OTHER INFORMATION: Cis Element CisE4-Rev (GQ7-Rev)

<400> SEQUENCE: 12
ggtggtggaa caaggcgga gg                                               22

<210> SEQ ID NO 13
<211> LENGTH: 18
<212> TYPE: DNA
<213> ORGANISM: Artificial Sequence
<220> FEATURE:
<223> OTHER INFORMATION: Cis Element CisE5 (GQ10)

<400> SEQUENCE: 13
ggatccagga ggaccagg                                                   18

<210> SEQ ID NO 14
<211> LENGTH: 18
<212> TYPE: DNA
<213> ORGANISM: Artificial Sequence
<220> FEATURE:
<223> OTHER INFORMATION: Cis Element CisE5-Rev (GQ10-Rev)

<400> SEQUENCE: 14
```

```
ggaccaggag gacctagg                                                    18

<210> SEQ ID NO 15
<211> LENGTH: 30
<212> TYPE: DNA
<213> ORGANISM: Artificial Sequence
<220> FEATURE:
<223> OTHER INFORMATION: Cis Element CisE6 (GQ12)

<400> SEQUENCE: 15
ggcaagagga acaccatctg gctgtttggg                                       30

<210> SEQ ID NO 16
<211> LENGTH: 30
<212> TYPE: DNA
<213> ORGANISM: Artificial Sequence
<220> FEATURE:
<223> OTHER INFORMATION: Cis Element CisE6-Rev (GQ12-Rev)

<400> SEQUENCE: 16
gggtttgtcg gtctaccaca aggagaacgg                                       30

<210> SEQ ID NO 17
<211> LENGTH: 22
<212> TYPE: DNA
<213> ORGANISM: Artificial Sequence
<220> FEATURE:
<223> OTHER INFORMATION: Cis Element CisE7 (GQ14)

<400> SEQUENCE: 17
ggaggaagca aggtgcgcgt gg                                               22

<210> SEQ ID NO 18
<211> LENGTH: 22
<212> TYPE: DNA
<213> ORGANISM: Artificial Sequence
<220> FEATURE:
<223> OTHER INFORMATION: Cis Element CisE7-Rev (GQ14-Rev)

<400> SEQUENCE: 18
ggtgcgcgtg gaacgaagga gg                                               22

<210> SEQ ID NO 19
<211> LENGTH: 30
<212> TYPE: DNA
<213> ORGANISM: Artificial Sequence
<220> FEATURE:
<223> OTHER INFORMATION: Cis Element CisE8 (GQ15)

<400> SEQUENCE: 19
ggtgggcaaa ggatcacgtg gttgaggtgg                                       30

<210> SEQ ID NO 20
<211> LENGTH: 30
<212> TYPE: DNA
<213> ORGANISM: Artificial Sequence
<220> FEATURE:
<223> OTHER INFORMATION: Cis Element CisE8-Rev (GQ15-Rev)

<400> SEQUENCE: 20
ggtggagttg gtgcactagg aaacgggtgg                                       30

<210> SEQ ID NO 21
<211> LENGTH: 22
<212> TYPE: DNA
<213> ORGANISM: Artificial Sequence
```

```
<220> FEATURE:
<223> OTHER INFORMATION: Cis Element CisE9 (GQ16)

<400> SEQUENCE: 21
ggcataagga cgacagcagg gg                                              22

<210> SEQ ID NO 22
<211> LENGTH: 22
<212> TYPE: DNA
<213> ORGANISM: Artificial Sequence
<220> FEATURE:
<223> OTHER INFORMATION: Cis Element CisE9-Rev (GQ16-Rev))

<400> SEQUENCE: 22
ggggacgaca gcaggaatac gg                                              22

<210> SEQ ID NO 23
<211> LENGTH: 30
<212> TYPE: DNA
<213> ORGANISM: Artificial Sequence
<220> FEATURE:
<223> OTHER INFORMATION: Cis Element CisE10 (GQ17)

<400> SEQUENCE: 23
ggggcaacct cggacgagca gtcttccagg                                      30

<210> SEQ ID NO 24
<211> LENGTH: 30
<212> TYPE: DNA
<213> ORGANISM: Artificial Sequence
<220> FEATURE:
<223> OTHER INFORMATION: Cis Element CisE10-Rev (GQ17-Rev)

<400> SEQUENCE: 24
ggaccttctg acgagcaggc tccaacgggg                                      30

<210> SEQ ID NO 25
<211> LENGTH: 29
<212> TYPE: DNA
<213> ORGANISM: Artificial Sequence
<220> FEATURE:
<223> OTHER INFORMATION: Cis element CisE11 (GQ18)

<400> SEQUENCE: 25
ggttcttgaa cctctgggcc tggttgagg                                       29

<210> SEQ ID NO 26
<211> LENGTH: 29
<212> TYPE: DNA
<213> ORGANISM: Artificial Sequence
<220> FEATURE:
<223> OTHER INFORMATION: Cis Element CisE11-Rev (GQ18-Rev)

<400> SEQUENCE: 26
ggagttggtc cgggtctcca agttcttgg                                       29

<210> SEQ ID NO 27
<211> LENGTH: 23
<212> TYPE: DNA
<213> ORGANISM: Artificial Sequence
<220> FEATURE:
<223> OTHER INFORMATION: Cis Element CisE12 (GQ19)

<400> SEQUENCE: 27
ggctccggga aaaagaggc cgg                                              23
```

```
<210> SEQ ID NO 28
<211> LENGTH: 23
<212> TYPE: DNA
<213> ORGANISM: Artificial Sequence
<220> FEATURE:
<223> OTHER INFORMATION: Cis element CisE12-Rev (GQ19-Rev)

<400> SEQUENCE: 28
ggccggagaa aaagggcct cgg                                              23

<210> SEQ ID NO 29
<211> LENGTH: 17
<212> TYPE: DNA
<213> ORGANISM: Artificial Sequence
<220> FEATURE:
<223> OTHER INFORMATION: Cis Element CisE13 (GQ20)

<400> SEQUENCE: 29
ggaaccggaa aggcggg                                                    17

<210> SEQ ID NO 30
<211> LENGTH: 17
<212> TYPE: DNA
<213> ORGANISM: Artificial Sequence
<220> FEATURE:
<223> OTHER INFORMATION: Cis Element CisE13-Rev (GQ20-Rev)

<400> SEQUENCE: 30
gggcggaaag gccaagg                                                    17

<210> SEQ ID NO 31
<211> LENGTH: 29
<212> TYPE: DNA
<213> ORGANISM: Artificial Sequence
<220> FEATURE:
<223> OTHER INFORMATION: CisElement CisE14 (GQ22)

<400> SEQUENCE: 31
gggcgccgac ggagtgggta attcctcgg                                       29

<210> SEQ ID NO 32
<211> LENGTH: 29
<212> TYPE: DNA
<213> ORGANISM: Artificial Sequence
<220> FEATURE:
<223> OTHER INFORMATION: Cis Element CisE14-Rev (GQ22-Rev)

<400> SEQUENCE: 32
ggctccttaa tgggtgaggc agccgcggg                                       29

<210> SEQ ID NO 33
<211> LENGTH: 27
<212> TYPE: DNA
<213> ORGANISM: Artificial Sequence
<220> FEATURE:
<223> OTHER INFORMATION: Cis Element CisE15 (GQ23)

<400> SEQUENCE: 33
ggaccagtct aggaactggc ttcctgg                                         27

<210> SEQ ID NO 34
<211> LENGTH: 27
<212> TYPE: DNA
<213> ORGANISM: Artificial Sequence
<220> FEATURE:
<223> OTHER INFORMATION: Cis Element CisE15-Rev (GQ23-Rev)
```

-continued

```
<400> SEQUENCE: 34
ggtccttcgg tcaaggatct gaccagg                                          27

<210> SEQ ID NO 35
<211> LENGTH: 23
<212> TYPE: DNA
<213> ORGANISM: Artificial Sequence
<220> FEATURE:
<223> OTHER INFORMATION: Cis Element CisE16 (GQ24)

<400> SEQUENCE: 35
ggtgaatccg gcccggcca tgg                                               23

<210> SEQ ID NO 36
<211> LENGTH: 23
<212> TYPE: DNA
<213> ORGANISM: Artificial Sequence
<220> FEATURE:
<223> OTHER INFORMATION: Cis Element CisE16-Rev (GQ24-Rev)

<400> SEQUENCE: 36
ggtaccggcc cgggcctaag tgg                                              23

<210> SEQ ID NO 37
<211> LENGTH: 34
<212> TYPE: DNA
<213> ORGANISM: Artificial Sequence
<220> FEATURE:
<223> OTHER INFORMATION: Cis Element CisE17 (c-Myc)

<400> SEQUENCE: 37
atggggaggg tggggagggt ggggaaggtg ggga                                  34

<210> SEQ ID NO 38
<211> LENGTH: 34
<212> TYPE: DNA
<213> ORGANISM: Artificial Sequence
<220> FEATURE:
<223> OTHER INFORMATION: Cis Element CisE17-Rev (c-Myc-Rev)

<400> SEQUENCE: 38
aggggtggaa ggggtgggag gggtgggagg ggta                                  34

<210> SEQ ID NO 39
<211> LENGTH: 17
<212> TYPE: DNA
<213> ORGANISM: Artificial Sequence
<220> FEATURE:
<223> OTHER INFORMATION: Cis Element CisE18 (Chicken Beta-Actin)

<400> SEQUENCE: 39 ggggggggggg gggcggg                                                    17

<210> SEQ ID NO 40
<211> LENGTH: 17
<212> TYPE: DNA
<213> ORGANISM: Artificial Sequence
<220> FEATURE:
<223> OTHER INFORMATION: Cis Element CisE18-Rev (Chicken Beta-Actin-Rev)

<400> SEQUENCE: 40 gggcggggggg gggggg                                                     17

<210> SEQ ID NO 41
```

```
<211> LENGTH: 31
<212> TYPE: DNA
<213> ORGANISM: Artificial Sequence
<220> FEATURE:
<223> OTHER INFORMATION: Cis Element CisE19 (VEGF)

<400> SEQUENCE: 41
ggggcgggcc gggggcgggg tcccggggcg g                                      31

<210> SEQ ID NO 42
<211> LENGTH: 31
<212> TYPE: DNA
<213> ORGANISM: Artificial Sequence
<220> FEATURE:
<223> OTHER INFORMATION: Cis Element CisE19-Rev (VEGF-Rev)

<400> SEQUENCE: 42
ggcggggccc tggggcgggg gccgggcggg g                                      31

<210> SEQ ID NO 43
<211> LENGTH: 39
<212> TYPE: DNA
<213> ORGANISM: Artificial Sequence
<220> FEATURE:
<223> OTHER INFORMATION: Cis Element CisE20 (BCL-2)

<400> SEQUENCE: 43
aggggcgggc gcgggaggaa gggggcggga gcggggctg                              39

<210> SEQ ID NO 44
<211> LENGTH: 39
<212> TYPE: DNA
<213> ORGANISM: Artificial Sequence
<220> FEATURE:
<223> OTHER INFORMATION: Cis Element CisE20-Rev (BCL-2-Rev)

<400> SEQUENCE: 44
gtcggggcga gggcggggga aggagggcgc gggcgggga                              39

<210> SEQ ID NO 45
<211> LENGTH: 432
<212> TYPE: DNA
<213> ORGANISM: Artificial Sequence
<220> FEATURE:
<223> OTHER INFORMATION: Cis Element CisE21 (P5)

<400> SEQUENCE: 45
ggtcctgtat tagaggtcac gtgagtgttt tgcgacattt tgcgacacca tgtggtcacg        60
ctgggtattt aagcccgagt gagcacgcag ggtctccatt ttgaagcggg aggtttgaac       120
gcgcagccgc catgccgggg ttttacgaga ttgtgattaa ggtccccagc gaccttgacg       180
agcatctgcc cggcatttct gacagctttg tgaactgggt ggccgagaag gaatgggagt       240
tgccgccaga ttctgacatg gatctgaatc tgattgagca ggcacccctg accgtggccg       300
agaagctgca gcgcgacttt ctgacggaat ggcgccgtgt gagtaaggcc ccggaggccc       360
ttttctttgt gcaatttgag aagggagaga gctacttcca catgcacgtg ctcgtggaaa       420
ccaccggggt ga                                                          432

<210> SEQ ID NO 46
<211> LENGTH: 432
<212> TYPE: DNA
<213> ORGANISM: Artificial Sequence
<220> FEATURE:
<223> OTHER INFORMATION: Cis Element CisE21-Rev (P5-Rev)
```

<400> SEQUENCE: 46

```
agtggggcca ccaaaggtgc tcgtgcacgt acaccttcat cgagagaggg aagagtttaa    60
cgtgtttctt ttcccggagg ccccggaatg agtgtgccgc ggtaaggcag tctttcagcg   120
cgacgtcgaa gagccggtgc cagtccccac ggacgagtta gtctaagtct aggtacagtc   180
ttagaccgcc gttgagggta aggaagagcc ggtgggtcaa gtgtttcgac agtctttacg   240
gcccgtctac gagcagttcc agcgacccct ggaattagtg ttagagcatt ttggggccgt   300
accgccgacg cgcaagtttg gagggcgaag ttttacctct gggacgcacg agtgagcccg   360
aatttatggg tcgcactggt gtaccacagc gttttacagc gttttgtgag tgcactggag   420
attatgtcct gg                                                       432
```

<210> SEQ ID NO 47
<211> LENGTH: 180
<212> TYPE: DNA
<213> ORGANISM: Artificial Sequence
<220> FEATURE:
<223> OTHER INFORMATION: Cis Element CisE22 (P19)

<400> SEQUENCE: 47

```
gtcacaaaga ccagaaatgg cgccggaggc gggaacaagg tggtggatga gtgctacatc    60
cccaattact tgctccccaa aacccagcct gagctccagt gggcgtggac taatatggaa   120
cagtatttaa gcgcctgttt gaatctcacg gagcgtaaac ggttggtggc gcagcatctg   180
```

<210> SEQ ID NO 48
<211> LENGTH: 180
<212> TYPE: DNA
<213> ORGANISM: Artificial Sequence
<220> FEATURE:
<223> OTHER INFORMATION: Cis Element CisE22-Rev (P19-Rev)

<400> SEQUENCE: 48

```
gtctacgacg cggtggttgg caaatgcgag gcactctaag tttgtccgcg aatttatgac    60
aaggtataat caggtgcggg tgacctcgag tccgacccaa aaccctcgt tcattaaccc    120
ctacatcgtg agtaggtggt ggaacaaggg cggaggccgc ggtaaagacc agaaacactg   180
```

<210> SEQ ID NO 49
<211> LENGTH: 360
<212> TYPE: DNA
<213> ORGANISM: Artificial Sequence
<220> FEATURE:
<223> OTHER INFORMATION: Cis Element CisE23 (P40)

<400> SEQUENCE: 49

```
gtcacaaaga ccagaaatgg cgccggaggt caccaagcag gaagtcaaag acttttccg    60
gtgggcaaag gatcacgtgg ttgaggtgga gcatgaattc tacgtcaaaa agggtggagc   120
caagaaaaga cccgccccca gtgacgcaga tataagtgag cccaaacggg tgcgcgagtc   180
agttgcgcag ccatcgacgt cagacgcggc gggaacaagg tggtggatga gtgctacatc   240
cccaattact tgctccccaa aacccagcct gagctccagt gggcgtggac taatatggaa   300
cagtatttaa gcgcctgttt gaatctcacg gagcgtaaac ggttggtggc gcagcatctg   360
```

<210> SEQ ID NO 50
<211> LENGTH: 360
<212> TYPE: DNA
<213> ORGANISM: Artificial Sequence
<220> FEATURE:

<223> OTHER INFORMATION: Cis Element CisE23-Rev (P40-Rev)

<400> SEQUENCE: 50

| | | |
|---|---|---|
| gtctacgacg cggtggttgg caaatgcgag gcactctaag tttgtccgcg aatttatgac | 60 | |
| aaggtataat caggtgcggg tgacctcgag tccgacccaa aaccctcgt tcattaaccc | 120 | |
| ctacatcgtg agtaggtggt ggaacaaggg cggcgcagac tgcagctacc gacgcgttga | 180 | |
| ctgagcgcgt gggcaaaccc gagtgaatat agacgcagtg accccgccc agaaaagaac | 240 | |
| cgaggtggga aaaactgcat cttaagtacg aggtggagtt ggtgcactag gaaacgggtg | 300 | |
| gccttttca gaaactgaag gacgaaccac tggaggccgc ggtaaagacc agaaacactg | 360 | |

<210> SEQ ID NO 51
<211> LENGTH: 123
<212> TYPE: DNA
<213> ORGANISM: Artificial Sequence
<220> FEATURE:
<223> OTHER INFORMATION: Cis Element CisE24 (P5(209-331))

<400> SEQUENCE: 51

| | | |
|---|---|---|
| cgtgagtgtt ttgcgacatt ttgcgacacc atgtggtcac gctgggtatt taagcccgag | 60 | |
| tgagcacgca gggtctccat tttgaagcgg gaggtttgaa cgcgcagccg ccatgccggg | 120 | |
| gtt | 123 | |

<210> SEQ ID NO 52
<211> LENGTH: 123
<212> TYPE: DNA
<213> ORGANISM: Artificial Sequence
<220> FEATURE:
<223> OTHER INFORMATION: Cis Element CisE24-Rev (P5(209-331)-Rev)

<400> SEQUENCE: 52

| | | |
|---|---|---|
| ttggggccgt accgccgacg cgcaagtttg gagggcgaag ttttacctct gggacgcacg | 60 | |
| agtgagcccg aatttatggg tcgcactggt gtaccacagc gttttacagc gttttgtgag | 120 | |
| tgc | 123 | |

<210> SEQ ID NO 53
<211> LENGTH: 115
<212> TYPE: DNA
<213> ORGANISM: Artificial Sequence
<220> FEATURE:
<223> OTHER INFORMATION: Cis Element CisE25 (P5(317-431))

<400> SEQUENCE: 53

| | | |
|---|---|---|
| cgccatgccg gggttttacg agattgtgat taaggtcccc agcgaccttg acgagcatct | 60 | |
| gcccggcatt tctgacagct ttgtgaactg ggtggccgag aaggaatggg agttg | 115 | |

<210> SEQ ID NO 54
<211> LENGTH: 115
<212> TYPE: DNA
<213> ORGANISM: Artificial Sequence
<220> FEATURE:
<223> OTHER INFORMATION: Cis Element CisE25-Rev (P5(317-431)-Rev)

<400> SEQUENCE: 54

| | | |
|---|---|---|
| gttgagggta aggaagagcc ggtgggtcaa gtgtttcgac agtctttacg gcccgtctac | 60 |
| gagcagttcc agcgacccct ggaattagtg ttagagcatt ttggggccgt accgc | 115 |

<210> SEQ ID NO 55
<211> LENGTH: 138

```
<212> TYPE: DNA
<213> ORGANISM: Artificial Sequence
<220> FEATURE:
<223> OTHER INFORMATION: Cis Element CisE26 (P5(406-543))

<400> SEQUENCE: 55
gggtggccga aaggaatgg gagttgccgc cagattctga catggatctg aatctgattg      60
agcaggcacc cctgaccgtg gccgagaagc tgcagcgcga ctttctgacg gaatggcgcc     120
gtgtgagtaa ggccccgg                                                   138

<210> SEQ ID NO 56
<211> LENGTH: 138
<212> TYPE: DNA
<213> ORGANISM: Artificial Sequence
<220> FEATURE:
<223> OTHER INFORMATION: Cis Element CisE26-Rev (P5(406-543)-Rev)

<400> SEQUENCE: 56
ggccccggaa tgagtgtgcc gcggtaaggc agtctttcag cgcgacgtcg aagagccggt      60
gccagtcccc acggacgagt tagtctaagt ctaggtacag tcttagaccg ccgttgaggg     120
taaggaagag ccggtggg                                                   138

<210> SEQ ID NO 57
<211> LENGTH: 368
<212> TYPE: DNA
<213> ORGANISM: Artificial Sequence
<220> FEATURE:
<223> OTHER INFORMATION: Cis Element CisE27 (P143)

<400> SEQUENCE: 57
cgttgaaaac caaattgact ccggtcacta cgtttccaa ttttctaaag aatcctttac       60
acacaatgtc aggcggcaag tttagcgcca tcacattctc gtacgtgtac gcccacaatt     120
catcgtgatc caaaatttcg ttttttagccg actgagtcaa atatatcatg tagtgtatgc    180
caaaataata gcccaacgat acgcacaatt tggtatcgtc aaagtcaaac caatgattgc     240
aggccctatt aaaacactat ttctcttgtt ttttgtaagg ctcacatcgc ttcaaagctt     300
cattcaaagc ttctttgtcg caggcaaata atgattcaca caaagttcc aaaaacagtt     360 tgatgtcg                                                              368

<210> SEQ ID NO 58
<211> LENGTH: 368
<212> TYPE: DNA
<213> ORGANISM: Artificial Sequence
<220> FEATURE:
<223> OTHER INFORMATION: Cis Element CisE27-Rev (P143-Rev)

<400> SEQUENCE: 58
gctgtagttt gacaaaaacc ttgaaaacac acttagtaat aaacggacgc tgtttcttcg      60
aaacttactt cgaaacttcg ctacactcgg aatgtttttt gttctctttt atcacaaatt     120
atcccggacg ttagtaacca aactgaaact gctatggttt aacacgcata gcaacccgat     180
aataaaaccg tatgtgatgt actatataaa ctgagtcagc cgattttgc tttaaaacct     240 agtgctactt aacacccgca tgtgcatgct cttacactac cgcgatttga acggcggact     300
gtaacacaca tttcctaaga aatcttttaa ccttttgcat cactggcctc agttaaacca    360
aaagttgc                                                              368

<210> SEQ ID NO 59
```

```
<211> LENGTH: 580
<212> TYPE: DNA
<213> ORGANISM: Artificial Sequence
<220> FEATURE:
<223> OTHER INFORMATION: Cis Element CisE28 (CMV)

<400> SEQUENCE: 59
gacattgatt attgactagt tattaatagt aatcaattac ggggtcatta gttcatagcc    60
catatatgga gttccgcgtt acataactta cggtaaatgg cccgcctggc tgaccgccca   120
acgacccccg cccattgacg tcaataatga cgtatgttcc catagtaacg ccaatagggg   180
ctttccattg acgtcaatgg gtggagtatt tacggtaaac tgcccacttg gcagtacatc   240
aagtgtatca tatgccaagt acgcccccta ttgacgtcaa tgacggtaaa tggcccgcct   300
ggcattatgc ccagtacatg accttatggg actttcctac ttggcagtac atctacgtat   360
tagtcatcgc tattaccatg gtgatgcggt tttggcagta catcaatggg cgtggatagc   420
ggtttgactc acggggattt ccaagtctcc accccattga cgtcaatggg agtttgtttt   480
ggcaccaaaa tcaacgggac tttccaaaat gtcgtaacaa ctccgcccca ttgacgcaaa   540
tgggcggtag gcgtgtacgg tgggaggtct atataagcag                         580

<210> SEQ ID NO 60
<211> LENGTH: 580
<212> TYPE: DNA
<213> ORGANISM: Artificial Sequence
<220> FEATURE:
<223> OTHER INFORMATION: Cis Element CisE28-Rev (CMV-Rev)

<400> SEQUENCE: 60
gacgaatata tctggagggt ggcatgtgcg gatggcgggt aaacgcagtt accccgcctc    60
aacaatgctg taaaacccttt cagggcaact aaaaccacgg ttttgtttga ggtaactgc   120
agttacccca cctctgaacc tttaggggca ctcagtttgg cgataggtgc gggtaactac   180
atgacggttt tggcgtagtg gtaccattat cgctactgat tatgcatcta catgacggtt   240
catcctttca gggtattcca gtacatgacc cgtattacgg tccgcccggt aaatggcagt   300
aactgcagtt atccccccgca tgaaccgtat actatgtgaa ctacatgacg gttcacccgt   360
caaatggcat ttatgaggtg ggtaactgca gttacctttc agggataacc gcaatgatac   420
ccttgtatgc agtaataact gcagttaccc gccccagca acccgccagt cggtccgccc   480
ggtaaatggc attcaataca ttgcgccttg aggtatatac ccgatacttg attactgggg   540
cattaactaa tgataattat tgatcagtta ttagttacag                         580

<210> SEQ ID NO 61
<211> LENGTH: 330
<212> TYPE: DNA
<213> ORGANISM: Artificial Sequence
<220> FEATURE:
<223> OTHER INFORMATION: Cis Element CisE29 (SV40)

<400> SEQUENCE: 61
gtgtgtcagt tagggtgtgg aaagtcccca ggctccccag caggcagaag tatgcaaagc    60
atgcatctca attagtcagc aaccaggtgt ggaaagtccc caggctcccc agcaggcaga   120
agtatgcaaa gcatgcatct caattagtca gcaaccatag tcccgcccct aactccgccc   180
atcccgcccc taactccgcc cagttccgcc cattctccgc cccatggctg actaattttt   240
tttatttatg cagaggccga ggccgcctcg gcctctgagc tattccagaa gtagtgagga   300
ggcttttttg gaggcctagg cttttgcaaa                                    330
```

<210> SEQ ID NO 62
<211> LENGTH: 330
<212> TYPE: DNA
<213> ORGANISM: Artificial Sequence
<220> FEATURE:
<223> OTHER INFORMATION: Cis Element CisE29-Rev (SV40-Rev)

<400> SEQUENCE: 62

```
aaacgttttc ggatccggag gttttttcgg aggagtgatg aagaccttat cgagtctccg      60
gctccgccgg agccggagac gtatttattt ttttaatca gtcggtaccc cgcctcttac     120
ccgccttgac ccgcctcaat ccccgccta cccgcctcaa tccccgccct gataccaacg     180
actgattaac tctacgtacg aaacgtatga agacggacga cccctcggac ccctgaaagg     240
tgtggaccaa cgactgatta actctacgta cgaaacgtat gaagacggac gaccctcgg     300
accctgaaa ggtgtgggat tgactgtgtg                                       330
```

<210> SEQ ID NO 63
<211> LENGTH: 263
<212> TYPE: DNA
<213> ORGANISM: Artificial Sequence
<220> FEATURE:
<223> OTHER INFORMATION: Cis Element CisE30 (RLTR)

<400> SEQUENCE: 63

```
gcatcaggcg ccgtgcggta tttcacaccg catatggatc catgcatgtt cgaatttaaa      60
tttaattaac atcatcaata atataccta ttttggattg aagccaatat gataatgagg     120
gggtggagtt tgtgacgtgg cgcggggcgt gggaacgggg cgggtgacgt aggttttagg     180
gcggagtaac ttgtatgtgt tgggaattgt agttttctta aatgggaag tgacgtaacg     240
tgggaatccg gaggcgcccc tgc                                            263
```

<210> SEQ ID NO 64
<211> LENGTH: 263
<212> TYPE: DNA
<213> ORGANISM: Artificial Sequence
<220> FEATURE:
<223> OTHER INFORMATION: Cis Element CisE30-Rev (RLTR-Rev)

<400> SEQUENCE: 64

```
cgtccccgcg gaggcctaag ggtgcaatgc agtgaagggt aaaattcttt tgatgttaag      60
ggttgtgtat gttcaatgag gcgggatttt ggatgcagtg ggcggggcaa gggtgcgggg    120
cgcggtgcag tgtttgaggt gggggagtaa tagtataacc gaagttaggt tttattccat    180
ataataacta ctacaattaa tttaaattta agcttgtacg tacctaggta tacgccacac    240
tttatggcgt gccgcggact acg                                            263
```

<210> SEQ ID NO 65
<211> LENGTH: 360
<212> TYPE: DNA
<213> ORGANISM: Artificial Sequence
<220> FEATURE:
<223> OTHER INFORMATION: Cis Element CisE31 (GQ4-7)

<400> SEQUENCE: 65

```
gggtggccga aaggaatgg gagttgccgc cagattctga catggatctg aatctgattg      60
agcaggcacc cctgaccgtg gccgagaagc tgcagcgcga ctttctgacg gaatggcgcc    120
gtgtgagtaa ggccccggag gccctttct ttgtgcaatt tgagaaggga gagagctact    180
```
tccacatgca cgtgctcgtg gaaaccaccg gggtgaaatc catggttttg ggacgtttcc    240
tgagtcagat tcgcgaaaaa ctgattcaga gaatttaccg cgggatcgag ccgactttgc    300
caaactggtt cgcggtcaca aagaccagaa atggcgccgg aggcgggaac aaggtggtgg    360

<210> SEQ ID NO 66
<211> LENGTH: 360
<212> TYPE: DNA
<213> ORGANISM: Artificial Sequence
<220> FEATURE:
<223> OTHER INFORMATION: Cis Element CisE31-Rev (GQ4-7-Rev)

<400> SEQUENCE: 66
ggtggtggaa caagggcgga ggccgcggta aagaccagaa acactggcgc ttggtcaaac     60
cgtttcagcc gagctagggc gccatttaag agacttagtc aaaaagcgct tagactgagt    120
cctttgcagg gttttggtac ctaaagtggg gccaccaaag gtgctcgtgc acgtacacct    180
tcatcgagag agggaagagt ttaacgtgtt tcttttcccg gaggcccgg aatgagtgtg     240 ccgcggtaag gcagtctttc agcgcgacgt cgaagagccg gtgccagtcc ccacggacga    300
gttagtctaa gtctaggtac agtcttagac cgccgttgag ggtaaggaag agccggtggg    360

<210> SEQ ID NO 67
<211> LENGTH: 322
<212> TYPE: DNA
<213> ORGANISM: Artificial Sequence
<220> FEATURE:
<223> OTHER INFORMATION: Cis Element CisE32 (GQ9-12)

<400> SEQUENCE: 67
ggtcgggtgg ctcgtggaca aggggattac ctcggagaag cagtggatcc aggaggacca     60
ggcctcatac atctccttca atgcggcctc caactcgcgg tcccaaatca aggctgcctt    120
ggacaatgcg ggaaagatta tgagcctgac taaaaccgcc cccgactacc tggtgggcca    180
gcagcccgtg gaggacattt ccagcaatcg gatttataaa attttggaac taaacgggta    240
cgatccccaa tatgcggctt ccgtctttct gggatgggcc acgaaaaagt tcggcaagag    300
gaacaccatc tggctgtttg gg                                             322

<210> SEQ ID NO 68
<211> LENGTH: 322
<212> TYPE: DNA
<213> ORGANISM: Artificial Sequence
<220> FEATURE:
<223> OTHER INFORMATION: Cis Element CisE32-Rev (GQ9-12-Rev)

<400> SEQUENCE: 68
gggtttgtcg gtctaccaca aggagaacgg cttgaaaaag caccgggtag ggtctttctg     60
ccttcggcgt ataaccccta gcatgggcaa atcaaggttt taaaatattt aggctaacga    120
cctttacagg aggtgcccga cgaccgggtg gtccatcagc cccgccaaa atcagtccga     180 gtattagaaa gggcgtaaca ggttccgtcg gaactaaacc ctggcgctca acctccggcg    240
taacttcctc tacatactcc ggaccaggag gacctaggtg acgaagaggc tccattaggg    300
gaacaggtgc tcggtgggct gg                                             322

<210> SEQ ID NO 69
<211> LENGTH: 259
<212> TYPE: DNA
<213> ORGANISM: Artificial Sequence
<220> FEATURE:
<223> OTHER INFORMATION: Cis Element CisE33 (GQ14-15)

<400> SEQUENCE: 69

```
ggaggaagca aggtgcgcgt ggaccagaaa tgcaagtcct cggcccagat agacccgact    60
cccgtgatcg tcacctccaa caccaacatg tgcgccgtga ttgacgggaa ctcaacgacc   120
ttcgaacacc agcagccgtt gcaagaccgg atgttcaaat ttgaactcac ccgccgtctg   180
gatcatgact ttgggaaggt caccaagcag gaagtcaaag acttttttccg gtgggcaaag  240
gatcacgtgg ttgaggtgg                                                259
```

<210> SEQ ID NO 70
<211> LENGTH: 259
<212> TYPE: DNA
<213> ORGANISM: Artificial Sequence
<220> FEATURE:
<223> OTHER INFORMATION: Cis Element CisE33-Rev (GQ14-15-Rev)

<400> SEQUENCE: 70

```
ggtggagttg gtgcactagg aaacgggtgg ccttttttcag aaactgaagg acgaaccact   60
ggaagggttt cagtactagg tctgccgccc actcaagttt aaacttgtag gccagaacgt  120
tgccgacgac cacaagcttc cagcaactca agggcagtta gtgccgcgtg tacaaccaca  180
acctccactg ctagtgccct cagcccagat agacccggct cctgaacgta aagaccaggt  240
gcgcgtggaa cgaaggagg                                                259
```

<210> SEQ ID NO 71
<211> LENGTH: 567
<212> TYPE: DNA
<213> ORGANISM: Artificial Sequence
<220> FEATURE:
<223> OTHER INFORMATION: Cis Element CisE34 (GQ16-22)

<400> SEQUENCE: 71

```
ggcataagga cgacagcagg ggtcttgtgc ttcctgggta caagtacctc ggacccttca    60
acggactcga caagggagag ccggtcaacg aggcagacgc cgcggccctc gagcacgaca   120
aagcctacga ccggcagctc gacagcgag acaacccgta cctcaagtac aaccacgccg   180
acgcggagtt tcaggagcgc cttaaagaag atacgtcttt tgggggcaac ctcggacgag   240
cagtcttcca ggcgaaaaag agggttcttg aacctctggg cctggttgag gaacctgtta   300
agacggctcc gggaaaaaag aggccggtag agcactctcc tgtggagcca gactcctcct   360
cgggaaccgg aaaggcgggc cagcagcctg caagaaaaag attgaatttt ggtcagactg   420
gagacgcaga ctcagtacct gaccccagc ctctcggaca gccaccagca gcccctctg    480
gtctgggaac taatacgatg gctacaggca gtggcgcacc aatggcagac aataacgagg   540
gcgccgacgg agtgggtaat tcctcgg                                      567
```

<210> SEQ ID NO 72
<211> LENGTH: 567
<212> TYPE: DNA
<213> ORGANISM: Artificial Sequence
<220> FEATURE:
<223> OTHER INFORMATION: Cis Element CisE34-Rev (GQ16-22-Rev)

<400> SEQUENCE: 72

```
ggctccttaa tgggtgaggc agccgcggga gcaataacag acggtaacca cgcggtgacg    60
gacatcggta gcataatcaa gggtctggtc tcccccgacg accaccgaca ggctctccga   120
cccccagtcc atgactcaga cgcagaggtc agactggttt taagttagaa aaagaacgtc   180
```

```
cgacgaccgg gcggaaaggc caagggctcc tcctcagacc gaggtgtcct ctcacgagat    240
ggccggagaa aaaagggcct cggcagaatt gtccaaggag ttggtccggg tctccaagtt    300
cttgggagaa aaagcggacc ttctgacgag caggctccaa cgggggtttt ctgcatagaa    360
gaaattccgc gaggactttg aggcgcagcc gcaccaacat gaactccatg cccaacagag    420
gcgacagctc gacggccagc atccgaaaca gcacgagctc ccggcgccgc agacggagca    480
actggccgag agggaacagc tcaggcaact tcccaggctc catgaacatg ggtccttcgt    540
gttctgggga cgacagcagg aatacgg                                        567

<210> SEQ ID NO 73
<211> LENGTH: 225
<212> TYPE: DNA
<213> ORGANISM: Artificial Sequence
<220> FEATURE:
<223> OTHER INFORMATION: Cis Element CisE35 (GQ23-25)

<400> SEQUENCE: 73
ggaccagtct aggaactggc ttcctggacc ctgttaccgc cagcagcgag tatcaaagac     60
atctgcggat aacaacaaca gtgaatactc gtggactgga gctaccaagt accacctcaa    120
tggcagagac tctctggtga atccgggccc ggccatggca agccacaagg acgatgaaga    180 aaagttttt cctcagagcg gggttctcat ctttgggaag caagg                     225

<210> SEQ ID NO 74
<211> LENGTH: 225
<212> TYPE: DNA
<213> ORGANISM: Artificial Sequence
<220> FEATURE:
<223> OTHER INFORMATION: Cis Element CisE35-Rev (GQ23-25-Rev)

<400> SEQUENCE: 74
ggaacgaagg gtttctactc ttggggcgag actccttttt tgaaaagaag tagcaggaac     60
accgaacggt accggcccgg gcctaagtgg tctctcagag acggtaactc caccatgaac    120
catcgaggtc aggtgctcat aagtgacaac aacaataggc gtctacagaa actatgagcg    180
acgaccgcca ttgtcccagg tccttcggtc aaggatctga ccagg                    225
```

RECOMBINANTLY-MODIFIED ADENO-ASSOCIATED VIRUS (rAAV) HAVING IMPROVED PACKAGING EFFICIENCY

FIELD OF THE INVENTION

The present invention is directed to recombinantly-modified adeno-associated virus (rAAV) having improved packaging efficiency, pharmaceutical compositions comprising such rAAV, and methods for their production and use. The present invention is particularly directed to recombinantly-modified adeno-associated virus (rAAV) that have been further modified to comprise Cis-Elements, including replication origins, promoters and enhancers, that are capable of regulating the replication of an rAAV genome and that improve rAAV replication. Preferably, such Cis-Elements are provided within domains of the rAAV that precede and/or follow the 5' and/or 3' inverted terminal repeated sequences (ITR) of an rAAV. The invention particularly concerns the presence and the use of polynucleotide Cis-Elements that comprise actual or potential G-Quadruplex Sequences, polynucleotide Cis-Elements that comprise DNA sequences from wild-type AAV (wt AAV) and polynucleotide Cis-Elements that comprise DNA sequences from other viral genomes or from the human genome.

REFERENCE TO SEQUENCE LISTING

This application includes one or more Sequence Listings pursuant to 37 C.F.R. 1.821 et seq., which are disclosed in computer-readable media (file name: 2650-0003US_ST25.txt, created on Jul. 15, 2019, and having a size of 63,309 bytes), which file is herein incorporated by reference in its entirety.

BACKGROUND OF THE INVENTION

I. Adeno-Associated Virus (AAV)

Adeno-Associated Virus (AAV) is a small, naturally-occurring, non-pathogenic virus belonging to the *Dependovirus* genus of the Parvoviridae (Balakrishnan, B. et al. (2014) "*Basic Biology of Adeno-Associated Virus (AAV) Vectors Used in Gene Therapy*," Curr. Gene Ther. 14(2): 86-100; Zinn, E. et al. (2014) "*Adeno-Associated Virus: Fit To Serve*," Curr. Opin. Virol. 0: 90-97). Despite not causing disease, AAV is known to be able to infect humans and other primates and is prevalent in human populations (Johnson, F. B. et al. (1972) "*Immunological Reactivity of Antisera Prepared Against the Sodium Dodecyl Sulfate-Treated Structural Polypeptides of Adenovirus-Associated Virus*," J. Virol. 9(6): 1017-1026). AAV infect a broad range of different cell types (e.g., cells of the central nervous system, heart, kidney, liver, lung, pancreas, retinal pigment epithelium or photoreceptor cells, or skeletal muscle cells). Twelve serotypes of the virus (e.g., AAV2, AAV5, AAV6, etc.), exhibiting different tissue infection capabilities ("tropisms"), have been identified (Colella, P. et al. (2018) "*Emerging Issues in AAV-Mediated In Vivo Gene Therapy*," Molec. Ther. Meth. Clin. Develop. 8: 87-104; Hocquemiller, M. et al. (2016) "*Adeno-Associated Virus-Based Gene Therapy for CNS Diseases*," Hum. Gene Ther. 27(7): 478-496; Lisowski, L. et al. (2015) "*Adeno-Associated Virus Serotypes For Gene Therapeutics,*" 24: 59-67).

AAV is a single-stranded DNA virus that is composed of approximately 4,700 nucleotides. The viral genome may be described as having a 5' half and a 3' half which together comprise the genes that encode the virus' proteins (FIG. 1). The 5' half of the AAV genome comprises the AAV rep gene, which, through the use of multiple reading frames, staggered initiating promoters (p5, p19 and p40) and alternate splicing, encodes four non-structural Rep proteins (Rep40, Rep52, Rep68 and Rep78) that are required for viral transcription control and replication and for the packaging of viral genomes into the viral capsule (Lackner, D. F. et al. (2002) "*Studies of the Mechanism of Transactivation of the Adeno-Associated Virus p19 Promoter by Rep Protein*," J. Virol. 76(16): 8225-8235). The 3' half the AAV genome comprises the AAV capsid gene (cap), which encodes three capsid proteins (VP): VP1, VP2 and VP3. The three capsid proteins are translated from a single mRNA transcript that is controlled by a single promoter (p40 in case of AAV2). The 3' half of the AAV genome also comprises the AAP gene, which encodes the AAV assembly-activating protein (AAP). Sixty VP monomers (comprising approximately 5 copies of VP1, 5 copies of VP2, and 50 copies of VP3) self-assemble around the AAV genome to form the icosahedral protein shell (capsid) of the mature viral particle (Büning, H. et al. (2019) "*Capsid Modifications for Targeting and Improving the Efficacy of AAV Vectors*," Mol. Ther. Meth. Clin. Devel. 12: P248-P265; Van Vliet K. M. et al. (2008) *The Role of the Adeno-Associated Virus Capsid in Gene Transfer*. In: DRUG DELIVERY SYSTEMS, Jain, K. K. (eds.), Meth. Molec. Biol. 437: 51-91). The AAV AAP protein is believed to be required for stabilizing and transporting newly produced VP proteins from the cytoplasm into the cell nucleus. The 3' half of the AAV genome also comprises the AAV X gene, which is believed to encode a protein that supports genome replication (Colella, P. et al. (2018) "*Emerging Issues in AAV-Mediated In Vivo Gene Therapy*," Molec. Ther. Meth. Clin. Develop. 8: 87-104; Büning, H. et al. (2019) "*Capsid Modifications for Targeting and Improving the Efficacy of AAV Vectors*," Mol. Ther. Meth. Clin. Devel. 12: P248-P265; Cao, M. et al. (2014) "*The X Gene Of Adeno-Associated Virus 2 (AAV2) Is Involved In Viral DNA Replication*," PLoS ONE 9, e104596: 1-10).

The above-described AAV gene-coding sequences are flanked by two AAV-specific palindromic inverted terminal repeated sequences (ITR) of 145 nucleotides (Balakrishnan, B. et al. (2014) "*Basic Biology of Adeno-Associated Virus (AAV) Vectors Used in Gene Therapy*," Curr. Gene Ther. 14(2): 86-100; Colella, P. et al. (2018) "*Emerging Issues in AAV-Mediated In Vivo Gene Therapy*," Molec. Ther. Meth. Clin. Develop. 8: 87-104).

AAV is an inherently defective virus, lacking the capacity to perform at least two critical functions: the ability to initiate the synthesis of viral-specific products and the ability to assemble such products to form the icosahedral protein shell (capsid) of the mature infectious viral particle. It thus requires a co-infecting "helper" virus, such as adenovirus (Ad), herpes simplex virus (HSV), cytomegalovirus (CMV), vaccinia virus or human papillomavirus to provide the viral-associated (VA) RNA that is not encoded by the genes of the AAV genome. Such VA RNA is not translated, but plays a role in regulating the translation of other viral genes. Similarly, the AAV genome does not include genes that encode the viral proteins E1a, E1b, E2a, and E4 of Ad; thus, these proteins must also be provided by a co-infecting "helper" virus. The E1a protein greatly stimulate viral gene transcription during the productive infection. The E1b protein block apoptosis in adenovirus-infected cells, and thus allow productive infection to proceed. The E2a protein plays a role in the elongation phase of viral strand displacement replication by unwinding the template and enhancing the initiation of transcription. The E4 protein has been shown to affect transgene persistence, vector toxicity and immunogenicity (see, Grieger, J. C. et al. (2012) "*Adeno-Associated Virus Vectorology, Manufacturing, and Clinical Applications*," Meth. Enzymol. 507: 229-254; Dyson, N. et al. (1992) "*Adenovirus E1A Targets Key Regulators Of Cell Proliferation*," Canc. Surv. 12: 161-195; Jones N. C. (1990) "*Transformation By The Human Adenoviruses*," Semin. Cancer Biol. 1(6): 425-435; Ben-Israel, H. et al. (2002) "*Adenovirus and Cell Cycle Control*," Front. Biosci. 7: d1369-d1395; Hoeben, R. C. et al. (2013) "*Adenovirus DNA Replication*," Cold Spring Harb. Perspect. Biol. 5: a013003 (pages 1-11); Berk, A. J. (2013) "*Adenoviridae: The Viruses And Their Replication*, In: FIELDS VIROLOGY, 6$^{th}$ Edition (Knipe, D. M. et al., Eds.), Vol. 2, Lippincott Williams & Wilkins, Philadelphia, pages 1704-1731; Weitzman, M. D. (2005) "*Functions Of The Adenovirus E4 Proteins And Their Impact On Viral Vectors*," Front. Biosci. 10: 1106-1117).

AAV viruses infect both dividing and non-dividing cells, and persist as circular episomal molecules or can be integrated into the DNA of a host cell at specific chromosomic loci (Adeno-Associated Virus Integration Sites or AAVS) (Duan, D. (2016) "*Systemic Delivery Of Adeno-Associated Viral Vectors*," Curr. Opin. Virol. 21: 16-25; Grieger, J. C. et al. (2012) "*Adeno-Associated Virus Vectorology, Manufacturing, and Clinical Applications*," Meth. Enzymol. 507: 229-254). AAV remains latent in such infected cells unless a helper virus is present to provide the functions needed for AAV replication and maturation.

II. rAAV and Their Use in Gene Therapy

In light of AAV's properties, recombinantly-modified versions of AAV (rAAV) have found substantial utility as vectors for gene therapy (see, Naso, M. F. et al. (2017) "*Adeno-Associated Virus (AAV) as a Vector for Gene Therapy*," BioDrugs 31: 317-334; Berns, K. I. et al. (2017) "*AAV: An Overview of Unanswered Questions*," Human Gene Ther. 28(4): 308-313; Berry, G. E. et al. (2016) "*Cellular Transduction Mechanisms Of Adeno-Associated Viral Vectors*," Curr. Opin. Virol. 21: 54-60; Blessing, D. et al. (2016) "*Adeno-Associated Virus And Lentivirus Vectors: A Refined Toolkit For The Central Nervous System,*" 21: 61-66; Santiago-Ortiz, J. L. (2016) "*Adeno-Associated Virus (AAV) Vectors in Cancer Gene Therapy*," J. Control Release 240: 287-301; Salganik, M. et al. (2015) "*Adeno-Associated Virus As A Mammalian DNA Vector*," Microbiol. Spectr. 3(4): 1-32; Hocquemiller, M. et al. (2016) "*Adeno-Associated Virus-Based Gene Therapy for CNS Diseases*," Hum. Gene Ther. 27(7): 478-496; Lykken, E. A. et al. (2018) "*Recent Progress And Considerations For AAV Gene Therapies Targeting The Central Nervous System*," J. Neurodevelop. Dis. 10: 16: 1-10; Büning, H. et al. (2019) "*Capsid Modifications for Targeting and Improving the Efficacy of AAV Vectors*," Mol. Ther. Meth. Clin. Devel. 12: P248-P265; During, M. J. et al. (1998) "*In Vivo Expression Of Therapeutic Human Genes For Dopamine Production In The Caudates Of MPTP-Treated Monkeys Using An AAV Vector*," Gene The. 5: 820-827; Grieger, J. C. et al. (2012) "*Adeno-Associated Virus Vectorology, Manufacturing, and Clinical Applications*," Meth. Enzymol. 507: 229-254; Kotterman, M. A. et al. (2014) "*Engineering Adeno-Associated Viruses For Clinical Gene Therapy*," Nat. Rev. Genet. 15(7): 445-451; Kwon, I. et al. (2007) "*Designer Gene Delivery Vectors: Molecular Engineering and Evolution of Adenol-Associated Viral Vectors for Enhanced Gene Transfer*," Pharm. Res. 25(3): 489-499).

rAAV are typically produced using circular plasmids ("rAAV plasmid vector"). The AAV rep and cap genes are typically deleted from such constructs and replaced with a promoter, a β-globin intron, a cloning site into which a therapeutic gene of choice (transgene) has been inserted, and a poly-adenylation ("polyA") site. The inverted terminal repeated sequences (ITR) of the rAAV are, however, retained, so that the transgene expression cassette of the rAAV plasmid vector is flanked by AAV ITR sequences (Colella, P. et al. (2018) "*Emerging Issues in AAV-Mediated In Vivo Gene Therapy*," Molec. Ther. Meth. Clin. Develop. 8: 87-104; Büning, H. et al. (2019) "*Capsid Modifications for Targeting and Improving the Efficacy of AAV Vectors*," Mol. Ther. Meth. Clin. Devel. 12: P248-P265). Thus, in the 5' to 3' direction, the rAAV comprises a 5' ITR, the transgene expression cassette of the rAAV, and a 3' ITR.

rAAV have been used to deliver a transgene to patients suffering from any of a multitude of genetic diseases (e.g., hereditary lipoprotein lipase deficiency (LPLD), Leber's congenital amaurosis (LCA), aromatic L-amino acid decarboxylase deficiency (AADC), choroideremia and hemophilia), and have utility in new clinical modalities, such as in interfering RNA (RNAi) therapy and gene-modifying strategies such as Crispr/Cas9 (U.S. Pat Nos. 8,697,359, 10,000,772, 10,113,167, 10,227,611; Lino, C. A. et al. (2018) "*Delivering CRISPR: A Review Of The Challenges And Approaches*," Drug Deliv. 25(1): 1234-1237; Ferreira, V. et al. (2014) "*Immune Responses To AAV-Vectors, The Glybera Example From Bench To Bedside*" Front. Immunol. 5(82): 1-15), Büning, H. et al. (2019) "*Capsid Modifications for Targeting and Improving the Efficacy of AAV Vectors*," Mol. Ther. Meth. Clin. Devel. 12: P248-P265; Rastall, D. P. W. (2017) "*Current and Future Treatments for Lysosomal Storage Disorders*," Curr. Treat Options Neurol. 19(12): 45; Kay, M. et al. (2017) "*Future Of rAAV Gene Therapy: Platform For RNA Gene Editing And Beyond*," Human Gene Ther. 28: 361-372); Berns, K. I. et al. (2017) "*AAV: An Overview of Unanswered Questions*," Human Gene Ther. 28(4): 308-313). More than 150 clinical trials involving rAAV have been instituted (Büning, H. et al. (2019) "*Capsid Modifications for Targeting and Improving the Efficacy of AAV Vectors*," Mol. Ther. Meth. Clin. Devel. 12: P248-P265; Clément, N. et al. (2016) "*Manufacturing Of Recombinant Adeno-Associated Viral Vectors For Clinical Trials*," Meth. Clin. Develop. 3: 16002: 1-7). The most commonly used AAV serotype for such recombinantly-modified AAV is AAV2, which is capable of infecting cells of the central nervous system, kidney, retinal pigment epithelium and photoreceptor cells. AAV serotype is AAV9, which infects muscle cells, also has been widely used (Duan, D. (2016) "*Systemic Delivery Of Adeno-Associated Viral Vectors*," Curr. Opin. Virol. 21: 16-25). AAV serotypes are described in U.S. Pat. No. 10,301,650; 10,266,846; 10,265,417; 10,214,785; 10,214,566; 10,202,657; 10,046,016; 9,884, 071; 9,856,539; 9,737,618; 9,677,089; 9,458,517; 9,457, 103; 9,441,244; 9,193,956; 8,846,389; 8,507,267; 7,906, 111; 7,479,554; 7,186,552; 7,105,345; 6,984,517; 6,962, 815; and 6,733,757.

III. Methods of rAAV Production rAAV containing a desired transgene expression cassette are typically produced by human cells (such as HEK293) grown in suspension. Since, as described above, rAAV are defective viruses, additional functions must be provided in order to replicate and package rAAV.

Typically, rAAV are produced by transiently transfecting cells with an rAAV plasmid vector and a second plasmid vector that comprises an AAV helper function-providing polynucleotide that provides the Rep52 and Rep78 genes that are required for vector transcription control and replication, and for the packaging of viral genomes into the viral capsule (Rep40 and Rep68 are not required for rAAV production) and the cap genes that were excised from the AAV in order to produce the rAAV. The second plasmid vector may additionally comprise a non-AAV helper function-providing polynucleotide that encodes the viral transcription and translation factors (E1a, E1b, E2a, VA and E4) required for AAV proliferation, so as to comprise, in concert with the rAAV, a double plasmid transfection system (Grimm, D. et al. (1998) "*Novel Tools For Production And Purification Of Recombinant Adeno-Associated Virus Vectors*," Hum. Gene Ther. 9: 2745-2760; Penaud-Budloo, M. et al. (2018) "*Pharmacology of Recombinant Adeno-associated Virus Production*," Molec. Ther. Meth. Clin. Develop. 8: 166-180).

However, it has become increasingly common to clone the AAV helper function-providing polynucleotide (which provides the required rep and cap genes) into an "AAV helper plasmid," and to clone the non-AAV helper function-providing polynucleotide (which provides the genes that encode the viral transcription and translation factors) on a different plasmid (i.e., an "Ad helper plasmid"), so that such plasmids, in concert with an rAAV plasmid vector, comprise a triple plasmid transfection system (FIG. 2). Use of the triple plasmid transfection system has the advantage of permitting one to easily switch one cap gene for another, thereby facilitating changes in the rAAV's serotype. The use of helper plasmids, rather than helper viruses, permits rAAV to be produced without additionally producing particles of the helper virus (François, A. et al. (2018) "*Accurate Titration of Infectious AAV Particles Requires Measurement of Biologically Active Vector Genomes and Suitable Controls*," Molec. Ther. Meth. Clin. Develop. 10: 223-236; Matsushita, T. et al. (1998) "*Adeno-Associated Virus Vectors Can Be Efficiently Produced Without Helper Virus*," Gene Ther. 5: 938-945).

The transient transfection of plasmid DNAs comprising the rAAV plasmid vector, the AAV rep and cap genes, and the trans-acting AAD helper genes into HEK293 cells by calcium phosphate coprecipitation has become the standard method to produce rAAV in the research laboratory (Grimm, D. et al. (1998) "*Novel Tools For Production And Purification Of Recombinant Adeno-Associated Virus Vectors*," Hum. Gene Ther. 9: 2745-2760). However, the use of such a calcium phosphate-mediated transfection process with suspension-cultured transfected mammalian cells requires media exchanges, and is thus not considered ideal for the large-scale rAAV production that is required in order to produce therapeutic doses of rAAV (Lock, M. et al. (2010) "*Rapid, Simple, and Versatile Manufacturing of Recombinant-Adeno-Associated Viral Vectors at Scale*," Hum. Gene Ther. 21: 1259-1271). For this reason, polyethylenimine (PEI), has been used as a transfection reagent and has been found to provide yields of virus that are similar to those obtained using calcium phosphate-mediated transfection (Durocher, Y. et al. (2007) "*Scalable Serum-Free Production Of Recombinant Adeno-Associated Virus Type 2 By Transfection Of 293 Suspension Cells*," J. Virol. Meth. 144: 32-40).

rAAV may alternatively be produced in insect cells (e.g., sf9 cells) using baculoviral vectors (see, e.g., U.S. Pat. Nos. 9,879,282; 9,879,279; 8,945,918; 8,163,543; 7,271,002 and 6,723,551), or in HSV-infected baby hamster kidney (BHK) cells (e.g., BHK21 (François, A. et al. (2018) "*Accurate Titration of Infectious AAV Particles Requires Measurement of Biologically Active Vector Genomes and Suitable Controls*," Molec. Ther. Meth. Clin. Develop. 10: 223-236). Methods of rAAV production are reviewed in Grieger, J. C. et al. (2012) "*Adeno-Associated Virus Vectorology, Manufacturing, and Clinical Applications*," Meth. Enzymol. 507: 229-254, and in Penaud-Budloo, M. et al. (2018) "*Pharmacology of Recombinant Adeno-associated Virus Production*," Molec. Ther. Meth. Clin. Develop. 8: 166-180.

IV. Methods of rAAV Purification and Recovery

After production, rAAV are typically collected and purified by one or more overnight CsCl gradient centrifugations (Zolotukhin, S. et al. (1999) "*Recombinant Adeno-Associated Virus Purification Using Novel Methods Improves Infectious Titer And Yield*," Gene Ther. 6: 973-985), followed by desalting to form a purified rAAV production stock. Titers of $10^{12}$-$10^{13}$ infectious rAAV capsids/mL are obtainable.

Because rAAV infection does not cause a cytopathic effect, plaque assays cannot be used to determine the infectious titer of an rAAV preparation. Infectious titer is thus typically measured as the median tissue culture infective dose (TCID50). In this method, a HeLa-derived AAV2 rep- and cap-expressing cell line is grown in a 96-well plate and infected with replicate 10-fold serial dilutions of the rAAV preparation, in the presence of adenovirus of serotype 5. After infection, vector genome replication is determined by quantitative PCR (qPCR) (Zen, Z. et al. (2004) "*Infectious Titer Assay For Adeno-Associated Virus Vectors With Sensitivity Sufficient To Detect Single Infectious Events*," Hum. Gene Ther. 15: 709-715). Alternatively, the infectious titer of an rAAV preparation can be measured using the infectious center assay (ICA). This assay uses HeLa rep-cap cells and Ad, but, after incubation, involves transferring the cells to a membrane. A labeled probe that is complementary to a portion of the employed transgene is used to detect infectious centers (representing individual infected cells) via hybridization. Although more widely used, the TCID50 assay has been reported to lead to a higher background than the ICA and to overestimate vector infectivity relative to the ICA (François, A. et al. (2018) "*Accurate Titration of Infectious AAV Particles Requires Measurement of Biologically Active Vector Genomes and Suitable Controls*," Molec. Ther. Meth. Clin. Develop. 10: 223-236). Methods of producing and purifying rAAV are described inter alia in U.S. Pat. Nos. 10,294,452; 10,161,011; 10,017,746; 9,598,703; 7,625,570; 7,439,065; 7,419,817; 7,208,315; 6,995,006; 6,989,264; 6,846,665 and 6,841,357.

V. G-Quadruplex Sequences and Structures

DNA can form several secondary structures besides the classic double helix; one that has received much attention in recent years is the G-Quadruplex Structure. G-Quadruplex Structures are formed from the stacking of three planar "G-tetrad" (also known as "guanine quartet") structures. Each G-tetrad is formed through Hoogsteen base pairing via hydrogen bond interactions involving four deoxyguanosine residues. The planar structure of the G-tetrad may be stabilized by cations (e.g., Na$^+$). In the G-tetrad structure shown below, the guanines are attached to their respective polynucleotide chain(s) via "R".

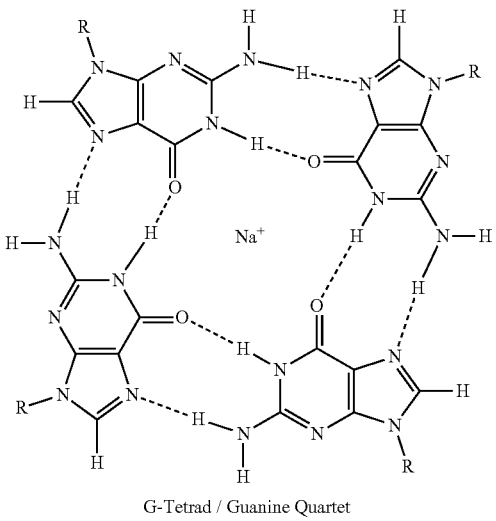

G-Tetrad / Guanine Quartet

The stacking of G-tetrad structures to form a G-Quadruplex Structure is accomplished by the spontaneous interaction and/or looping of domains of one, two or four polynucleotide chains that together comprise a G-Quadruplex Sequence (FIGS. 3A-3D).

G-Quadruplex Structures are well known in the art (Bedrat, A. et al. (2016) "*Re-evaluation of G-Quadruplex propensity with G4Hunter*," Nucleic Acids Res. 44(4): 1746-1759; Harris, L. M. et al. (2015) "*G-Quadruplexes In Pathogens: A Common Route To Virulence Control?*" PLoS Pathog. 11(2): e1004562 (pages 1-15); Siddiqui-Jain, A. et al. (2002) "*Direct Evidence For A G-Quadruplex In A Promoter Region And Its Targeting With A Small Molecule To Repress c-MYC Transcription*," Proc. Natl. Acad. Sci. (U.S.A.) 99: 11593-11598; Wieland, M. et al. (2007) "*RNA Quadruplex-Based Modulation Of Gene Expression*," Chem. Biol., 14: 757-763; Millevoi, S. et al. (2012) "*G-Quadruplexes In RNA Biology*," Wiley interdiscip. Rev. RNA 3: 495-507; Lopes, J. et al. (2011) "*G-Quadruplex-Induced Instability During Leading-Strand Replication*," EMBO J. 30: 4033-4046; Paeschke, K. et al. (2011) "*DNA Replication Through G-Quadruplex Motifs Is Promoted By The Saccharomyces cerevisiae Pif1 DNA Helicase*," Cell 145: 678-691; Besnard, E. et al. (2012) "*Unraveling Cell Type-Specific And Reprogrammable Human Replication Origin Signatures Associated With G-Quadruplex Consensus Motifs*," Nat. Struct. Mol. Biol. 19: 837-844; and Valton, A. L. et al. (2014) "*G4 Motifs Affect Origin Positioning And Efficiency In Two Vertebrate Replicators*," EMBO J. 33: 732-746).

Sequences capable of forming G-Quadruplex Structures have been recently identified within the genome of a number of viruses, e.g., HIV, HSV, EBV influenza, papillomavirus and cauliflower mosaic virus (Piekna-Przybylska, D. et al. (2014) "*U3 Region In The HIV-1 Genome Adopts A G-Quadruplex Structure In Its RNA And DNA Sequence*," Biochemistry 53(16): 2581-2593; Artusi, S. et al. (2015) "*The Herpes Simplex Virus-1 Genome Contains Multiple Clusters Of Repeated G-Quadruplex: Implications For The Antiviral Activity Of A G-Quadruplex Ligand*," Antivir. Res. 118: 123-131; Tlučková, K. et al. (2013) "*Human Papillomavirus G-Quadruplexes*," Biochemistry 52(41): 7207-7216; Métifiot, M. et al. (2014) "*G-Quadruplexes In Viruses: Function And Potential Therapeutic Applications*," Nucleic Acids Res. 42(20): 12352-12366).

Viral G-Quadruplex Structures have been proposed to function as steric blocks to DNA replication and transcription (Satkunanathan, S. et al. (2017) "*The Function Of DNA Binding Protein Nucleophosmin In AAV Replication*," Virol. 510: 46-54). For example, the presence of a G-Quadruplex Sequence in the wild-type Nuclease hypersensitive element III (NHE III$_1$) gene, a major regulator of c-MYC transcription, causes that gene to be expressed at a lower level than that of a mutated NHE III$_1$ gene (Siddiqui-Jain, A. et al. (2002) "*Direct Evidence For A G-Quadruplex In A Promoter Region And Its Targeting With A Small Molecule To Repress c-MYC Transcription*," Proc. Natl. Acad. Sci. (U.S.A.) 99: 11593-11598; Harris, L. M. et al. (2015) "*G-Quadruplexes In Pathogens: A Common Route To Virulence Control?*" PLoS Pathog. 11(2): e1004562 (pages 1-15).

It has been proposed that limitations in high titer AAV production may be due to AAV's dependence on helper viruses and on an insufficient understanding of factors, viral or cellular, that contribute to AAV replication (Satkunanathan, S. et al. (2017) "*The Function Of DNA Binding Protein Nucleophosmin In AAV Replication*," Virol. 510: 46-54). In this regard, investigations into the life cycle of AAV have revealed that AAV helper genes function to induce cellular factors that were either missing or inactivated in a normal cell cycle (Muzyczka, N. (1992) "*Use Of Adeno-Associated Virus As A General Transduction Vector For Mammalian Cells*," Curr. Top. Microbiol. Immunol. 158: 97-129; Ni, T. H. et al. (1998) "*Cellular Proteins Required For Adeno-Associated Virus DNA Replication In The Absence Of Adenovirus Coinfection*," J. Virol. 72(4): 2777-2787). Additionally, cellular and viral DNA binding proteins have been found to play a vital role in AAV life cycle in unwinding AAV double-stranded DNA, nicking single-stranded DNA, facilitating single-stranded DNA association with nuclei and ultimately enhancing viral DNA production and protein expression (Weitzman, M. D. (2006) "*The Parvovirus Life Cycle: An Introduction To Molecular Interactions Important For Infection*," In: Kerr, J. R. et al. (Eds.) PARVOVIRUSES, Hodder Arnold, London, UK; Satkunanathan, S. et al. (2017) "*The Function Of DNA Binding Protein Nucleophosmin In AAV Replication*," Virol. 510: 46-54).

For example, Nucleophosmin (NPM1) is a nucleolar protein that plays a role in many diverse functions, such as genome stability, DNA duplication and transcriptional regulation through its ability to bind to single-stranded nucleic acids. Nucleophosmin has been reported to enhance AAV infection by acting as a chaperone protein to mobilize AAV capsids into and out of the nucleolus (Nash, K. et al. (2009) "*Identification Of Cellular Proteins That Interact With The Adeno-Associated Virus Rep Protein*," J. Virol. 83(1): 454-469; Ni, T. H. et al. (1998) "*Cellular Proteins Required For Adeno-Associated Virus DNA Replication In The Absence Of Adenovirus Coinfection*," J. Virol. 72(4): 2777-2787; Nicolas, A. et al. (2012) "*Factors Influencing Helper-Independent Adeno-Associated Virus Replication*," Virology 432(1): 1-9). Nucleophosmin has, however, also been found to negatively regulate DNA replication by binding to G-Quadruplex Sequences (Gallo, A. et al. (2012) "*Structure of Nucleophosmin DNA-binding Domain and Analysis of Its Complex with a G-Quadruplex Sequence from the c-MYC Promoter*," J. Biol. Chem. 287(32): 26539-26548). The down-regulation of Nucleophosmin has been found to result in an increase in AAV2 and AAV8 vector production (Satkunanathan, S. et al. (2017) "*The Function Of DNA Binding*

*Protein Nucleophosmin In AAV Replication*," Virol. 510: 46-54), and the destruction or elimination of G-Quadruplex Sequences has been found to unblock G-Quadruplex Structure-mediated inhibition of viral DNA replication of HIV and HSV (Harris, L. M. et al. (2015) "*G-Quadruplexes In Pathogens: A Common Route To Virulence Control?*" PLoS Pathog. 11(2): e1004562 (pages 1-15)). Thus, the presence of G-Quadruplex Sequences has been reported to inhibit AAV vector production (Satkunanathan, S. et al. (2017) "*The Function Of DNA Binding Protein Nucleophosmin In AAV Replication*," Virol. 510: 46-54).

Despite all such prior advances, a need remains to develop methods capable of addressing problems that presently limit the applicability of rAAV to gene therapy (Grieger, J. C. et al. (2012) "*Adeno-Associated Virus Vectorology, Manufacturing, and Clinical Applications*," Meth. Enzymol. 507: 229-254; Kotterman, M. A. et al. (2014) "*Engineering Adeno-Associated Viruses For Clinical Gene Therapy*," Nat. Rev. Genet. 15(7): 445-451; Kwon, I. et al. (2007) "*Designer Gene Delivery Vectors: Molecular Engineering and Evolution of Adeno-Associated Viral Vectors for Enhanced Gene Transfer*," Pharm. Res. 25(3): 489-499; Naso, M. F. et al. (2017) "*Adeno-Associated Virus (AAV) as a Vector for Gene Therapy*," BioDrugs 31: 317-334).

The present invention is directed to improved methods for increasing the efficiency of AAV and rAAV packaging through regulation of the replication of rAAV genomes.

SUMMARY OF THE INVENTION

The present invention is directed to recombinantly-modified adeno-associated virus (rAAV) having improved packaging efficiency, pharmaceutical compositions comprising such rAAV, and methods for their production and use. The present invention is particularly directed to recombinantly-modified adeno-associated virus (rAAV) that have been further modified to comprise Cis-Elements, including replication origins, promoters and enhancers, that are capable of regulating the replication of an rAAV genome and that improve rAAV replication. Preferably, such Cis-Elements are provided within domains of the rAAV that precede and/or follow the 5' and/or 3' inverted terminal repeated sequences (ITR) of an rAAV. The invention particularly concerns the presence and the use of polynucleotide Cis-Elements that comprise actual or potential G-Quadruplex Sequences, polynucleotide Cis-Elements that comprise DNA sequences from wild-type AAV (wt AAV) and polynucleotide Cis-Elements that comprise DNA sequences from other viral genomes or from the human genome.

In detail, the invention provides a recombinantly-modified adeno-associated virus (rAAV) that comprises a Cis-Element in one or more of its P1, P2, P3 or P4 Domains, wherein:
  (1) the P1 Domain is 5' to a 5' ITR of the rAAV;
  (2) the P2 Domain is 3' to the 5' ITR of the rAAV and 5' to a transgene cassette of the rAAV;
  (3) the P3 Domain is 3' to the transgene cassette of the rAAV and 5' to a 3' ITR of the rAAV; and
  (4) the P4 Domain is 3' to the 3' ITR of the rAAV; and
wherein the presence of the Cis-Element causes rAAV-producing cells to produce the rAAV at a higher production titer than would be attained with such rAAV if lacking the Cis-Element.

The invention also provides a pharmaceutical composition that comprises:

(A) a preparation of recombinantly-modified adeno-associated virus (rAAV) that comprise a Cis-Element in one or more of its P1, P2, P3 or P4 Domains, wherein:
  (1) the P1 Domain is 5' to a 5' ITR of the rAAV;
  (2) the P2 Domain is 3' to the 5' ITR of the rAAV and 5' to a transgene cassette of the rAAV;
  (3) the P3 Domain is 3' to the transgene cassette of the rAAV and 5' to a 3' ITR of the rAAV; and
  (4) the P4 Domain is 3' to the 3' ITR of the rAAV; and
(B) a pharmaceutically acceptable carrier.

The invention also provides a method for increasing the production titer of recombinantly-modified adeno-associated virus (rAAV), wherein the method comprises:

(A) employing, as the rAAV for producing the production titer, an rAAV that has been modified to comprise an added Cis-Element in one or more of its P1, P2, P3 or P4 Domains, wherein:
  (1) the P1 Domain is 5' to a 5' ITR of the rAAV;
  (2) the P2 Domain is 3' to the 5' ITR of the rAAV and 5' to a transgene cassette of the rAAV;
  (3) the P3 Domain is 3' to the transgene cassette of the rAAV and 5' to a 3' ITR of the rAAV; and
  (4) the P4 Domain is 3' to the 3' ITR of the rAAV; and
(B) culturing cells that have been transfected with the employed rAAV, wherein the cells additionally contain an AAV helper function-providing polynucleotide and a non-AAV helper function-providing polynucleotide, and wherein the culturing is conducted in a culture medium under conditions sufficient to permit the production of rAAV; wherein the presence of the Cis-Element in the employed rAAV causes the cells to produce the rAAV at an increased production titer relative to that which would be attained if the employed rAAV had lacked the Cis-Element.

The invention also provides the embodiment of such recombinantly-modified adeno-associated virus (rAAV), pharmaceutical composition, or method, wherein the employed rAAV has been modified to comprise an added Cis-Element in its P1 Domain.

The invention also provides the embodiment of such recombinantly-modified adeno-associated viruses (rAAV), pharmaceutical compositions, or methods, wherein the employed rAAV has been modified to comprise an added Cis-Element in its P2 Domain.

The invention also provides the embodiment of such recombinantly-modified adeno-associated viruses (rAAV), pharmaceutical compositions, or methods, wherein the employed rAAV has been modified to comprise an added Cis-Element in its P3 Domain.

The invention also provides the embodiment of such recombinantly-modified adeno-associated viruses (rAAV), pharmaceutical compositions, or methods, wherein the employed rAAV has been modified to comprise an added Cis-Element in its P4 Domain.

The invention also provides the embodiment of such recombinantly-modified adeno-associated viruses (rAAV), pharmaceutical compositions, or methods, wherein the employed rAAV has been modified to comprise an added Cis-Element in its P1 Domain and in one or more of its P2, P3 or P4 Domain.

The invention also provides the embodiment of such recombinantly-modified adeno-associated viruses (rAAV), pharmaceutical compositions, or methods, wherein the employed rAAV has been modified to comprise an added Cis-Element in its P2 Domain and in one or more of its P3 or P4 Domain.

The invention also provides the embodiment of such recombinantly-modified adeno-associated viruses (rAAV), pharmaceutical compositions, or methods, wherein the employed rAAV has been modified to comprise an added Cis-Element in its P3 Domain and in its P4 Domain.

The invention also provides the embodiment of such recombinantly-modified adeno-associated viruses (rAAV), pharmaceutical compositions, or methods, wherein the added Cis-Element forms a G-Quadruplex Structure in the employed rAAV.

The invention also provides the embodiment of such recombinantly-modified adeno-associated viruses (rAAV), pharmaceutical compositions, or methods, wherein an added Cis-Element is selected from the group consisting of:
(1) a Potential G-Quadruplex Sequence of a wild type AAV genome or a Potential G-Quadruplex Sequence of a wild type AAV genome in a reversed orientation;
(2) an Actual G-Quadruplex Sequence of a wild type AAV genome or an Actual G-Quadruplex Sequence of a wild type AAV genome in a reversed orientation;
(3) a DNA sequence from wild-type AAV or a DNA sequence from wild-type AAV in a reversed orientation; and
(4) a DNA sequence from another viral genome or a DNA sequence from another viral genome in a reversed orientation.

The invention also provides the embodiment of such recombinantly-modified adeno-associated viruses (rAAV), pharmaceutical compositions, or methods, wherein the transgene cassette encodes a protein, or comprises a transcribed nucleic acid, that is therapeutic for a genetic or heritable disease or condition.

The invention also provides the embodiment of such recombinantly-modified adeno-associated viruses (rAAV), pharmaceutical compositions, or methods, wherein the employed rAAV belongs to the rAAV1, rAAV2, rAAV5, rAAV6, rAAV7, rAAV8, rAAV9 or rAAV10 serotype, or to a hybrid of the serotypes.

The invention also provides the embodiment of such recombinantly-modified adeno-associated viruses (rAAV), pharmaceutical compositions, or methods, wherein the employed rAAV belongs to the rAAV2, rAAV5, or rAAV9 serotype, or to a hybrid of the serotypes.

The invention also provides the embodiment of such recombinantly-modified adeno-associated viruses (rAAV), pharmaceutical compositions, or methods, wherein the cells are human embryonic kidney cells, baby hamster kidney cells or sf9 insect cells.

The invention also provides the embodiment of such recombinantly-modified adeno-associated viruses (rAAV), pharmaceutical compositions, or methods, wherein the cells are HEK293 human embryonic kidney cells.

The invention also provides the embodiment of such recombinantly-modified adeno-associated viruses (rAAV), pharmaceutical compositions, or methods, wherein the cells are BHK21 baby hamster kidney cells.

The invention also provides such recombinantly-modified adeno-associated viruses (rAAV) and pharmaceutical compositions, wherein the transgene cassette encodes a protein, or comprises a transcribed nucleic acid, that is therapeutic for a genetic or heritable disease or condition, for use in the treatment of the genetic or heritable disease or condition.

BRIEF DESCRIPTION OF THE DRAWINGS

FIGS. 3A-3D depict such G-tetrad as gray planar rectangles whose vertices are connected to the polynucleotide backbone. The G-Quadruplex Structures may be formed from a single polynucleotide chain (FIGS. 3A-3B), that spontaneously loops back upon itself, from two polynucleotide strands (FIG. 3C) that loop back upon each other, or from four polynucleotide chains (FIG. 3D) that loop back upon each other. The ability of such polynucleotide chains to form such G-tetrads and to form such loops depends upon their presence of G-Quadruplex Sequences; such one, two or four polypeptide chains may form loops in either an anti-parallel manner (e.g., FIG. 3A) or in a parallel manner (e.g., FIG. 3B) (see, Harris, L. M. et al. (2015) "*G-Quadruplexes In Pathogens: A Common Route To Virulence Control?*" PLoS Pathog. 11(2): e1004562 (pages 1-15).

FIG. 9A shows the P2 Domain of the rAAV plasmid vector pAV-TBG-EGFP. FIG. 9B shows the production titers of rAAV obtained using rAAV plasmid vectors containing any of Cis-Elements CisE1-CisE27 (Table 1), relative to that obtained using the parental rAAV plasmid vector, pAV-TBG-EGFP. The production titers of rAAV were obtained using the parental or derivative rAAV plasmids in a triple plasmid transfection system with a helper plasmid providing the AAV rep and cap functions and an Ad helper plasmid that provided the required adenoviral functions.

FIG. 10B shows the production titers of rAAV obtained using rAAV plasmid vectors containing any of Cis-Elements CisE1, CisE20, CisE21, CisE27, CisE28, CisE29, or CisE30 (Table 1), relative to that obtained using the parental rAAV plasmid vector, pAV-TBG-EGFP. The production titers of rAAV were obtained using the parental or derivative rAAV plasmid vectors in a triple plasmid transfection system with an AAV helper plasmid providing the AAV rep and cap functions and an Ad helper plasmid that provided the required adenoviral functions.

FIG. 11B shows the production titers of rAAV obtained using rAAV plasmids containing any of Cis-Elements CisE1, CisE20, or CisE21 (Table 1), relative to that obtained using the parental rAAV plasmid, pAV-TBG-EGFP. The production titers of rAAV were obtained using the parental or derivative rAAV plasmids in a triple plasmid transfection system with an AAV helper plasmid providing the AAV rep and cap functions and an Ad helper plasmid that provided the required adenoviral functions.

FIG. 12B shows the production titers of rAAV obtained using rAAV plasmid vectors containing Cis-Element CisE21 (Table 1) in the forward orientation (SEQ ID NO:41) ("CisE21-For-P1") or in the reverse orientation (SEQ ID NO:42) ("CisE21-Rev-P1"), relative to that obtained using the parental rAAV plasmid vector, pAV-TBG-EGFP. The production titers of rAAV were obtained using the parental or derivative rAAV plasmids in a triple plasmid transfection system with an AAV helper plasmid providing the AAV rep and cap functions and an Ad helper plasmid that provided the required adenoviral functions.

FIG. 13B shows the production titers of rAAV obtained using rAAV plasmid vectors containing different Cis-Elements (Cis-Element CisE21, CisE22, CisE23, CisE24, CisE25, CisE26, CisE28, CisE29, CisE31, CisE32, CisE33, CisE34, or CisE35) within the P1 Domain, while maintaining the same Cis-Element (CisE30-Rev) within the P4 Domain of the rAAV plasmid vector. FIG. 13C shows the production titers of rAAV obtained using rAAV plasmid vectors containing different Cis-Elements (Cis-Element CisE21, CisE22, CisE23, CisE24, CisE25, CisE27, CisE28, CisE32, CisE33, or CisE34) within its P1 Domain and Cis-Element CisE35-Rev within its P4 Domain. FIG. 13D shows the production titers of rAAV obtained using rAAV plasmid vectors containing different Cis-Elements Cis-Element CisE22-Rev, CisE27-Rev, CisE29-Rev, or CisE35-Rev) within the P4 Domain, while maintaining the same Cis-Element (CisE28) within the P1 Domain of the rAAV plasmid vector. The production titers of rAAV were obtained using the parental or derivative rAAV plasmids in a triple plasmid transfection system with an AAV helper plasmid providing the AAV rep and cap functions and an Ad helper plasmid that provided the required adenoviral functions.

DETAILED DESCRIPTION OF THE INVENTION

I. The Methods of the Present Invention

The present invention is directed to recombinantly-modified adeno-associated virus (rAAV) having improved packaging efficiency, pharmaceutical compositions comprising such rAAV, and methods for their production and use. The present invention is particularly directed to recombinantly-modified adeno-associated virus (rAAV) that have been further modified to comprise Cis-Elements, including replication origins, promoters and enhancers, that are capable of regulating the replication of an rAAV genome and that improve rAAV replication. Preferably, such Cis-Elements are provided within domains of the rAAV that precede and/or follow the 5' and/or 3' inverted terminal repeated sequences (ITR) of an rAAV. The invention particularly concerns the presence and the use of polynucleotide Cis-Elements that comprise actual or potential G-Quadruplex Sequences, polynucleotide Cis-Elements that comprise DNA sequences from wild-type AAV (wt AAV) and polynucleotide Cis-Elements that comprise DNA sequences from other viral genomes or from the human genome.

The present invention is based in part on the recognition that high levels of DNA replication increase both the amount of rAAV genomes particles and, consequently, the efficiency of rAAV packaging, and thus result in high production titers of rAAV stocks. Such desired high levels of DNA replication can be attained by modifying rAAV or rAAV plasmid vectors to contain additional polynucleotides that comprise replication origins, promoters, enhancers, etc. Because such polynucleotides act to increase the replication of rAAV vectors on which they are present, they are referred to herein as "Cis-Elements." The invention encompasses recombinant AAV vectors and rAAV plasmid vectors that carry such Cis-Elements and their use in the production of novel stable cell lines capable of generating high titer rAAV preparations. The Cis-Elements of the present invention are preferably introduced into an rAAV plasmid vector. Such introduction is preferably accomplished using well-known methods of recombinant DNA technology.

As used herein, the term "AAV" is intended to denote adeno-associated virus, and may be used to refer to the virus itself or derivatives thereof. The term covers all subtypes and both naturally occurring and recombinant forms. As used herein, the term "rAAV" is intended to denote a recombinantly-modified version of AAV that comprises a polynucleotide sequence not of AAV origin (i.e., a polynucleotide heterologous to AAV). The rAAV may be single-stranded or double-stranded, and may be composed of deoxyribonucleotides or ribonucleotides.

Figure 4:
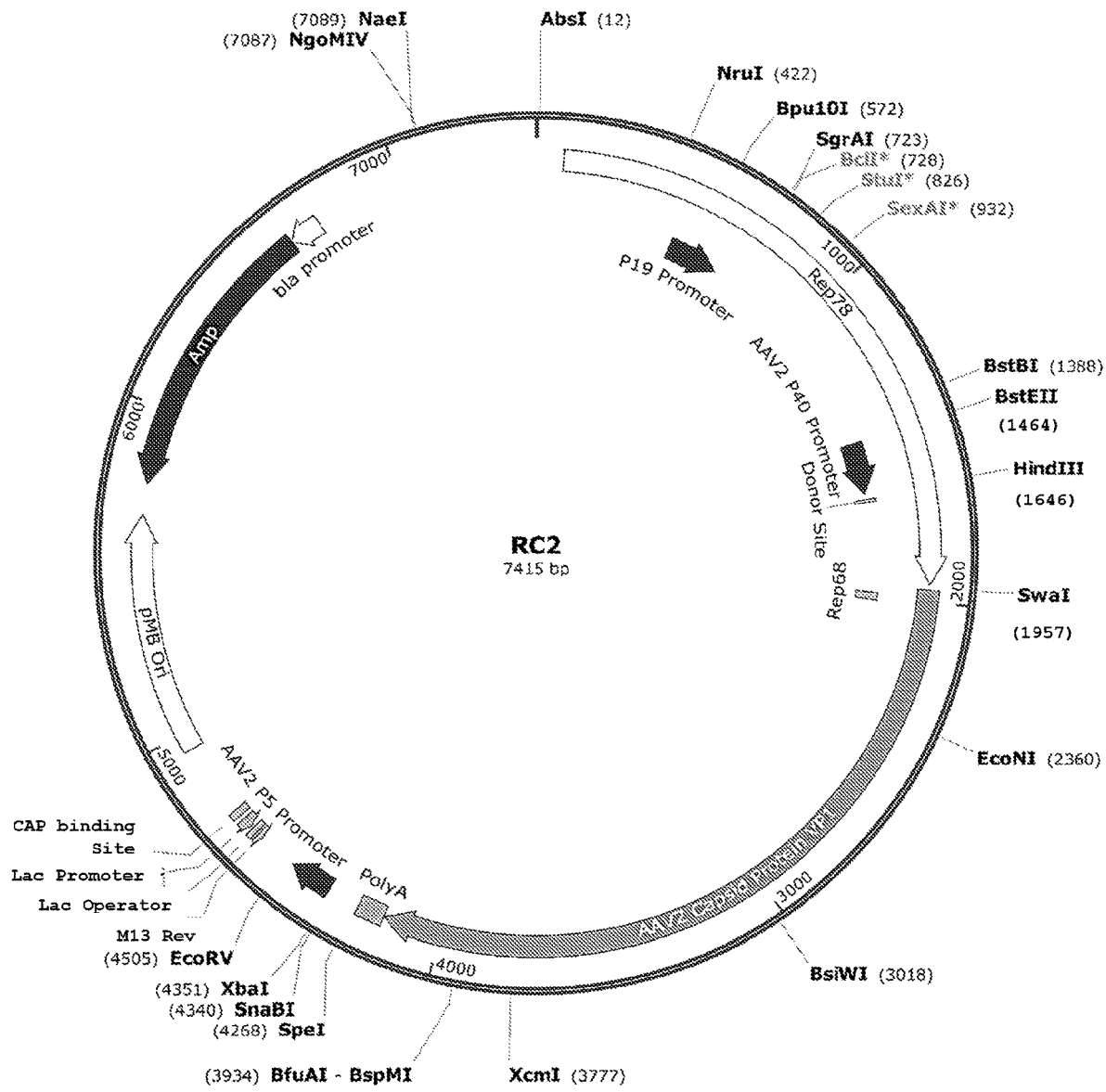
FIG. 4 shows a map of the AAV helper plasmid vector pAAV-RC2.

As used herein, the term "AAV helper functions" denotes AAV proteins (e.g., Rep and Cap) and/or polynucleotides of AAV that are required for the replication and packaging of an rAAV. Such AAV helper functions are provided by an "AAV helper function-providing polynucleotide," which as such term is used herein is a virus, plasmid vector, a non-plasmid vector, or a polynucleotide that has been integrated into a cellular chromosome, that provides AAV helper functions. AAV helper plasmids that may be used in accordance with the present invention to provide AAV helper functions, such as pAAV-RC (Agilent; Addgene; Cell Biolabs), pAAV-RC2 (Cell Biolabs), etc., are commercially available. Plasmid pAAV-RC2 (SEQ ID NO:1; FIG. 4) is an AAV helper plasmid that may be used in accordance with the present invention to provide AAV helper functions.

Coding Strand of Plasmid pAAV-RC2 (SEQ ID NO: 1):
ccgggccccc cctcgaggtc gacggtatcg ggggagctcg cagggtctcc attttgaagc gggaggtttg aacgcgcagc cgccatgccg gggttttacg agattgtgat taaggtcccc agcgaccttg acgagcatct gcccggcatt tctgacagct ttgtgaactg ggtggccgag aaggaatggg agttgccgcc agattctgac atggatctga atctgattga gcaggcaccc ctgaccgtgg ccgagaagct gcagcgcgac tttctgacgg aatggcgccg tgtgagtaag gccccggagg ctcttttctt tgtgcaattt gagaagggag agagctactt ccacatgcac gtgctcgtgg aaaccaccgg ggtgaaatcc atggttttgg gacgtttcct gagtcagatt cgcgaaaaac tgattcagag aatttaccgc gggatcgagc cgactttgcc aaactggttc gcggtcacaa agaccagaaa tggcgccgga ggcgggaaca aggtggtgga tgagtgctac atccccaatt acttgctccc caaaacccag cctgagctcc agtgggcgtg gactaatatg gaacagtatt taagcgcctg tttgaatctc acggagcgta acggttggt ggcgcagcat ctgacgcacg tgtcgcagac gcaggagcag aacaaagaga atcagaatcc caattctgat gcgccggtga tcagatcaaa aacttcagcc aggtacatgg agctggtcgg gtggctcgtg gacaagggga ttacctcgga gaagcagtgg atccaggagg accaggcctc atacatctcc ttcaatgcgg cctccaactc gcggtcccaa atcaaggctg ccttggacaa tgcgggaaag attatgagcc tgactaaaac cgccccccgac tacctggtgg gccagcagcc cgtggaggac atttccagca atcggattta taaaattttg gaactaaacg ggtacgatcc ccaatatgcg gcttccgtct ttctgggatg ggccacgaaa aagttcggca agaggaacac catctggctg tttgggcctg caactaccgg gaagaccaac atcgcggagg ccatagccca cactgtgccc ttctacgggt gcgtaaactg gaccaatgag aactttccct caacgactg tgtcgacaag atggtgatct ggtgggagga ggggaagatg accgccaagg tcgtggagtc ggccaaagcc attctcggag gaagcaaggt gcgcgtggac cagaaatgca agtcctcggc ccagatagac ccgactcccg tgatcgtcac ctccaacacc aacatgtgcg ccgtgattga cgggaactca acgaccttcg aacaccagca gccgttgcaa gaccggatgt tcaaatttga actcaccccgc cgtctggatc atgactttgg gaaggtcacc aagcaggaag tcaaagactt tttccggtgg gcaaaggatc acgtggttga ggtggagcat gaattctacg tcaaaaaggg tggagccaag aaaagacccg cccccagtga cgcagatata agtgagccca aacgggtgcg cgagtcagtt gcgcagccat cgacgtcaga gcggaagct tcgatcaact acgcagacag gtaccaaaac aaatgttctc gtcacgtggg catgaatctg atgctgtttc cctgcagaca atgcgagaga atgaatcaga attcaaatat ctgcttcact cacggacaga aagactgttt agagtgcttt cccgtgtcag aatctcaacc cgtttctgtc gtcaaaaagg cgtatcagaa actgtgctac attcatcata tcatgggaaa ggtgccagac gcttgcactg cctgcgatct ggtcaatgtg gatttggatg actgcatctt tgaacaataa atgatttaaa tcaggtatgg ctgccgatgg ttatcttcca gattggctcg -continued

```
aggacactct ctctgaagga ataagacagt ggtggaagct caaacctggc ccaccaccac caaagcccgc agagcggcat aaggacgaca gcagggggtct tgtgcttcct gggtacaagt acctcggacc cttcaacgga ctcgacaagg gagagccggt caacgaggca gacgccgcgg ccctcgagca cgacaaagcc tacgaccggc agctcgacag cggagacaac ccgtacctca agtacaacca cgccgacgcg gagtttcagg agcgccttaa agaagatacg tcttttgggg gcaacctcgg acgagcagtc ttccaggcga aaaagagggt tcttgaacct ctgggcctgg ttgaggaacc tgttaagacg gctccgggaa aaaagaggcc ggtagagcac tctcctgtgg agccagactc ctcctcggga accggaaagg cgggccagca gcctgcaaga aaaagattga attttggtca gactggagac gcagactcag tacctgaccc ccagcctctc ggacagccac cagcagcccc ctctggtctg ggaactaata cgatggctac aggcagtggc gcaccaatgg cagacaataa cgagggcgcc gacggagtgg gtaattcctc gggaaattgg cattgcgatt ccacatggat gggcgacaga gtcatcacca ccagcacccg aacctgggcc ctgcccacct acaacaacca cctctacaaa caaatttcca gccaatcagg agcctcgaac gacaatcact actttggcta cagcacccct tgggggtatt ttgacttcaa cagattccac tgccactttt caccacgtga ctggcaaaga ctcatcaaca caactgggg attccgaccc aagagactca acttcaagct ctttaacatt caagtcaaag aggtcacgca gaatgacggt acgacgacga ttgccaataa ccttaccagc acggttcagg tgtttactga ctcggagtac cagctcccgt acgtcctcgg ctcggcgcat caaggatgcc tcccgccgtt cccagcagac gtcttcatgg tgccacagta tggatacctc accctgaaca acgggagtca ggcagtagga cgctcttcat tttactgcct ggagtacttt ccttctcaga tgctgcgtac cggaaacaac tttaccttca gctacacttt tgaggacgtt cctttccaca gcagctacgc tcacagccag agtctggacc gtctcatgaa tcctctcatc gaccagtacc tgtattactt gagcagaaca aacactccaa gtggaaccac cacgcagtca aggcttcagt tttctcaggc cggagcgagt gacattcggg accagtctag gaactggctt cctggaccct gttaccgcca gcagcgagta tcaaagacat ctgcggataa caacaacagt gaatactcgt ggactggagc taccaagtac cacctcaatg gcagagactc tctggtgaat ccgggcccgg ccatggcaag ccacaaggac gatgaagaaa agttttttcc tcagagcggg gttctcatct ttgggaagca aggctcagag aaaacaaatg tggacattga aaaggtcatg attacagacg aagaggaaat caggacaacc aatcccgtgg ctacggagca gtatggttct gtatctacca acctccagag aggcaacaga caagcagcta ccgcagatgt caacacacaa ggcgttcttc caggcatggt ctggcaggac agagatgtgt accttcaggg gcccatctgg gcaaagattc cacacacgga cggacatttt caccccctctc ccctcatggg tggattcgga cttaaacacc ctcctccaca gattctcatc aagaacaccc cggtacctgc gaatccttcg accaccttca gtgcggcaaa gtttgcttcc ttcatcacac agtactccac gggacaggtc agcgtggaga tcgagtggga gctgcagaag gaaaacagca acgctggaa
```

-continued

```
tcccgaaatt cagtacactt ccaactacaa caagtctgtt aatgtggact
ttactgtgga cactaatggc gtgtattcag agcctcgccc cattggcacc
agatacctga ctcgtaatct gtaattgctt gttaatcaat aaaccgttta
attcgtttca gttgaacttt ggtctctgcg tatttctttc ttatctagtt
tccatgctct aggatccact agtaacggcc gccagtgtgc tggaattcgg
ctttgtagtt aatgattaac ccgccatgct acttatctac gtagccatgc
tctagaggtc ctgtattaga ggtcacgtga gtgttttgcg acattttgcg
acaccatgtg gtcacgctgg gtatttaagc ccgagtgagc acgcagggtc
tccattttga agcgggaggt ttgaacgcgc agccgccaag ccgaattctg
cagatatcca aacactggcg gccgctcgac tagagcggcc gccaccgcgg
tggagctcca gcttttgttc cctttagtga gggttaattg cgcgcttggc
gtaatcatgg tcatagctgt ttcctgtgtg aaattgttat ccgctcacaa
ttccacacaa catacgagcc ggaagcataa agtgtaaagc ctggggtgcc
taatgagtga gctaactcac attaattgcg ttgcgctcac tgcccgcttt
ccagtcggga aacctgtcgt gccagctgca ttaatgaatc ggccaacgcg
cggggagagg cggtttgcgt attgggcgct cttccgcttc ctcgctcact
gactcgctgc gctcggtcgt tcggctgcgg cgagcggtat cagctcactc
aaaggcggta atacggttat ccacagaatc aggggataac gcaggaaaga
acatgtgagc aaaaggccag caaaaggcca ggaaccgtaa aaaggccgcg
ttgctggcgt ttttccatag gctccgcccc cctgacgagc atcacaaaaa
tcgacgctca agtcagaggt ggcgaaaccc gacaggacta taaagatacc
aggcgtttcc ccctggaagc tccctcgtgc gctctcctgt tccgaccctg
ccgcttaccg gatacctgtc cgcctttctc ccttcgggaa gcgtggcgct
ttctcatagc tcacgctgta ggtatctcag ttcggtgtag gtcgttcgct
ccaagctggg ctgtgtgcac gaaccccccg ttcagcccga ccgctgcgcc
ttatccggta actatcgtct tgagtccaac ccggtaagac acgacttatc
gccactggca gcagccactg gtaacaggat tagcagagcg aggtatgtag
gcggtgctac agagttcttg aagtggtggc ctaactacgg ctacactaga
agaacagtat ttggtatctg cgctctgctg aagccagtta ccttcggaaa
aagagttggt agctcttgat ccggcaaaca aaccaccgct ggtagcggtg
gtttttttgt ttgcaagcag cagattacgc gcagaaaaaa aggatctcaa
gaagatcctt tgatcttttc tacggggtct gacgctcagt ggaacgaaaa
ctcacgttaa gggattttgg tcatgagatt atcaaaaagg atcttcacct
agatcctttt aaattaaaaa tgaagtttta atcaatcta aagtatatat
gagtaaactt ggtctgacag ttaccaatgc ttaatcagtg aggcacctat
ctcagcgatc tgtctatttc gttcatccat agttgcctga ctccccgtcg
tgtagataac tacgatacgg gagggcttac catctggccc cagtgctgca
atgataccgc gagacccacg ctcaccggct ccagatttat cagcaataaa
ccagccagcc ggaagggccg agcgcagaag tggtcctgca actttatccg
cctccatcca gtctattaat tgttgccggg aagctagagt aagtagttcg
```

-continued

```
ccagttaata gtttgcgcaa cgttgttgcc attgctacag gcatcgtggt gtcacgctcg tcgtttggta tggcttcatt cagctccggt tcccaacgat caaggcgagt tacatgatcc cccatgttgt gcaaaaaagc ggttagctcc ttcggtcctc cgatcgttgt cagaagtaag ttggccgcag tgttatcact catggttatg gcagcactgc ataattctct tactgtcatg ccatccgtaa gatgcttttc tgtgactggt gagtactcaa ccaagtcatt ctgagaatag tgtatgcggc gaccgagttg ctcttgcccg gcgtcaatac gggataatac cgcgccacat agcagaactt taaaagtgct catcattgga aaacgttctt cggggcgaaa actctcaagg atcttaccgc tgttgagatc cagttcgatg taacccactc gtgcacccaa ctgatcttca gcatctttta ctttcaccag cgtttctggg tgagcaaaaa caggaaggca aaatgccgca aaaaagggaa taagggcgac acgaaatgt tgaatactca tactcttcct ttttcaatat tattgaagca tttatcaggg ttattgtctc atgagcggat acatatttga atgtatttag aaaaataaac aaatagggt tccgcgcaca tttccccgaa aagtgccacc taaattgtaa gcgttaatat tttgttaaaa ttcgcgttaa attttgtta aatcagctca ttttttaacc aataggccga aatcggcaaa atcccttata aatcaaaga atagaccgag atagggttga gtgttgttcc agtttggaac aagagtccac tattaaagaa cgtggactcc aacgtcaaag ggcgaaaaac cgtctatcag ggcgatggcc cactacgtga accatcaccc taatcaagtt ttttggggtc gaggtgccgt aaagcactaa atcggaaccc taaagggagc ccccgattta gagcttgacg gggaaagccg gcgaacgtgg cgagaaagga agggaagaaa gcgaaaggag cgggcgctag ggcgctggca agtgtagcgg tcacgctgcg cgtaaccacc acacccgccg cgcttaatgc gccgctacag ggcgcgtccc attcgccatt caggctgcgc aactgttggg aagggcgatc ggtgcgggcc tcttcgctat tacgccagct ggcgaaaggg ggatgtgctg caaggcgatt aagttgggta acgccagggt tttcccagtc acgacgttgt aaaacgacgg ccagtgagcg cgcgtaatac gactcactat agggcgaatt gggta
```

In SEQ ID NO:1, residues 85-1950 of pAAV-RC2 encode the Rep protein, Rep78 (with residues 484-663 corresponding to the P19 promoter, residues 1464-1643 corresponding to the P40 promoter and residues 1668-1676 being a donor site); residues 1967-4174 encode the capsid protein, VP1; residues 1992-2016 encodes a portion of the Rep68 protein; residues 4175-4256 encode a polyA sequence; residues 4610-4626 are M13 Rev sequences; residues 4634-4650 are Lac operator sequences; 4658-4688 are Lac promoter sequences; residues 4951-5675 correspond to pMB ori sequences, residues 5771-6631 encode an ampicillin resistance determinant; and residues 6632-6730 are bla promoter sequences (FIG. 4).

Figure 5:
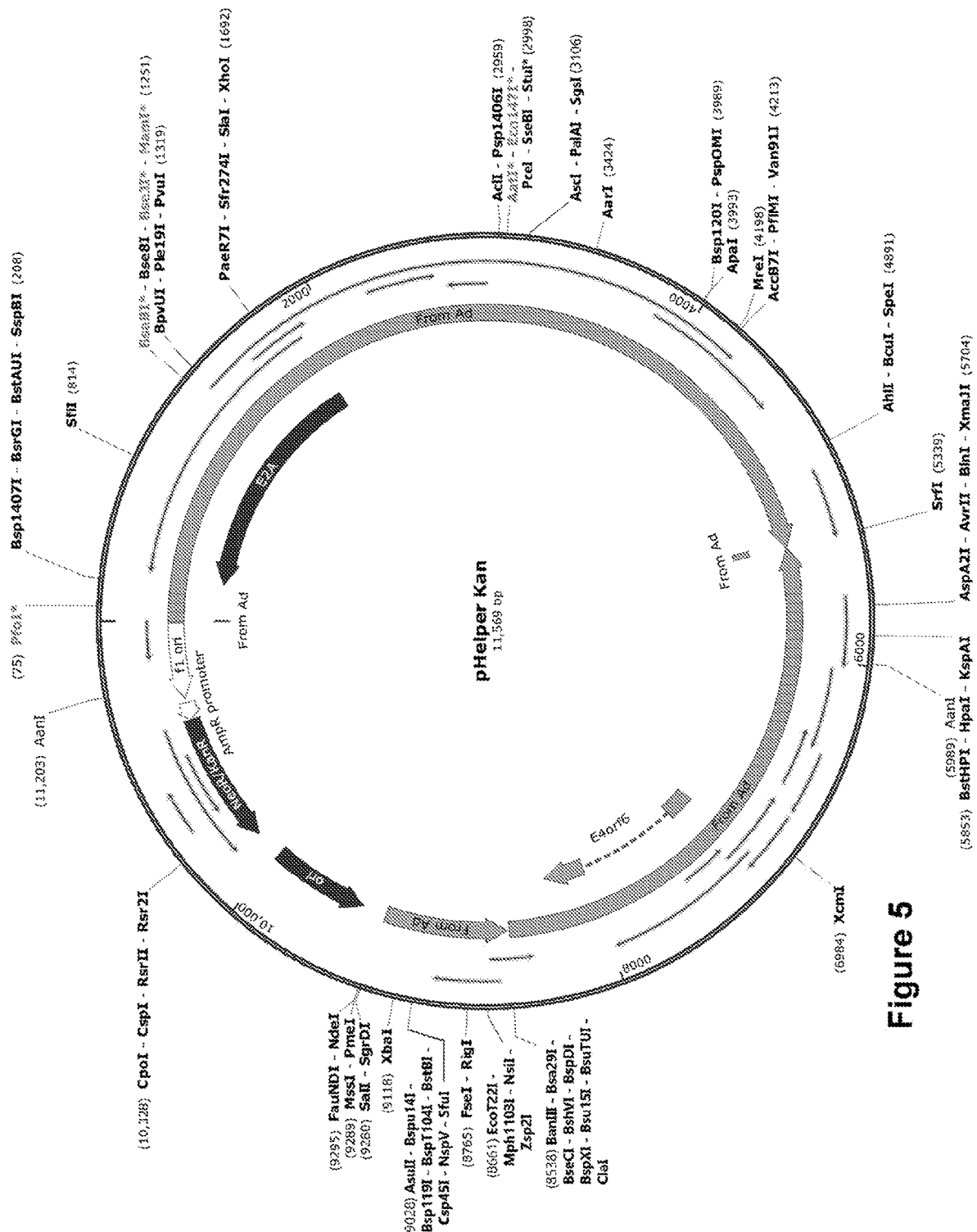
FIG. 5 shows a map of the non-AAV helper plasmid vector pHelper-Kan.

As used herein, the term "non-AAV helper functions" denotes proteins of Ad, CMV, HSV or other non-AAD viruses (e.g., E1a, E1b, E2a, VA and E4) and/or polynucleotides of Ad, CMV, HSV or other non-AAD viruses that are required for the replication and packaging of an rAAV. Such non-AAV helper functions are provided by a "non-AAV helper function-providing polynucleotide," which as such term is used herein is a virus, plasmid vector, a non-plasmid vector, or a polynucleotide that has been integrated into a cellular chromosome, that provides non-AAV helper functions. The vector, pHelper and derivatives thereof (commercially available from Cell Biolabs, Inc., Invitrogen and Stratagene) are suitable non-AAV helper function-providing polynucleotide (see, e.g., Matsushita, T. et al. (1998) "*Adeno-Associated Virus Vectors Can Be Efficiently Produced Without Helper Virus,*" Gene Ther. 5: 938-945; Sharma, A. et al. (2010)"*Transduction Efficiency Of AAV 2/6, 2/8 And 2/9 Vectors For Delivering Genes In Human Corneal Fibroblasts,*" Brain Res. Bull. 81(2-3): 273-278). Plasmid pHelper-Kan (SEQ ID NO:2; FIG. 5) is a non-AAV helper function-providing polynucleotide that may be used in accordance with the present invention to provide non-AAV helper functions.

Coding Strand of Plasmid pHelper-Kan (SEQ ID NO: 2):
ggtacccaac tccatgctta acagtcccca ggtacagccc accctgcgtc gcaaccagga acagctctac agcttcctgg agcgccactc gccctacttc cgcagccaca gtgcgcagat taggagcgcc acttcttttt gtcacttgaa aaacatgtaa aaataatgta ctaggagaca ctttcaataa aggcaaatgt ttttatttgt acactctcgg gtgattattt acccccccacc cttgccgtct gcgccgttta aaatcaaag gggttctgcc gcgcatcgct atgcgccact ggcagggaca cgttgcgata ctggtgttta gtgctccact taaactcagg cacaaccatc cgcggcagct cggtgaagtt ttcactccac aggctgcgca ccatcaccaa cgcgtttagc aggtcgggcg ccgatatctt gaagtcgcag ttggggcctc cgccctgcgc gcgcgagttg cgatacacag ggttgcagca ctggaacact atcagcgccg ggtggtgcac gctggccagc acgctcttgt cggagatcag atccgcgtcc aggtcctccg cgttgctcag ggcgaacgga gtcaactttg gtagctgcct tcccaaaaag ggtgcatgcc caggctttga gttgcactcg caccgtagtg gcatcagaag gtgaccgtgc ccggtctggg cgttaggata cagcgcctgc atgaaagcct tgatctgctt aaaagccacc tgagcctttg cgccttcaga gaagaacatg ccgcaagact tgccggaaaa ctgattggcc ggacaggccg cgtcatgcac gcagcacctt gcgtcggtgt tggagatctg caccacattt cggccccacc ggttcttcac gatcttggcc ttgctagact gctccttcag cgcgcgctgc ccgttttcgc tcgtcacatc catttcaatc acgtgctcct tatttatcat aatgctcccg tgtagacact taagctcgcc ttcgatctca gcgcagcggt gcagccacaa cgcgcagccc gtgggctcgt ggtgcttgta ggttacctct gcaaacgact gcaggtacgc ctgcaggaat cgcccatca tcgtcacaaa ggtcttgttg ctggtgaagg tcagctgcaa cccgcggtgc tcctcgttta gccaggtctt gcatacggcc gccagagctt ccacttggtc aggcagtagc ttgaagtttg cctttagatc gttatccacg tggtacttgt ccatcaacgc gcgcgcagcc tccatgccct tctcccacgc agacacgatc ggcaggctca gcgggtttat caccgtgctt tcactttccg cttcactgga ctcttccttt tcctcttgcg tccgcatacc ccgcgccact gggtcgtctt cattcagccg ccgcaccgtg cgcttacctc ccttgccgtg cttgattagc accggtgggt tgctgaaacc caccatttgt agcgccacat cttctctttc ttcctcgctg tccacgatca cctctgggga tggcgggcgc tcgggcttgg gagagggggcg cttcttttc ttttggacg caatggccaa atccgccgtc gaggtcgatg ccgcgggct gggtgtgcgc ggcaccagcg catcttgtga cgagtcttct tcgtcctcgg actcgagacg ccgcctcagc cgcttttttg ggggcgcgcg gggaggcggc ggcgacggcg acggggacga cacgtcctcc atggttggtg gacgtcgcgc cgcaccgcgt ccgcgctcgg gggtggtttc gcgctgctcc tcttcccgac tggccatttc cttctcctat aggcagaaaa agatcatgga gtcagtcgag aaggaggaca gcctaaccgc cccctttgag ttcgccacca ccgcctccac cgatgccgcc aacgcgccta ccaccttccc cgtcgaggca ccccgcttg aggaggagga

```
agtgattatc gagcaggacc caggttttgt aagcgaagac gacgaggatc
gctcagtacc aacagaggat aaaaagcaag accaggacga cgcagaggca
aacgaggaac aagtcgggcg gggggaccaa aggcatggcg actacctaga
tgtgggagac gacgtgctgt tgaagcatct gcagcgccag tgcgccatta
tctgcgacgc gttgcaagag cgcagcgatg tgcccctcgc catagcggat
gtcagccttg cctacgaacg ccacctgttc tcaccgcgcg tacccccaa
acgccaagaa aacggcacat gcgagcccaa cccgcgcctc aacttctacc
ccgtatttgc cgtgccagag gtgcttgcca cctatcacat cttttccaa
aactgcaaga taccctatc ctgccgtgcc aaccgcagcc gagcggacaa
gcagctggcc ttgcggcagg cgctgtcat acctgatatc gcctcgctcg
acgaagtgcc aaaaatcttt gagggtcttg gacgcgacga gaaacgcgcg
gcaaacgctc tgcaacaaga aaacagcgaa aatgaaagtc actgtggagt
gctggtggaa cttgagggtg acaacgcgcg cctagccgtg ctgaaacgca
gcatcgaggt cacccacttt gcctacccgg cacttaacct accccccaag
gttatgagca cagtcatgag cgagctgatc gtgcgccgtg cacgacccct
ggagagggat gcaaacttgc aagaacaaac cgaggagggc ctacccgcag
ttggcgatga gcagctggcg cgctggcttg agacgcgcga gcctgccgac
ttggaggagc gacgcaagct aatgatggcc gcagtgcttg ttaccgtgga
gcttgagtgc atgcagcggt tctttgctga cccggagatg cagcgcaagc
tagaggaaac gttgcactac acctttcgcc agggctacgt gcgccaggcc
tgcaaaattt ccaacgtgga gctctgcaac ctggtctcct accttggaat
tttgcacgaa aaccgcctcg ggcaaaacgt gcttcattcc acgctcaagg
gcgaggcgcg ccgcgactac gtccgcgact gcgtttactt atttctgtgc
tacacctggc aaacggccat gggcgtgtgg cagcaatgcc tggaggagcg
caacctaaag gagctgcaga gctgctaaa gcaaaacttg aaggacctat
ggacggcctt caacgagcgc tccgtggccg cgcacctggc ggacattatc
ttccccgaac gcctgcttaa aaccctgcaa cagggtctgc cagacttcac
cagtcaaagc atgttgcaaa actttaggaa ctttatccta gagcgttcag
gaattctgcc cgccacctgc tgtgcgcttc ctagcgactt tgtgcccatt
aagtaccgtg aatgccctcc gccgctttgg ggtcactgct accttctgca
gctagccaac taccttgcct accactccga catcatggaa gacgtgagcg
gtgacggcct actggagtgt cactgtcgct gcaacctatg caccccgcac
cgctccctgg tctgcaattc gcaactgctt agcgaaagtc aaattatcgg
tacctttgag ctgcagggtc cctcgcctga cgaaaagtcc gcggctccgg
ggttgaaact cactccgggg ctgtggacgt cggcttacct tcgcaaattt
gtacctgagg actaccacgc ccacgagatt aggttctacg aagaccaatc
ccgcccgcca aatgcggagc ttaccgcctg cgtcattacc cagggccaca
tccttggcca attgcaagcc atcaacaaag cccgccaaga gtttctgcta
cgaaagggac ggggggttta cctggacccc cagtccggcg aggagctcaa
cccaatcccc ccgccgccgc agccctatca gcagccgcgg gcccttgctt
cccaggatgg caccccaaaaa gaagctgcag ctgccgccgc cgccacccac
```

-continued

```
ggacgaggag gaatactggg acagtcaggc agaggaggtt ttggacgagg aggaggagat gatggaagac tgggacagcc tagacgaagc ttccgaggcc gaagaggtgt cagacgaaac accgtcaccc tcggtcgcat tcccctcgcc ggcgccccag aaattggcaa ccgttcccag catcgctaca acctccgctc ctcaggcgcc gccggcactg cctgttcgcc gacccaaccg tagatgggac accactggaa ccagggccgg taagtctaag cagccgccgc cgttagccca agagcaacaa cagcgccaag gctaccgctc gtggcgcggg cacaagaacg ccatagttgc ttgcttgcaa gactgtgggg gcaacatctc cttcgcccgc cgctttcttc tctaccatca cggcgtggcc ttcccccgta acatcctgca ttactaccgt catctctaca gccctactg caccggcggc agcggcagcg gcagcaacag cagcggtcac acagaagcaa aggcgaccgg atagcaagac tctgacaaag cccaagaaat ccacagcggc ggcagcagca ggaggaggag cgctgcgtct ggcgcccaac gaacccgtat cgacccgcga gcttagaaat aggattttc ccactctgta tgctatattt caacaaagca ggggccaaga acaagagctg aaaataaaaa acaggtctct gcgctccctc acccgcagct gcctgtatca caaaagcgaa gatcagcttc ggcgcacgct ggaagacgcg gaggctctct tcagcaaata ctgcgcgctg actcttaagg actagtttcg cgccctttct caaatttaag cgcgaaaact acgtcatctc cagcggccac acccggcgcc agcacctgtc gtcagcgcca ttatgagcaa ggaaattccc acgccctaca tgtggagtta ccagccacaa atgggacttg cggctggagc tgcccaagac tactcaaccc gaataaacta catgagcgcg ggaccccaca tgatatcccg ggtcaacgga atccgcgccc accgaaaccg aattctcctc gaacaggcgg ctattaccac cacacctcgt aataaccta atccccgtag ttggcccgct gccctggtgt accaggaaag tcccgctccc accactgtgg tacttcccag agacgcccag gccgaagttc agatgactaa ctcaggggcg cagcttgcgg gcggctttcg tcacagggtg cggtcgcccg ggcgttttag ggcggagtaa cttgcatgta ttgggaattg tagttttttt aaaatgggaa gtgacgtatc gtgggaaaac ggaagtgaag atttgaggaa gttgtgggtt ttttggcttt cgtttctggg cgtaggttcg cgtgcgtttt tctgggtgtt ttttgtggac tttaaccgtt acgtcatttt ttagtcctat atatactcgc tctgtacttg gccttttta cactgtgact gattgagctg gtgccgtgtc gagtggtgtt ttttaatagg tttttttact ggtaaggctg actgttatgg ctgccgctgt ggaagcgctg tatgttgttc tggagcggga gggtgctatt ttgcctaggc aggagggttt ttcaggtgtt tatgtgtttt tctctcctat taattttgtt atacctccta tgggggctgt aatgttgtct ctacgcctgc gggtatgtat tcccccgggc tatttcggtc gctttttagc actgaccgat gttaaccaac ctgatgtgtt taccgagtct tacattatga ctccggacat gaccgaggaa ctgtcggtgg tgcttttaa tcacggtgac cagtttttt acggtcacgc cggcatggcc gtagtccgtc ttatgcttat aagggttgtt tttcctgttg taagacaggc ttctaatgtt taaatgtttt ttttttgtt
```

-continued

```
attttattttt gtgtttaatg caggaacccg cagacatgtt tgagagaaaa atggtgtctt tttctgtggt ggttccggaa cttacctgcc tttatctgca tgagcatgac tacgatgtgc ttgctttttt gcgcgaggct ttgcctgatt ttttgagcag caccttgcat tttatatcgc cgcccatgca acaagcttac atagggcta cgctggttag catagctccg agtatgcgtg tcataatcag tgtgggttct tttgtcatgg ttcctggcgg ggaagtggcc gcgctggtcc gtgcagacct gcacgattat gttcagctgg ccctgcgaag ggacctacgg gatcgcggta tttttgttaa tgttccgctt ttgaatctta tacaggtctg tgaggaacct gaatttttgc aatcatgatt cgctgcttga ggctgaaggt ggagggcgct ctggagcaga tttttacaat ggccggactt aatattcggg atttgcttag agacatattg ataaggtggc gagatgaaaa ttatttgggc atggttgaag gtgctggaat gtttatagag gagattcacc ctgaagggtt tagcctttac gtccacttgg acgtgagggc agtttgcctt ttggaagcca ttgtgcaaca tcttacaaat gccattatct gttctttggc tgtagagttt gaccacgcca ccgagggga gcgcgttcac ttaatagatc ttcattttga ggttttggat aatctttttgg aataaaaaaa aaaaaacatg gttcttccag ctcttcccgc tcctcccgtg tgtgactcgc agaacgaatg tgtaggttgg ctgggtgtgg cttattctgc ggtggtggat gttatcaggg cagcggcgca tgaaggagtt tacatagaac ccgaagccag ggggcgcctg gatgctttga gagagtggat atactacaac tactacacag agcgagctaa gcgacgagac cggagacgca gatctgtttg tcacgcccgc acctggtttt gcttcaggaa atatgactac gtccggcgtt ccatttggca tgacactacg accaacacga tctcggttgt ctcggcgcac tccgtacagt agggatcgcc tacctccttt tgagacagag acccgcgcta ccatactgga ggatcatccg ctgctgcccg aatgtaacac tttgacaatg cacaacgtga gttacgtgcg aggtcttccc tgcagtgtgg gatttacgct gattcaggaa tgggttgttc cctgggatat ggttctgacg cgggaggagc ttgtaatcct gaggaagtgt atgcacgtgt gcctgtgttg tgccaacatt gatatcatga cgagcatgat gatccatggt tacgagtcct gggctctcca ctgtcattgt tccagtcccg gttccctgca gtgcatagcc ggcgggcagg ttttggccag ctggtttagg atggtggtgg atggcgccat gtttaatcag aggtttatat ggtaccggga ggtggtgaat tacaacatgc caaaagaggt aatgtttatg tccagcgtgt ttatgagggg tcgccactta atctacctgc gcttgtggta tgatggccac gtgggttctg tggtccccgc catgagcttt ggatacagcg ccttgcactg tgggattttg aacaatattg tggtgctgtg ctgcagttac tgtgctgatt taagtgagat cagggtgcgc tgctgtgccc ggaggacaag gcgtctcatg ctgcgggcgg tgcgaatcat cgctgaggag accactgcca tgttgtattc ctgcaggacg gagcggcggc ggcagcagtt tattcgcgcg ctgctgcagc accaccgccc tatcctgatg cacgattatg actctacccc catgtaggcg tggacttccc cttcgccgcc cgttgagcaa ccgcaagttg gacagcagcc tgtggctcag cagctggaca gcgacatgaa cttaagcgag ctgcccgggg agtttattaa
```

-continued

```
tatcactgat gagcgtttgg ctcgacagga aaccgtgtgg aatataacac ctaagaatat gtctgttacc catgatatga tgcttttaa ggccagccgg ggagaaagga ctgtgtactc tgtgtgttgg gagggaggtg gcaggttgaa tactagggtt ctgtgagttt gattaaggta cggtgatcaa tataagctat gtggtggtgg ggctatacta ctgaatgaaa aatgacttga aattttctgc aattgaaaaa taaacacgtt gaaacataac atgcaacagg ttcacgattc tttattcctg ggcaatgtag gagaaggtgt aagagttggt agcaaaagtt tcagtggtgt attttccact ttcccaggac catgtaaaag acatagagta agtgcttacc tcgctagttt ctgtggattc actagaatcg atgtaggatg ttgcccctcc tgacgcggta ggagaagggg agggtgccct gcatgtctgc cgctgctctt gctcttgccg ctgctgagga gggggcgca tctgccgcag caccggatgc atctgggaaa agcaaaaaag gggctcgtcc ctgtttccgg aggaatttgc aagcggggtc ttgcatgacg gggaggcaaa ccccgttcg ccgcagtccg gccggcccga gactcgaacc ggggtcctg cgactcaacc cttggaaaat aaccctccgg ctacagggag cgagccactt aatgctttcg ctttccagcc taaccgctta cgccgcgcgc ggccagtggc caaaaaagct agcgcagcag ccgccgcgcc tggaaggaag ccaaaaggag cgctccccg ttgtctgacg tcgcacacct gggttcgaca cgcgggcggt aaccgcatgg atcacggcgg acggccggat ccggggttcg aaccccggtc gtccgccatg ataccccttgc gaatttatcc accagaccac ggaagagtgc ccgcttacag gctctccttt tgcacggtct agagcgtcaa cgactgcgca cgcctcaccg gccagagcgt cccgaccatg gagcactttt tgccgctgcg caacatctgg aaccgcgtcc gcgactttcc gcgcgcctcc accaccgccg ccggcatcac ctggatgtcc aggtacatct acggattacg tcgacgttta aaccatatga tcagctcact caaaggcggt aatacggtta ccacagaat caggggataa cgcaggaaag aacatgtgag caaaaggcca gcaaaaggcc aggaaccgta aaaaggccgc gttgctggcg ttttttccata ggctccgccc ccctgacgag catcacaaaa atcgacgctc aagtcagagg tggcgaaacc cgacaggact ataaagatac caggcgtttc ccctggaag ctccctcgtg cgctctcctg ttccgaccct gccgcttacc ggatacctgt ccgcctttct cccttcggga agcgtggcgc tttctcatag ctcacgctgt aggtatctca gttcggtgta ggtcgttcgc tccaagctgg gctgtgtgca cgaaccccc gttcagcccg accgctgcgc cttatccggt aactatcgtc ttgagtccaa cccggtaaga cacgacttat cgccactggc agcagccact ggtaacagga ttagcagagc gaggtatgta ggcggtgcta cagagttctt gaagtggtgg cctaactacg gctacactag aagaacagta tttggtatct gcgctctgct gaagccagtt accttcggaa aaagagttgg tagctcttga tccggcaaac aaaccaccgc tggtagcggt ggttttttg tttgcaagca gcagattacg cgcagaaaaa aaggatctca agaagatcct ttgatctttt ctacggggtc tgacgctcag tggaacgaaa actcacgtta agggattttg gtcatgagat tatcaaaaag
```

-continued
```
gatcttcacc tagatccttt taaattaaaa atgaagtttt aaatcaatct aaagtatata tgagtaaact tggtctgaca gtcagaagaa ctcgtcaaga aggcgataga aggcgatgcg ctgcgaatcg ggagcggcga taccgtaaag cacgaggaag cggtcagccc attcgccgcc aagctcttca gcaatatcac gggtagccaa cgctatgtcc tgatagcggt ccgccacacc cagccggcca cagtcgatga atccagaaaa gcggccattt tccaccatga tattcggcaa gcaggcatcg ccatgggtca cgacgagatc ctcgccgtcg ggcatgctcg ccttgagcct ggcgaacagt tcggctggcg cgagcccctg atgctcttcg tccagatcat cctgatcgac aagaccggct tccatccgag tacgtgctcg ctcgatgcga tgtttcgctt ggtggtcgaa tgggcaggta gccggatcaa gcgtatgcag ccgccgcatt gcatcagcca tgatggatac tttctcggca ggagcaaggt gagatgacag gagatcctgc cccggcactt cgcccaatag cagccagtcc cttcccgctt cagtgacaac gtcgagtaca gctgcgcaag gaacgcccgt cgtggccagc cacgatagcc gcgctgcctc gtcttgcagt tcattcaggg caccggacag gtcggtcttg acaaaaagaa ccgggcgccc ctgcgctgac agccggaaca cggcggcatc agagcagccg attgtctgtt gtgcccagtc atagccgaat agcctctcca cccaagcggc cggagaacct gcgtgcaatc catcttgttc aatcatactc ttccttttc aatattattg aagcatttat cagggttatt gtctcatgag cggatacata tttgaatgta tttagaaaaa taaacaaata ggggttccgc gcacatttcc ccgaaaagtg ccacctaaat tgtaagcgtt aatattttgt taaaattcgc gttaaattt tgttaaatca gctcattttt taaccaatag gccgaaatcg gcaaaatccc ttataaatca aagaataga ccgagatagg gttgagtgtt gttccagttt ggaacaagag tccactatta aagaacgtgg actccaacgt caaagggcga aaaaccgtct atcagggcga tggcccacta cgtgaaccat cacgcactaatc aagtttttg gggtcgaggt gccgtaaagc actaaatcgg aaccctaaag ggagccccg atttagagct tgacggggaa agccggcgaa cgtggcgaga aaggaaggga agaaagcgaa aggagcgggc gctagggcgc tggcaagtgt agcggtcacg ctgcgcgtaa ccaccacacc cgccgcgctt aatgcgccgc tacagggcgc gatggatcc
```

In SEQ ID NO:2, residues 1-5343 of pHelper-Kan are derived from adenovirus, and include a polynucleotide encoding the E2A protein (residues 258-1847); residues 5344-8535 are derived from adenovirus, and include a polynucleotide encoding the E4orf6 protein; residues 9423-10011 correspond to ori sequences; residues 10182-10976 encode a kanamycin resistance determinant expressed by a bla promoter sequence (residues 10977-11081); residues 11107-11561 correspond to f1 ori sequences (FIG. 5).

Figure 6:
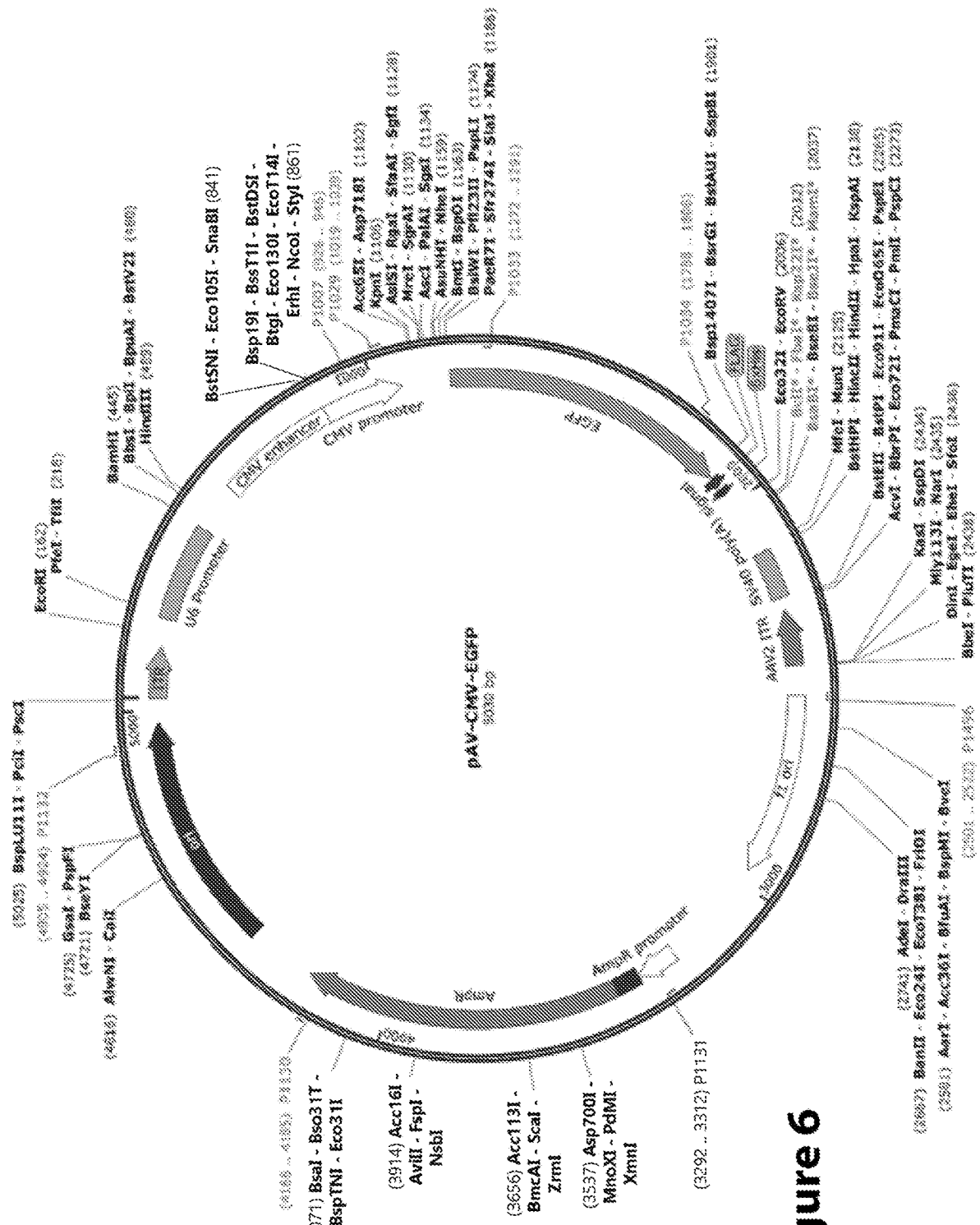
FIG. 6 shows a map of the rAAV plasmid vector pAV-CMV-EGFP.

As discussed above, AAV helper function-providing polynucleotides and non-AAV helper function-providing polynucleotides are typically employed in concert with an rAAV plasmid vector to comprise a triple plasmid transfection system. Multiple commercially available rAAV plasmid vectors (e.g., pAV-CMV-EGFP, pGOI, etc. (Cell Biolabs, Inc., Invitrogen and Stratagene)) may be used in accordance with the present invention. An illustrative rAAV plasmid vector that may be used in accordance with the present invention is pAV-CMV-EGFP (SEQ ID NO:3; FIG. 6) which comprises a 5' ITR, a U6 promoter, CMV enhancer and promoter sequences, a polynucleotide encoding the enhanced green fluorescent protein (EGFP) (Gambotto, A. et al. (2000) "*Immunogenicity Of Enhanced Green Fluorescent Protein (EGFP) In BALB/C Mice: Identification Of An H2-Kd-Restricted CTL Epitope*," Gene Ther. 7(23): 2036-2040; Tsien, R. Y. (1998) "*The Green Fluorescent Protein*," Annu. Rev. Biochem. 67: 509-544; Cinelli, R. A. et al. (2000) "*The Enhanced Green Fluorescent Protein As A Tool For The Analysis Of Protein Dynamics And Localization: Local Fluorescence Study At The Single-Molecule Level*," Photochem. Photobiol. 71(6): 771-776; Chopra A. (2008) "*Recombinant Adenovirus With Enhanced Green Fluorescent Protein*," In: MOLECULAR IMAGING AND CONTRAST AGENT Database (MICAD), National Center for Biotechnology Information, Bethesda MD), FLAG-tag and 6×His-tag sites for facilitating recovery or localization of expressed proteins, an SV40 poly(A) site and a 3' ITR.

```
Coding Strand of Plasmid pAV-CMV-EGFP (SEQ ID NO: 3):
cctgcaggca gctgcgcgct cgctcgctca ctgaggccgc ccgggcgtcg ggcgaccttt ggtcgcccgg ccctccagtg agcgagcgcg cagagaggga gtggccaact ccatcactag gggttcctgc ggccgcacgc gtctagttat taatagtaat cgaattcgtg ttactcataa ctagtaaggt cgggcaggaa gagggcctat ttcccatgat tccttcatat ttgcatatac gatacaaggc tgttagagag ataattagaa ttaatttgac tgtaaacaca aagatattag tacaaaatac gtgacgtaga agtaataat ttcttgggta gtttgcagtt ttaaaattat gttttaaaat ggactatcat atgcttaccg taacttgaaa gtatttcgat ttcttgggtt tatatatctt gtggaaagga cgcgggatcc actggaccag gcagcagcgt cagaagactt ttttggaaaa gcttgactag taatactgta atagtaatca attacggggt cattagttca tagcccatat atggagttcc gcgttacata acttacggta aatggcccgc ctggctgacc gcccaacgac ccccgcccat tgacgtcaat aatgacgtat gttcccatag taacgccaat agggactttc cattgacgtc aatgggtgga gtatttacgg taaactgccc acttggcagt acatcaagtg tatcatatgc caagtacgcc ccctattgac gtcaatgacg gtaaatggcc cgcctggcat tatgcccagt acatgacctt atgggacttt cctacttggc agtacatcta cgtattagtc atcgctatta ccatggtgat gcggttttgg cagtacatca atgggcgtgg atagcggttt gactcacggg gatttccaag tctccacccc attgacgtca atgggagttt gttttgcacc aaaatcaacg ggactttcca aaatgtcgta acaactccgc cccattgacg caaatggggc gtaggcgtgt acggtgggag gtctatataa gcagagctgg tttagtgaac cgtcagatcc gctagagatc cggtaccgag gagatctgcc gccgcgatcg ccggcgcgcc agatctcacg cttaactagc tagcggaccg acgcgtacgc ggccgctcga gatggtgagc aagggcgagg agctgttcac cggggtggtg cccatcctgg tcgagctgga cggcgacgta aacggccaca gttcagcgt gtccggcgag ggcgagggc atgccaccta cggcaagctg accctgaagt tcatctgcac caccggcaag ctgcccgtgc cctggcccac cctcgtgacc accctgacct acggcgtgca gtgcttcagc cgctacccg accacatgaa gcagcacgac ttcttcaagt ccgccatgcc cgaaggctac gtccaggagc gcaccatctt cttcaaggac gacggcaact acaagacccg cgccgaggtg aagttcgagg gcgacaccct ggtgaaccgc atcgagctga agggcatcga cttcaaggag gacggcaaca tcctggggca caagctggag tacaactaca acagccacaa cgtctatatc atggccgaca agcagaagaa cggcatcaag gtgaacttca gatccgcca caacatcgag gacggcagcg tgcagctcgc cgaccactac cagcagaaca cccccatcgg cgacggcccc gtgctgctgc ccgacaacca ctacctgagc acccagtccg ccctgagcaa agacccaac gagaagcgcg atcacatggt cctgctggag ttcgtgaccg ccgccgggat cactctcggc atggacgagc tgtacaagta agtcgaggat tataaggatg acgacgataa attcgtcgag
```

-continued

```
caccaccacc accaccacta ataaggttta tccgatccac cggatctaga taagatatcc gatccaccgg atctagataa ctgatcataa tcagccatac cacatttgta gaggttttac ttgctttaaa aaacctccca cacctccccc tgaacctgaa acataaaatg aatgcaattg ttgttgttaa cttgtttatt gcagcttata atggttacaa ataaagcaat agcatcacaa atttcacaaa taaagcattt ttttcactgc attctagttg tggtttgtcc aaactcatca atgtatctta acgcggtaac cacgtgcgga ccgagcggcc gcaggaaccc ctagtgatgg agttggccac tccctctctg cgcgctcgct cgctcactga ggccgggcga ccaaaggtcg cccgacgccc gggctttgcc cgggcggcct cagtgagcga gcgagcgcgc agctgcctgc aggggcgcct gatgcggtat tttctcctta cgcatctgtg cggtatttca caccgcatac gtcaaagcaa ccatagtacg cgccctgtag cggcgcatta agcgcggcgg gtgtggtggt tacgcgcagc gtgaccgcta cacctgccag cgccttagcg cccgctcctt tcgctttctt cccttccttt ctcgccacgt tcgccggctt tccccgtcaa gctctaaatc gggggctccc tttagggttc cgatttagtg ctttacggca cctcgacccc aaaaaacttg atttgggtga tggttcacgt agtgggccat cgccctgata dacggttttt cgcccttttga cgttggagtc cacgttcttt aatagtggac tcttgttcca aactggaaca acactcaacc ctatctcggg ctattctttt gatttataag ggattttgcc gatttcggcc tattggttaa aaaatgagct gatttaacaa aaatttaacg cgaattttaa caaaatatta acgtttacaa ttttatggtg cactctcagt acaatctgct ctgatgccgc atagttaagc cagccccgac acccgccaac acccgctgac gcgccctgac gggcttgtct gctcccggca tccgcttaca gacaagctgt gaccgtctcc gggagctgca tgtgtcagag gttttcaccg tcatcaccga aacgcgcgag acgaaagggc ctcgtgatac gcctattttt ataggttaat gtcatgataa taatggtttc ttagacgtca ggtggcactt ttcggggaaa tgtgcgcgga acccctattt gtttattttt ctaaatacat tcaaatatgt atccgctcat gagacaataa ccctgataaa tgcttcaata atattgaaaa aggaagagta tgagtattca acatttccgt gtcgccctta ttccctttt tgcggcattt tgccttcctg ttttgctca cccagaaacg ctggtgaaag taaaagatgc tgaagatcag ttgggtgcac gagtgggtta catcgaactg gatctcaaca gcggtaagat ccttgagagt tttcgccccg aagaacgttt tccaatgatg agcacttttta aagttctgct atgtggcgcg gtattatccc gtattgacgc cgggcaagag caactcggtc gccgcataca ctattctcag aatgacttgg ttgagtactc accagtcaca gaaaagcatc ttacggatgg catgacagta agagaattat gcagtgctgc cataaccatg agtgataaca ctgcggccaa cttacttctg acaacgatcg gaggaccgaa ggagctaacc gcttttttgc acaacatggg ggatcatgta actcgccttg atcgttggga accggagctg aatgaagcca taccaaacga cgagcgtgac accacgatgc ctgtagcaat ggcaacaacg ttgcgcaaac tattaactgg cgaactactt actctagctt
```

-continued

```
cccggcaaca attaatagac tggatggagg cggataaagt tgcaggacca cttctgcgct cggcccttcc ggctggctgg tttattgctg ataaatctgg agccggtgag cgtgggtctc gcggtatcat tgcagcactg gggccagatg gtaagccctc ccgtatcgta gttatctaca cgacggggag tcaggcaact atggatgaac gaaatagaca gatcgctgag ataggtgcct cactgattaa gcattggtaa ctgtcagacc aagtttactc atatatactt tagattgatt taaaacttca tttttaattt aaaaggatct aggtgaagat ccttttgat aatctcatga ccaaaatccc ttaacgtgag ttttcgttcc actgagcgtc agacccgta gaaaagatca aaggatcttc ttgagatcct ttttttctgc gcgtaatctg ctgcttgcaa acaaaaaaac caccgctacc agcggtggtt tgtttgccgg atcaagagct accaactctt tttccgaagg taactggctt cagcagagcg cagataccaa atactgtcct tctagtgtag ccgtagttag gccaccactt caagaactct gtagcaccgc ctacatacct cgctctgcta atcctgttac cagtggctgc tgccagtggc gataagtcgt gtcttaccgg gttggactca agacgatagt taccggataa ggcgcagcgg tcgggctgaa cggggggttc gtgcacacag cccagcttgg agcgaacgac ctacaccgaa ctgagatacc tacagcgtga gctatgagaa agcgccacgc ttcccgaagg gagaaaggcg gacaggtatc cggtaagcgg cagggtcgga acaggagagc gcacgaggga gcttccaggg ggaaacgcct ggtatcttta tagtcctgtc gggtttcgcc acctctgact tgagcgtcga tttttgtgat gctcgtcagg ggggcggagc ctatgaaaaa acgccagcaa cgcggccttt ttacggttcc tggccttttg ctggcctttt gctcacatgt
```

In SEQ ID NO:3, residues 1-128 of pAV-CMV-EGFP correspond to the 5' ITR; residues 201-441 are U6 promoter sequences; residues 562-865 are human cytomegalovirus (CMV) immediate early enhancer sequences; residues 866-1068 comprise the CMV immediate early promoter; residues 1192-1911 comprise a mammalian codon-optimized polynucleotide that encodes the EGFP; residues 1918-1941 encode the FLAG-tag; residues 1951-1968 encode the 6×His-tag; residues 2139-2260 encode the SV40 poly(A) sequence; residues 2293-2433 correspond to the 3' ITR; residues 2508-22963 correspond to F1 ori sequences; residues 3350-4210 encode an ampicillin resistance determinant and its signal sequence (residues 3350-3418) expressed by a bla promoter sequence (residues 3245-3349); residues 4381-4969 correspond to an ori sequence (FIG. 6).

Figure 7:
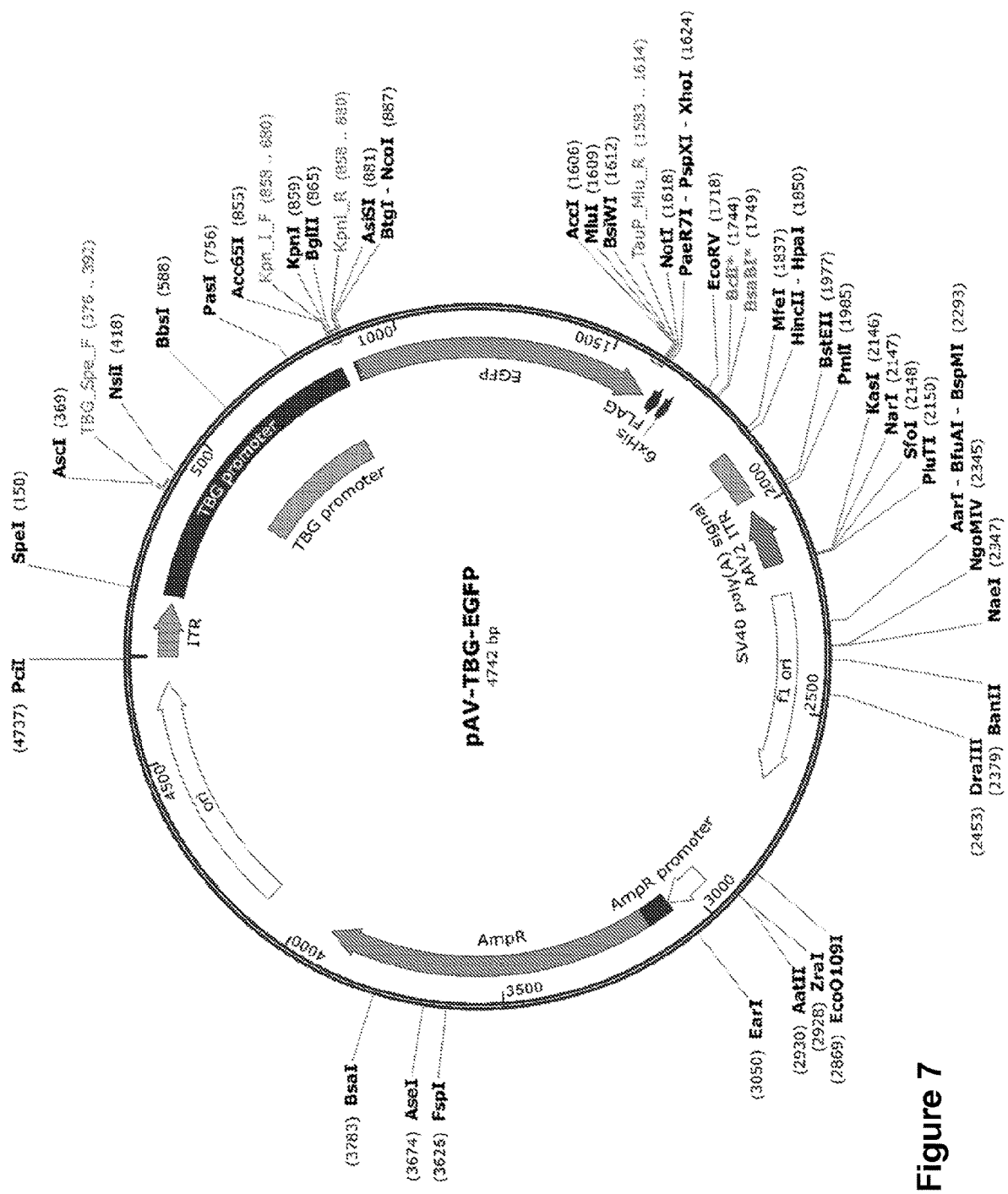
FIG. 7 shows a map of the rAAV plasmid vector pAV-TBG-EGFP.

A second illustrative rAAV plasmid vector that may be used in accordance with the present invention is pAV-TBG-EGFP (SEQ ID NO:4; FIG. 7) which comprises a 5' ITR, a thyroid hormone-binding globulin (TBG) promoter, a polynucleotide encoding the enhanced green fluorescent protein (EGFP), FLAG-tag and 6×His-tag sites for facilitating recovery or localization of expressed proteins, an SV40 poly(A) site and a 3' ITR.

```
Coding Strand of Plasmid pAV-TBG-EGFP (SEQ ID NO: 4):
cctgcaggca gctgcgcgct cgctcgctca ctgaggccgc ccgggcgtcg ggcgaccttt ggtcgcccgg cctcagtgag cgagcgagcg cgcagagagg gagtggccaa ctccatcact aggggttcct gcggccggtc gcgtctagta ctagtaggtt aatttttaaa aagcagtcaa aagtccaagt ggcccttggc agcatttact ctctctgttt gctctggtta ataatctcag gagcacaaac attccagatc caggttaatt tttaaaaagc agtcaaaagt ccaagtggcc cttggcagca tttactctct ctgtttgctc tggttaataa tctcaggagc acaaacattc cagatccggc gcgccagggc tggaagctac ctttgacatc atttcctctg cgaatgcatg tataatttct acagaaccta ttagaaagga
```

-continued

```
tcacccagcc tctgcttttg tacaactttc ccttaaaaaa ctgccaattc cactgctgtt tggcccaata gtgagaactt tttcctgctg cctcttggtg cttttgccta tggcccctat tctgcctgct gaagacactc ttgccagcat ggacttaaac ccctccagct ctgacaatcc tctttctctt ttgttttaca tgaagggtct ggcagccaaa gcaatcactc aaagttcaaa ccttatcatt ttttgctttg ttcctcttgg ccttggtttt gtacatcagc tttgaaaata ccatcccagg gttaatgctg gggttaattt ataactaaga gtgctctagt tttgcaatac aggacatgct ataaaaatgg aaagatgttg ctttctgaga gacaggtacc gaggagatct gccgccgcga tcgccaccat ggtgagcaag ggcgaggagc tgttcaccgg ggtggtgccc atcctggtcg agctggacgg cgacgtaaac ggccacaagt tcagcgtgtc cggcgagggc gagggcgatg ccacttacgg caagctgacc ctgaagttca tctgcaccac cggcaagctg cccgtgccct ggcccaccct cgtgaccacc ctgacctacg gcgtgcagtg cttcagccgc tacccgacc acatgaagca gcacgacttc ttcaagtccg ccatgcccga aggctacgtc caggagcgca ccatcttctt caaggacgac ggcaactaca agacccgcgc cgaggtgaag ttcgagggcg acaccctggt gaaccgcatc gagctgaagg gcatcgactt caaggaggac ggcaacatcc tggggcacaa gctggagtac aactacaaca gccacaacgt ctatatcatg gccgacaagc agaagaacgg catcaaggtg aacttcaaga tccgccacaa catcgaggac ggcagcgtgc agctcgccga ccactaccag cagaacaccc ccatcggcga cggccccgtg ctgctgcccg acaaccacta cctgagcacc cagtccgccc tgagcaaaga ccccaacgag aagcgcgatc acatggtcct gctggagttc gtgaccgccg ccgggatcac tctcggcatg gacgagctgt acaagtagac gcgtacgcgg ccgctcgagg attataagga tgacgacgat aaattcgtcg agcaccacca ccaccaccac taataaggtt tatccgatcc accggatcta gataagatat ccgatccacc ggatctagat aactgatcat aatcagccat accacatttg tagaggtttt acttgcttta aaaaacctcc cacacctccc cctgaacctg aaacataaaa tgaatgcaat tgttgttgtt aacttgtttta ttgcagctta taatggttac aaataaagca atagcatcac aaatttcaca aataaagcat ttttttcact gcattctagt tgtggtttgt ccaaactcat caatgtatct taacgcggta accacgtgcg gacccaacgg ccgcaggaac ccctagtgat ggagttggcc actccctctc tgcgcgctcg ctcgctcact gaggccgggc gaccaaaggt cgcccgacgc ccgggctttg cccgggcggc ctcagtgagc gagcgagcgc gcagctgcct gcaggggcgc ctgatgcggt attttctcct tacgcatctg tgcggtattt cacaccgcat acgtcaaagc aaccatagta cgcgccctgt agcggcacat taagcgcggc gggtgtggtg gttacgcgca gcgtgaccgc tacacctgcc agcgccttag cgcccgctcc tttcgctttc ttcccttcct ttctcgccac gttcgccggc tttccccgtc aagctctaaa tcgggggctc cctttagggt tccgatttag tgctttacgg cacctcgacc ccaaaaaact tgatttgggt gatggttcac gtagtgggcc atcgccctga tagacggttt ttcgcccttt gacgttggag
```

```
tccacgttct ttaatagtgg actcttgttc caaactggaa caacactcaa ctctatctcg ggctattctt ttgatttata agggattttg ccgatttcgg tctattggtt aaaaaatgag ctgatttaac aaaaatttaa cgcgaatttt aacaaaatat taacgtttac aattttatgg tgcactctca gtacaatctg ctctgatgcc gcatagttaa gccagccccg acaccegcca acacccgctg acgcgccctg acgggcttgt ctgctcccgg catccgctta cagacaagct gtgaccgtct ccgggagctg catgtgtcag aggttttcac cgtcatcacc gaaacgcgcg agacgaaagg gcctcgtgat acgcctattt ttataggtta atgtcatgat aataatggtt tcttagacgt caggtggcac ttttcgggga aatgtgcgcg gaacccctat ttgtttattt ttctaaatac attcaaatat gtatccgctc atgagacaat aaccctgata aatgcttcaa taatattgaa aaaggaagag tatgagtatt caacatttcc gtgtcgccct tattccctt tttgcggcat tttgccttcc tgttttgct cacccagaaa cgctggtgaa agtaaaagat gctgaagatc agttgggtgc acgagtgggt tacatcgaac tggatctcaa cagcggtaag atccttgaga gttttcgccc cgaagaacgt tttccaatga tgagcacttt taaagttctg ctatgtggcg cggtattatc ccgtattgac gccgggcaag agcaactcgg tcgccgcata cactattctc agaatgactt ggttgagtac tcaccagtca cagaaaagca tcttacggat ggcatgacag taagagaatt atgcagtgct gccataacca tgagtgataa cactgcggcc aacttacttc tgacaacgat cggaggaccg aaggagctaa ccgcttttttt gcacaacatg ggggatcatg taactcgcct tgatcgttgg gaaccggagc tgaatgaagc cataccaaac gacgagcgtg acaccacgat gcctgtagca atggcaacaa cgttgcgcaa actattaact ggcgaactac ttactctagc ttcccggcaa caattaatag actggatgga ggcggataaa gttgcaggac cacttctgcg ctcggccctt ccggctggct ggtttattgc tgataaatct ggagccggtg agcgtgggtc tcgcggtatc attgcagcac tggggccaga tggtaagccc tcccgtatcg tagttatcta cacgacgggg agtcaggcaa ctatggatga acgaaataga cagatcgctg ataggtgc ctcactgatt aagcattggt aactgtcaga ccaagtttac tcatatatac tttagattga tttaaaactt catttttaat ttaaaaggat ctaggtgaag atcctttttg ataatctcat gaccaaaatc ccttaacgtg agttttcgtt ccactgagcg tcagaccccg tagaaaagat caaaggatct tcttgagatc ctttttttct gcgcgtaatc tgctgcttgc aaacaaaaaa accaccgcta ccagcggtgg tttgtttgcc ggatcaagag ctaccaactc ttttccgaa ggtaactggc ttcagcagag cgcagatacc aaatactgtt cttctagtgt agccgtagtt aggccaccac ttcaagaact ctgtagcacc gcctacatac ctcgctctgc taatcctgtt accagtggct gctgccagtg gcgataagtc gtgtcttacc gggttggact caagacgata gttaccggat aaggcgcagc ggtcgggctg aacggggggt tcgtgcacac agcccagctt ggagcgaacg acctacaccg aactgagata cctacagcgt gagctatgag aaagcgccac
```

```
                  -continued
gcttcccgaa gggagaaagg cggacaggta tccggtaagc ggcagggtcg gaacaggaga gcgcacgagg gagcttccag ggggaaacgc ctggtatctt tatagtcctg tcgggtttcg ccacctctga cttgagcgtc gattttgtg atgctcgtca gggggcgga gcctatgaa aaacgccagc aacgcggcct ttttacggtt cctggccttt tgctggcctt ttgctcacat gt
```

In SEQ ID NO:4, residues 1-130 of pAV-TBG-EGFP correspond to the 5' ITR; residues 150-854 are TBG promoter sequences, with residues 415-824 comprising the TBG promoter; residues 886-1608 encode the EGFP; residues 1630-1653 encode the FLAG-tag; residues 1663-1680 encode the 6xHis-tag; residues 1851-1972 encode the poly (A) sequence; residues 2005-2145 corresponds to the 3' ITR; residues 2220-2675 correspond to F1 ori sequences; residues 3062-3922 encode an ampicillin resistance determinant and its signal sequence (residues 3062-3130) expressed by a bla promoter sequence (residues 2957-3061); residues 4093-4681 correspond to an ori sequence (FIG. 7).

In particular, the present invention provides a recombinantly-modified adeno-associated virus (rAAV), such as pAV-CMV-EGFP or pAV-TBG-EGFP, that comprises a Cis-Element in one or more of its P1, P2, P3 or P4 Domains, wherein:

(1) the P1 Domain is 5' to a 5' ITR of the rAAV;
(2) the P2 Domain is 3' to the 5' ITR of the rAAV and 5' to a transgene cassette of the rAAV;
(3) the P3 Domain is 3' to the transgene cassette of the rAAV and 5' to a 3' ITR of the rAAV; and
(4) the P4 Domain is 3' to the 3' ITR of the rAAV; and wherein the presence of the Cis-Element causes rAAV-producing cells to produce the rAAV at a higher production titer than would be attained with such rAAV if lacking the Cis-Element.

In one embodiment, the Cis-Element will preferably comprise an introduced nucleotide sequence that was not previously present in rAAV vector. In other embodiments, the introduced nucleotide sequence was previously present in such rAAV plasmid vector, and has been positioned in the recombinantly-produced rAAV plasmid vector, adjacent to, or immediately adjacent to, such previously present nucleotide sequence. Alternatively, such introduced nucleotide sequence may be positioned at a site that is not adjacent to such previously present nucleotide sequence.

Figure 8:
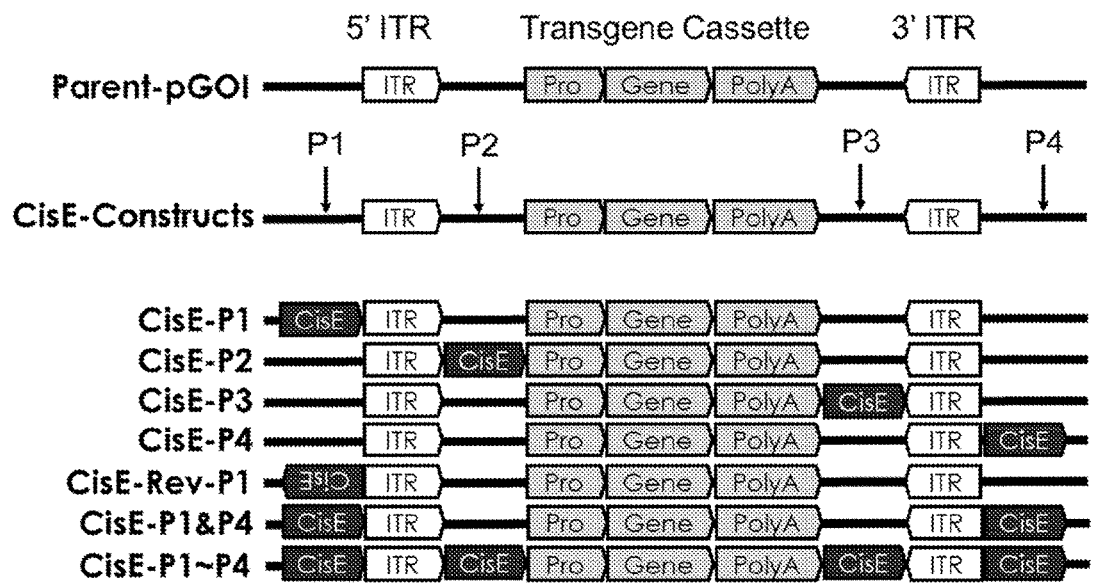
FIG. 8 shows the overall structure and approach followed for the development of the exemplary rAAV constructs described herein (ITR: adeno-associated virus (AAV)-specific palindromic inverted terminal repeated sequences; Pro: promoter. Gene: transgene; PolyA: polynucleotide comprising poly-deoxyadenosine sequence; CisE: polynucleotide comprising a Cis-Element).

As shown in FIG. 8, an rAAV or an rAAV plasmid vector of the present invention may be envisioned as having, in the 5' to 3' direction:

(1) the 5' terminus of the rAAV;
(2) a polynucleotide region (the "P1 Domain")
(3) a "5' ITR," which is an ITR that is located at or near the 5' end of the polynucleotide chain that comprises the coding strand of the transgene cassette of the rAAV;
(4) a polynucleotide region (the "P2 Domain")
(5) a transgene cassette (including a preceding (i.e., 5'-positioned) promoter ("Pro"), the transgene encoding sequence ("Gene"), and following (i.e., 3'-positioned) poly-A sequence ("PolyA");
(6) a polynucleotide region (the "P3 Domain")
(7) a "3' ITR," which is an ITR that is located at or near the 3' end of the polynucleotide chain that comprises the coding strand of the transgene cassette of the rAAV;
(8) a polynucleotide region (the "P4 Domain"); and
(9) the 3' terminus of the rAAV."

Such P1, P2, P3, and P4 Domains need not all be present in any particular rAAV or rAAV plasmid vector, and an rAAV or rAAV plasmid vector may lack any 1, 2, or 3 of these Domains, or may lack all 4 of such Domains. The boundaries of such Domains are defined by the other domains of the rAAV or rAAV plasmid vector. Thus, the P1 Domain extends from the 5' terminus of the rAAV or rAAV plasmid vector to the 5' terminus of the 5' ITR. The PciI site of pAV-CMV-EGFP or pAV-TBG-EGFP is an example of a suitable site within the P1 Domain of an rAAV or rAAV-plasmid vector for insertion of a Cis-Element. The P2 Domain extends from the 3' terminus of the 5' ITR to the 5' terminus of the transgene cassette. The P3 Domain extends from the 3' terminus of the transgene cassette to the 5' terminus of the 3' ITR. The EcoR1 site of pAV-CMV-EGFP or the SpeI site of pAV-TBG-EGFP are examples of suitable sites within the P2 Domain of an rAAV or rAAVplasmid vector for insertion of a Cis-Element. The P3 Domain extends from the 3' terminus of the poly(A) sequence to the 3' ITR of the rAAV or rAAV plasmid vector. The PmlI site of pAV-CMV-EGFP or pAV-TBG-EGFP is an example of a suitable site within the P3 Domain of an rAAV or rAAV-plasmid vector for insertion of a Cis-Element. The P4 Domain extends from the 3' terminus of the 3' ITR to the 3' terminus of the rAAV or rAAV plasmid vector. The KasI site of pAV-CMV-EGFP or pAV-TBG-EGFP is an example of a suitable site within the P4 Domain of an rAAV or rAAV-plasmid vector for insertion of a Cis-Element. The precise location of a Cis-Element of the present invention within a particular P1, P2, P3, or P4 Domain is not material to the ability of such positioned Cis-Element to mediate an increase in rAAV production titers. Insertions of Cis-Element(s) may be made by ligating a Cis-Element into a suitable restriction site or by employing primers to install such Cis-Elements.

The present invention employs the nomenclature of CisE1, CisE2, etc. to identify particular Cis-Elements. Such designation is followed by "For" or "Rev" in some cases to indicate that the Cis-Element is being (respectively) inserted into the rAAV in its forward orientation or in its reverse orientation. When "For" or "Rev" are not indicated, the Cis-Element is being inserted into the rAAV in its forward orientation. Lastly, the present invention employs the nomenclature P1, P2, P3, or P4 Domain to indicate the domain within which the Cis-Element has been inserted. Thus, for example, an rAAV or rAAV plasmid vector containing Cis-Element CisE1 of the present invention within its P1 Domain in its forward orientation is referred to herein by the designation "CisE1-For-P1" or "CisE1-P1;" an rAAV or rAAV plasmid vector containing Cis-Element CisE21 of the present invention within its P2 Domain in its forward orientation is referred to herein by the designation "CisE21-For-P2" or "CisE1-P2;" an rAAV or rAAV plasmid vector containing Cis-Element CisE30 of the present invention within its P4 Domain in its reverse orientation is referred to herein by the designation "CisE30-Rev-P4." Thus, with reference to the constructs shown schematically in FIG. 8, constructs CisE-P1, CisE-Rev-P1, CisE-P1&P4, CisE-P1~P4 all contain Cis-Elements within the P1 Domain (the orientation of the Cis-Element may be reversed, as in CisE-Rev-P1); the construct CisE-P1&P4 contains Cis-Elements within the P1 Domain and within the P4 Domain; the construct CisE-P1~P4 contains Cis-Elements within the P1, P2, P3 and P4 Domains.

In one embodiment, such Cis-Elements are actual or potential "G-Quadruplex Sequences" capable of forming a G-Quadruplex Structure. The G-Quadruplex Structures of particular relevance to the present invention comprise only a single polynucleotide chain, and have the general formula of four series, each composed of 3 or more deoxyguanosine residues, wherein the first, second and third such series is separated from the fourth such series by from 1 to 7 of any other nucleotide residue.

In some cases, a particular polynucleotide will comprise a sequence that is known to comprise a G-Quadruplex Sequence (i.e., an "Actual G-Quadruplex Sequence"). In other cases, a particular sequence will be predicted to comprise a G-Quadruplex Sequence that can form a G-Quadruplex Structure (i.e., a "Potential G-Quadruplex Sequence"). Predictive algorithms for determining whether any particular polynucleotide is a potential G-Quadruplex Sequence are well known, and thus the recognition of whether a particular polynucleotide is a potential G-Quadruplex Sequence may be readily accomplished. Examples of such predictive algorithms include G4P Calculator (Eddy, J. et al. (2006) "*Gene Function Correlates With Potential For G4 DNA Formation In The Human Genome*," Nucleic Acids Res. 34: 3887-3896), QuadParser (Huppert, J. L. et al. (2005) "*Prevalence Of Quadruplexes In The Human Genome*," Nucleic Acids Res. 33: 2908-29168) and GHunter (Bedrat, A. et al. (2016) "*Re-evaluation of G-Quadruplex propensity with G4Hunter*," Nucleic Acids Res. 44(4): 1746-1759), have been developed to identify potential G-Quadruplex Sequences (Huppert, J. L. et al. (2007) "*G-Quadruplexes In Promoters Throughout The Human Genome*," Nucleic Acids Res. 35: 406-413; Verma, A. et al. (2008) "*Genome-Wide Computational And Expression Analyses Reveal G-Quadruplex DNA Motifs As Conserved Cis-Regulatory Elements In Human And Related Species*," J. Med. Chem. 51: 5641-5649).

The invention further encompasses compositions such as plasmids that are genetically engineered to replicate high levels of recombinant viral genomes. The replication of viral genomes may be regulated through the use of Cis-Elements, including replication origins, promoters and enhancers. Such Cis-Elements can be genetically engineered into recombinant plasmids that are designed to pack AAV vectors. Further, the invention encompasses the Cis-Elements can be located before or after ITRs.

Cis-elements of the present invention that increase AAV production particularly include:

(1) Potential G-Quadruplex Sequences of wild type AAV genomes (e.g., CisE1-CisE16 (SEQ ID NOs:5, 7, 9, 11, 13, 15, 17, 19, 21, 23, 25, 27, 29, 31, 33 and 35)), or Potential G-Quadruplex Sequences in a reversed orientation (e.g., CisE1-Rev-CisE16-Rev (SEQ ID NOs:6, 8, 10, 12, 14, 16, 18, 20, 22, 24, 26, 28, 30, 32, 34 and 36));

(2) Actual G-Quadruplex Sequences (e.g., CisE17-CisE20 (SEQ ID NOs:37, 39, 41 and 43)) or Actual G-Quadruplex Sequences in a reversed orientation (e.g., CisE17-Rev-CisE20-Rev (SEQ ID NOs:38, 40, 42 and 44);

(3) Other DNA sequences from wild-type AAV (e.g., CisE21-CisE26 and CisE31-CisE35 (SEQ ID NOs:45, 47, 49, 51, 53, 55, 65, 67, 69, 71 and 73)) or other DNA sequences from wild-type AAV in a reversed orientation (e.g., CisE21-Rev-CisE26-Rev and CisE31-Rev-CisE35-Rev (SEQ ID NOs: 46, 48, 50, 52, 54, 56, 66, 68, 72 and 74); and (4) DNA sequences from other viral genomes (e.g., CisE27-CisE30 (SEQ ID NOs:57, 59, 61 and 63)) or such DNA sequences from other viral sources in a reversed orientation (e.g., CisE27-Rev-CisE30-Rev (SEQ ID NOs: 58, 60, 62 and 64) and human genomes.

TABLE 1 provides the sequences, sequence designations, and origins of such preferred exemplary Cis-Elements of the present invention.

| SEQ ID NO | Sequence Designation | Source or Origin | Sequence |
|---|---|---|---|
| 5 | CisE1 | GQ4 | gggtggccga gaaggaatgg |
| 6 | CisE1-Rev | GQ4-Rev | ggtaaggaag agccggtggg |
| 7 | CisE2 | GQ5 | ggaatggcgc cgtgtgagta aggcccgg |
| 8 | CisE2-Rev | GQ5-Rev | ggccccggaa tgagtgtgcc gcggtaagg |
| 9 | CisE3 | GQ6 | ggaaaccacc ggggtgaaat ccatgg |
| 10 | CisE3-Rev | GQ6-Rev | ggtacctaaa gtggggccac caaagg |
| 11 | CisE4 | GQ7 | ggaggcggga acaaggtggt gg |
| 12 | CisE4-Rev | GQ7-Rev | ggtggtggaa caagggcgga gg |
| 13 | CisE5 | GQ10 | ggatccagga ggaccagg |
| 14 | CisE5-Rev | GQ10-Rev | ggaccaggag gacctagg |
| 15 | CisE6 | GQ12 | ggcaagagga acaccatctg gctgtttggg |
| 16 | CisE6-Rev | GQ12-Rev | gggtttgtcg gtctaccaca aggagaacgg |

TABLE 1-continued provides the sequences, sequence designations, and origins of such preferred exemplary Cis-Elements of the present invention.

| SEQ ID NO | Sequence Designation | Source or Origin | Sequence |
|---|---|---|---|
| 17 | CisE7 | GQ14 | ggaggaagca aggtgcgcgt gg |
| 18 | CisE7-Rev | GQ14-Rev | ggtgcgcgtg aacgaagga gg |
| 19 | CisE8 | GQ15 | ggtgggcaaa ggatcacgtg gttgaggtgg |
| 20 | CisE8-Rev | GQ15-Rev | ggtggagttg gtgcactagg aaacgggtgg |
| 21 | CisE9 | GQ16 | ggcataagga cgacagcagg gg |
| 22 | CisE9-Rev | GQ16-Rev | ggggacgaca gcaggaatac gg |
| 23 | CisE10 | GQ17 | ggggcaacct cggacgagca gtcttccagg |
| 24 | CisE10-Rev | GQ17-Rev | ggaccttctg acgagcaggc tccaacgggg |
| 25 | CisE11 | GQ18 | ggttcttgaa cctctgggcc tggttgagg |
| 26 | CisE11-Rev | GQ18-Rev | ggagttggtc cgggtctcca agttcttgg |
| 27 | CisE12 | GQ19 | ggctccggga aaaagaggc cgg |
| 28 | CisE12-Rev | GQ19-Rev | ggccggagaa aaagggcct cgg |
| 29 | CisE13 | GQ20 | ggaaccggaa aggcggg |
| 30 | CisE13-Rev | GQ20-Rev | gggcggaaag gccaagg |
| 31 | CisE14 | GQ22 | gggcgccgac ggagtgggta attcctcgg |
| 32 | CisE14-Rev | GQ22-Rev | ggctccttaa tgggtgaggc agccgcggg |
| 33 | CisE15 | GQ23 | ggaccagtct aggaactggc ttcctgg |
| 34 | CisE15-Rev | GQ23-Rev | ggtccttcgg tcaaggatct gaccagg |
| 35 | CisE16 | GQ24 | ggtgaatccg ggcccggcca tgg |
| 36 | CisE16-Rev | GQ24-Rev | ggtaccggcc cgggcctaag tgg |
| 37 | CisE17 | c-Myc | atggggaggg tggggagggt ggggaaggtg ggga |
| 38 | CisE17-Rev | c-Myc-Rev | aggggtggaa ggggtgggag gggtgggagg ggta |
| 39 | CisE18 | Chicken β-actin | gggggggggg gggcggg |
| 40 | CisE18-Rev | Chicken β-actin-Rev | gggcgggggg ggggggg |
| 41 | CisE19 | VEGF | ggggcgggcc ggggcgggg tcccggggcg g |
| 42 | CisE19-Rev | VEGF-Rev | ggcggggccc tggggcgggg gccgggcggg g |
| 43 | CisE20 | BCL-2 | aggggcgggc gcgggaggaa ggggcgggga gcggggctg |
| 44 | CisE20-Rev | BCL-2-Rev | gtcggggcga gggcggggga aggagggcgc gggcgggga |
| 45 | CisE21 | P5 | ggtcctgtat tagaggtcac gtgagtgttt tgcgacattt tgcgacacca tgtggtcacg ctgggtattt aagcccgagt gagcacgcag ggtctccatt ttgaagcggg aggtttgaac gcgcagccgc catgccgggg ttttacgaga ttgtgattaa ggtccccagc gaccttgacg agcatctgcc cggcatttct gacagctttg tgaactgggt ggccgagaag gaatgggagt |

TABLE 1-continued provides the sequences, sequence designations, and origins of such preferred exemplary Cis-Elements of the present invention.

| SEQ ID NO | Sequence Designation | Source or Origin | Sequence |
|---|---|---|---|
| | | | tgccgccaga ttctgacatg gatctgaatc tgattgagca ggcacccctg accgtggccg agaagctgca gcgcgacttt ctgacggaat ggcgccgtgt gagtaaggcc ccggaggccc ttttctttgt gcaatttgag aagggagaga gctacttcca catgcacgtg ctcgtggaaa ccaccggggt ga |
| 46 | CisE21-Rev | P5-Rev | agtggggcca ccaaaggtgc tcgtgcacgt acaccttcat cgagagaggg aagagtttaa cgtgtttctt ttcccggagg ccccggaatg agtgtgccgc ggtaaggcag tctttcagcg cgacgtcgaa gagccggtgc cagtccccac ggacgagtta gtctaagtct aggtacagtc ttagaccgcc gttgagggta aggaagagcc ggtgggtcaa gtgtttcgac agtctttacg gcccgtctac gagcagttcc agcgacccct ggaattagtg ttagagcatt ttggggccgt accgccgacg cgcaagtttg gagggcgaag ttttacctct gggacgcacg agtgagcccg aatttatggg tcgcactggt gtaccacagc gttttacagc gttttgtgag tgcactggag attatgtcct gg |
| 47 | CisE22 | P19 | gtcacaaaga ccagaaatgg cgccggaggc gggaacaagg tggtggatga gtgctacatc cccaattact tgctccccaa aacccagcct gagctccagt gggcgtggac taatatggaa cagtatttaa gcgcctgttt gaatctcacg gagcgtaaac ggttggtggc gcagcatctg |
| 48 | CisE22-Rev | P19-Rev | gtctacgacg cggtggttgg caaatgcgag gcactctaag tttgtccgcg aatttatgac aaggtataat caggtgcggg tgacctcgag tccgacccaa aacccctcgt tcattaaccc ctacatcgtg agtaggtggt ggaacaaggg cggaggccgc ggtaaagacc agaaacactg |
| 49 | CisE23 | P40 | gtcacaaaga ccagaaatgg cgccggaggt caccaagcag gaagtcaaag acttttttccg gtgggcaaag gatcacgtgg ttgaggtgga gcatgaattc tacgtcaaaa agggtggagc caagaaaaga cccgccccca gtgacgcaga tataagtgag cccaaacggg tgcgcgagtc agttgcgcag ccatcgacgt cagacgcggc gggaacaagg tggtggatga gtgctacatc cccaattact tgctccccaa aacccagcct gagctccagt gggcgtggac taatatggaa cagtatttaa gcgcctgttt gaatctcacg gagcgtaaac ggttggtggc gcagcatctg |
| 50 | CisE23-Rev | P40-Rev | gtctacgacg cggtggttgg caaatgcgag gcactctaag tttgtccgcg aatttatgac aaggtataat caggtgcggg tgacctcgag tccgacccaa aacccctcgt tcattaaccc ctacatcgtg agtaggtggt ggaacaaggg cggcgcagac tgcagctacc gacgcgttga ctgagcgcgt gggcaaaccc gagtgaatat agacgcagtg acccccgccc agaaaagaac cgaggtggga aaaactgcat cttaagtacg aggtggagtt ggtgcactag gaaacgggtg gccttttcca gaaactgaag gacgaaccac tggaggccgc ggtaaagacc agaaacactg |
| 51 | CisE24 | P5(209-331) | cgtgagtgtt ttgcgacatt ttgcgacacc atgtggtcac gctgggtatt taagcccgag tgagcacgca gggtctccat tttgaagcgg gaggtttgaa cgcgcagccg ccatgccggg gtt |

TABLE 1-continued provides the sequences, sequence designations, and origins of such preferred exemplary Cis-Elements of the present invention.

| SEQ ID NO | Sequence Designation | Source or Origin | Sequence |
|---|---|---|---|
| 52 | CisE24-Rev | P5(209-331)-Rev | ttggggccgt accgccgacg cgcaagtttg gagggcgaag ttttacctct gggacgcacg agtgagcccg aatttatggg tcgcactggt gtaccacagc gttttacagc gttttgtgag tgc |
| 53 | CisE25 | P5(317-431) | cgccatgccg gggttttacg agattgtgat taaggtcccc agcgaccttg acgagcatct gcccggcatt tctgacagct ttgtgaactg ggtggccgag aaggaatggg agttg |
| 54 | CisE25-Rev | P5(317-431)-Rev | gttgagggta aggaagagcc ggtgggtcaa gtgtttcgac agtctttacg gcccgtctac gagcagttcc agcgacccct ggaattagtg ttagagcatt ttggggccgt accgc |
| 55 | CisE26 | P5(406-543) | gggtggccga aaggaatgg gagttgccgc cagattctga catggatctg aatctgattg agcaggcacc cctgaccgtg gccgagaagc tgcagcgcga ctttctgacg gaatggcgcc gtgtgagtaa ggccccgg |
| 56 | CisE26-Rev | P5(406-543)-Rev | ggccccggaa tgagtgtgcc gcggtaaggc agtctttcag cgcgacgtcg aagagccggt gccagtcccc acggacgagt tagtctaagt ctaggtacag tcttagaccg ccgttgaggg taaggaagag ccggtggg |
| 57 | CisE27 | P143 | cgttgaaaac caaattgact ccggtcacta cgttttccaa ttttctaaag aatcctttac acacaatgtc aggcggcaag tttagcgcca tcacattctc gtacgtgtac gcccacaatt catcgtgatc caaaatttcg ttttagccg actgagtcaa atatatcatg tagtgtatgc caaaataata gcccaacgat acgcacaatt tggtatcgtc aaagtcaaac caatgattgc aggccctatt aaacactatt ttctcttgtt ttttgtaagg ctcacatcgc ttcaaagctt cattcaaagc ttctttgtcg caggcaaata atgattcaca caaaagttcc aaaaacagtt tgatgtcg |
| 58 | CisE27-Rev | P143-Rev | gctgtagttt gacaaaaacc ttgaaaacac acttagtaat aaacggacgc tgtttcttcg aaacttactt cgaaacttcg ctacactcgg aatgttttt gttctctttt atcacaaatt atcccggacg ttagtaacca aactgaaact gctatggttt aacacgcata gcaacccgat aataaaaccg tatgtgatgt actatataaa ctgagtcagc cgattttgc tttaaaacct agtgctactt aacacccgca tgtgcatgct cttacactac cgcgatttga acggcggact gtaacacaca tttcctaaga aatcttttaa ccttttgcat cactggcctc agttaaacca aaagttgc |
| 59 | CisE28 | CMV | gacattgatt attgactagt tattaatagt aatcaattac ggggtcatta gttcatagcc catatatgga gttccgcgtt acataactta cggtaaatgg cccgcctggc tgaccgccca acgacccccg cccattgacg tcaataatga cgtatgttcc catagtaacg ccaatagga ctttccattg acgtcaatgg gtggagtatt tacggtaaac tgcccacttg gcagtacatc aagtgtatca tatgccaagt acgcccccta ttgacgtcaa tgacggtaaa tggcccgcct ggcattatgc ccagtacatg acctatggg actttcctac ttggcagtac atctacgtat tagtcatcgc tattaccatg gtgatgcggt tttggcagta catcaatggg cgtggatagc ggtttgactc acggggattt ccaagtctcc accccattga cgtcaatggg agtttgtttt ggcaccaaaa tcaacgggac tttccaaaat |

TABLE 1-continued provides the sequences, sequence designations, and origins of such preferred exemplary Cis-Elements of the present invention.

| SEQ ID NO | Sequence Designation | Source or Origin | Sequence |
|---|---|---|---|
| | | | gtcgtaacaa ctccgcccca ttgacgcaaa tgggcggtag gcgtgtacgg tgggaggtct atataagcag |
| 60 | CisE28-Rev | CMV-Rev | gacgaatata tctggagggt ggcatgtgcg gatggcgggt aaacgcagtt accccgcctc aacaatgctg taaaacctttt cagggcaact aaaaccacgg ttttgtttga gggtaactgc agttacccca cctctgaacc tttaggggca ctcagtttgg cgataggtgc gggtaactac atgacggttt tggcgtagtg gtaccattat cgctactgat tatgcatcta catgacggtt catcctttca gggtattcca gtacatgacc cgtattacgg tccgcccggt aaatggcagt aactgcagtt atcccccgca tgaaccgtat actatgtgaa ctacatgacg gttcacccgt caaatggcat ttatgaggtg ggtaactgca gttacctttc agggataacc gcaatgatac ccttgtatgc agtaataact gcagttaccc gcccccagca acccgccagt cggtccgccc ggtaaatggc attcaataca ttgcgccttg aggtatatac ccgatacttg attactgggg cattaactaa tgataattat tgatcagtta ttagttacag |
| 61 | CisE29 | SV40 | gtgtgtcagt tagggtgtgg aaagtcccca ggctcccccag caggcagaag tatgcaaagc atgcatctca attagtcagc aaccaggtgt ggaaagtccc caggctcccc agcaggcaga agtatgcaaa gcatgcatct caattagtca gcaaccatag tcccgcccct aactccgccc atcccgcccc taactccgcc cagttccgcc cattctccgc cccatggctg actaattttt tttatttatg cagaggccga ggccgcctcg gcctctgagc tattccagaa gtagtgagga ggctttttttg gaggcctagg cttttgcaaa |
| 62 | CisE29-Rev | SV40-Rev | aaacgttttc ggatccggag gttttttcgg aggagtgatg aagaccttat cgagtctcgg gctccgccgg agccggagac gtatttattt tttttaatca gtcggtaccc cgcctcttac ccgccttgac ccgcctcaat ccccgcccta cccgcctcaa tccccgccct gataccaacg actgattaac tctacgtacg aaacgtatga agacggacga cccctcggac ccctgaaagg tgtggaccaa cgactgatta actctacgta cgaaacgtat gaagacggac gaccccctcgg acccctgaaa ggtgtgggat tgactgtgtg |
| 63 | CisE30 | RLTR | gcatcaggcg ccgtgcggta tttcacaccg catatggatc catgcatgtt cgaatttaaa tttaattaac atcatcaata atataccttta ttttggattg aagccaatat gataatgagg gggtggagtt tgtgacgtgg cgcggggcgt gggaacgggg cgggtgacgt aggttttagg gcggagtaac ttgtatgtgt tgggaattgt agttttctta aaatgggaag tgacgtaacg tgggaatccg gaggcgcccc tgc |
| 64 | CisE30-Rev | RLTR-Rev | cgtccccgcg gaggcctaag ggtgcaatgc agtgaagggt aaaattcttt tgatgttaag ggttgtgtat gttcaatgag gcgggatttt ggatgcagtg ggcggggcaa gggtgcgggg cgcggtgcag tgtttgaggt ggggagtaa tagtataacc gaagttaggt tttattccat ataataacta ctacaattaa tttaaattta agcttgtacg tacctaggta tacgccacac tttatggcgt gccgcggact acg |
| 65 | CisE31 | GQ4-7 | gggtggccga aaggaatgg gagttgccgc cagattctga catggatctg aatctgattg agcaggcacc cctgaccgtg gccgagaagc tgcagcgcga cttctctgacg gaatggcgcc |

TABLE 1-continued provides the sequences, sequence designations, and origins of such preferred exemplary Cis-Elements of the present invention.

| SEQ ID NO | Sequence Designation | Source or Origin | Sequence |
|---|---|---|---|
| | | | gtgtgagtaa ggccccggag gcccttttct<br>ttgtgcaatt tgagaaggga gagagctact<br>tccacatgca cgtgctcgtg gaaaccaccg<br>gggtgaaatc catggttttg ggacgtttcc<br>tgagtcagat tcgcgaaaaa ctgattcaga<br>gaatttaccg cgggatcgag ccgactttgc<br>caaactggtt cgcggtcaca aagaccagaa<br>atggcgccgg aggcgggaac aaggtggtgg |
| 66 | CisE31-Rev | GQ4-7-Rev | ggtggtggaa caagggcgga ggccgcggta<br>aagaccagaa acactggcgc ttggtcaaac<br>cgtttcagcc gagctagggc gccatttaag<br>agacttagtc aaaaagcgct tagactgagt<br>cctttgcagg gttttggtac ctaaagtggg<br>gccaccaaag gtgctcgtgc acgtacacct<br>tcatcgagag agggaagagt ttaacgtgtt<br>tcttttcccg gaggcccegg aatgagtgtg<br>ccgcggtaag gcagtctttc agcgcgacgt<br>cgaagagccg gtgccagtcc ccacggacga<br>gttagtctaa gtctaggtac agtcttagac<br>cgccgttgag ggtaaggaag agccggtggg |
| 67 | CisE32 | GQ9-12 | ggtcgggtgg ctcgtggaca aggggattac<br>ctcggagaag cagtggatcc aggaggacca<br>ggcctcatac atctccttca atgcggcctc<br>caactcgcgg tcccaaatca aggctgcctt<br>ggacaatgcg ggaaagatta tgagcctgac<br>taaaaccgcc cccgactacc tggtgggcca<br>gcagcccgtg gaggacattt ccagcaatcg<br>gatttataaa attttggaac taaacgggta<br>cgatccccaa tatgcggctt ccgtctttct<br>gggatgggcc acgaaaaagt tcggcaagag<br>gaacaccatc tggctgtttg gg |
| 68 | CisE32-Rev | GQ9-12-Rev | gggtttgtcg gtctaccaca aggagaacgg<br>cttgaaaaag caccgggtag ggtcttttctg<br>ccttcggcgt ataacccta gcatgggcaa<br>atcaaggttt taaatattt aggctaacga<br>cctttacagg aggtgcccga cgaccgggtg<br>gtccatcagc ccccgccaaa atcagtccga<br>gtattagaaa gggcgtaaca ggttccgtcg<br>gaactaaacc ctggcgctca acctccggcg<br>taacttcctc tacatactcc ggaccaggag<br>gacctaggtg acgaagaggc tccattaggg<br>gaacaggtgc tcggtgggct gg |
| 69 | CisE33 | GQ14-15 | ggaggaagca aggtgcgcgt ggaccagaaa<br>tgcaagtcct cggcccagat agacccgact<br>cccgtgatcg tcacctccaa caccaacatg<br>tgcgccgtga ttgacgggaa ctcaacgacc<br>ttcgaacacc agcagccgtt gcaagaccgg<br>atgttcaaat ttgaactcac ccgccgtctg<br>gatcatgact ttgggaaggt caccaagcag<br>gaagtcaaag acttttttccg gtgggcaaag<br>gatcacgtgg ttgaggtgg |
| 70 | CisE33-Rev | GQ14-15-Rev | ggtggagttg gtgcactagg aaacgggtgg<br>ccttttttcag aaactgaagg acgaaccact<br>ggaagggttt cagtactagg tctgccgccc<br>actcaagttt aaacttgtag gccagaacgt<br>tgccgacgac cacaagcttc cagcaactca<br>agggcagtta gtgccgcgtg tacaaccaca<br>acctccactg ctagtgccct cagcccagat<br>agacccggct cctgaacgta aagaccaggt<br>gcgcgtggaa cgaaggagg |
| 71 | CisE34 | GQ16-22 | ggcataagga cgacagcagg ggtcttgtgc<br>ttcctgggta caagtacctc ggaccttca<br>acggactcga caagggagag ccggtcaacg<br>aggcagacgc cgcggccctc gagcacgaca<br>aagcctacga ccggcagctc gacagcggag<br>acaacccgta cctcaagtac aaccacgccg<br>acgcggagtt tcaggagcgc cttaaagaag |

TABLE 1-continued provides the sequences, sequence designations, and origins of such preferred exemplary Cis-Elements of the present invention.

| SEQ ID NO | Sequence Designation | Source or Origin | Sequence |
|---|---|---|---|
| | | | atacgtcttt tgggggcaac ctcggacgag<br>cagtcttcca ggcgaaaaag agggttcttg<br>aacctctggg cctggttgag gaacctgtta<br>agacggctcc gggaaaaaag aggccggtag<br>agcactctcc tgtggagcca gactcctcct<br>cgggaaccgg aaaggcgggc cagcagcctg<br>caagaaaaag attgaatttt ggtcagactg<br>gagacgcaga ctcagtacct gacccccagc<br>ctctcggaca gccaccagca gcccctctg<br>gtctgggaac taatacgatg gctacaggca<br>gtggcgcacc aatggcagac aataacgagg<br>gcgccgacgg agtgggtaat tcctcgg |
| 72 | CisE34-Rev | GQ16-22-Rev | ggctccttaa tgggtgaggc agccgcggga<br>gcaataacag acggtaacca cgcggtgacg<br>gacatcggta gcataatcaa gggtctggtc<br>tcccccgacg accaccgaca ggctctccga<br>cccccagtcc atgactcaga cgcagaggtc<br>agactggttt taagttagaa aaagaacgtc<br>cgacgaccgg gcggaaaggc caagggctcc<br>tcctcagacc gaggtgtcct ctcacgagat<br>ggccggagaa aaaagggcct cggcagaatt<br>gtccaaggag ttggtccggg tctccaagtt<br>cttgggagaa aaagcggacc ttctgacgag<br>caggctccaa cggggttt ctgcatagaa<br>gaaattccgc gaggactttg aggcgcagcc<br>gcaccaacat gaactccatg cccaacagag<br>gcgacagctc gacggccagc atccgaaaca<br>gcacgagctc ccggcgccgc agacggagca<br>actggccgag agggaacagc tcaggcaact<br>tcccaggctc catgaacatg ggtccttcgt<br>gttctgggga cgacagcagg aatacgg |
| 73 | CisE35 | GQ23-25 | ggaccagtct aggaactggc ttcctggacc<br>ctgttaccgc cagcagcgag tatcaaagac<br>atctgcggat aacaacaaca gtgaatactc<br>gtggactgga gctaccaagt accacctcaa<br>tggcagagac tctctggtga atccgggccc<br>ggccatggca agccacaagg acgatgaaga<br>aaagtttttt cctcagagcg gggttctcat<br>ctttgggaag caagg |
| 74 | CisE35-Rev | GQ23-25-Rev | ggaacgaagg gtttctactc ttggggcgag<br>actccttttt tgaaaagaag tagcaggaac<br>accgaacggt accggcccgg gcctaagtgg<br>tctctcagag acggtaactc caccatgaac<br>catcgaggtc aggtgctcat aagtgacaac<br>aacaataggc gtctacagaa actatgagcg<br>acgaccgcca ttgtcccagg tccttcggtc<br>aaggatctga ccagg |

The inclusion of one or more of the Cis-Elements of the present invention increases rAAV production titers. As used herein, the term "production titer" is intended to denote the amount of concentration of infectious rAAV in a preparation. Such amounts or concentrations are preferably determined by titering the AAV or rAAV in such preparation. The production titers of the rAAV preparations of the present invention are preferably titered after subjecting producing cells (e.g., HEK293 transformed with an rAAV plasmid vector, an AAV helper vector providing Rep and Cap proteins, and an Ad helper vector providing required adenovirus transcription and translation factors) to three rounds of freeze/thawing, followed by sonication to release the rAAV particles. The preparation is then centrifuged. The employed AAV helper vector is localized to the supernatant. An aliquot of the preparation is treated with proteinase K, and the number of AAV genomes is determined. An aliquot of the preparation is infected into HeLa-32C2 cells (which express AAV2 Rep and Cap proteins, and infectious titer is measured using the infectious center assay (ICA) (François, A. et al. (2018) "*Accurate Titration of Infectious AAV Particles Requires Measurement of Biologically Active Vector Genomes and Suitable Controls*," Molec. Ther. Meth. Clin. Develop. 10: 223-236) or more preferably, as the median tissue culture infective dose (TCID50) (Zen, Z. et al. (2004) "*Infectious Titer Assay For Adeno-Associated Virus Vectors With Sensitivity Sufficient To Detect Single Infectious Events*," Hum. Gene Ther. 15: 709-715).

As used herein, an rAAV production titer is said to be "increased" by the methods of the present invention if the production titer obtained from the use of the methods of the present invention is at least 10% greater, more preferably at least 20% greater, still more preferably at least 30% greater, still more preferably at least 40% greater, still more preferably at least 50% greater, still more preferably at least 60% greater, still more preferably at least 70% greater, still more preferably at least 80% greater, still more preferably at least 90% greater, still more preferably at least 2-fold greater, still more preferably at least 110% greater, still more preferably at least 120% greater, still more preferably at least 130% greater, still more preferably at least 140% greater, still more preferably at least 2.5-fold greater, still more preferably at least 160% greater, still more preferably at least 170% greater, still more preferably at least 180% greater, still more preferably at least 190% greater, and still more preferably at least 3-fold greater than the titer obtained from a similarly conducted production in which the additionally provided ions were not provided.

The rAAV whose production titer may be increased using the methods of the present invention may comprise any transgene cassette that permits the rAAV to be packaged into an rAAV plasmid vector that may be encapsidated within an AAV capsid particle. Without limitation, such transgene cassette(s) may be of human, primate (including chimpanzee, gibbon, gorilla, orangutan, etc.), cercopithecine (including baboon, cynomolgus monkey, velvet monkey, etc.), canine, glirine (including rat, mouse, hamster, guinea pig, etc.), feline, ovine, caprine, or equine origin.

In preferred embodiments, such an rAAV or rAAV plasmid vector will encode a protein (e.g., an enzyme, hormone, antibody, receptor, ligand, etc.), or comprise a transcribed nucleic acid, that is relevant to a genetic or heritable disease or condition, such that it may be used in gene therapy to treat such disease or condition.

The methods of the present invention may be used to increase the production titer of rAAV and rAAV plasmid vectors in cells that have been transfected with a desired rAAV or rAAV plasmid vector, and with such one or more viruses and/or helper plasmids that can provide proteins or RNA molecules that are not provided by such rAAV or rAAV plasmid vectors, but are required for their production. As discussed above, such proteins or RNA molecules include the genes encoding the Rep52 and Rep78 proteins that are required for vector transcription control and replication, and for the packaging of viral genomes into the viral capsule, and, in the case of rAAV, cap genes that encode VP capsid proteins required to form infectious particles. Such proteins or RNA molecules also include the viral transcription and translation factors (E1a, E1b, E2a, VA and E4) required for AAV proliferation. In one embodiment for producing the rAAV of the present invention, all of these genes and RNA molecules are provided on the same helper virus (or more preferably, helper vector) so as to comprise, in concert with an rAAV, a double plasmid transfection system. More preferably, however, for producing the rAAV of the present invention, the required rep and cap genes are provided by one plasmid, and the genes that encode the viral transcription and translation factors are provided on a second plasmid, so that such plasmids, in concert with the rAAV, comprise a triple plasmid transfection system.

The methods of the present invention may be employed to increase the production titer of rAAV belonging to any serotype, including the AAV1, AAV2, AAV5, AAV6, AAV7, AAV8, AAV9 and AAV10 serotypes and the rAAV1, rAAV2, rAAV5, rAAV6, rAAV7, rAAV8, rAAV9, and rAAV10 serotypes, and including hybrid serotypes (e.g., AAV2/5 and rAAV2/5, which is a hybrid of serotypes 2 and 5 and thus has the trophism of both such serotypes).

The methods of the present invention may be employed to increase the production titers of rAAV that are to be produced using "helper" RNA or proteins provided by an adenovirus, a herpes simplex virus, a cytomegalovirus, a vaccinia virus or a papillomavirus.

The methods of the present invention may be employed to increase the production titers of rAAV produced by cells in adherent monolayer culture or in suspension culture, and may be used with any method capable of producing rAAV. Preferably, however, rAAV is produced by transfecting baby hamster kidney (BHK) cells, or more preferably, human embryonic kidney (HEK) cells grown in tissue culture with the plasmid vectors described above. The BHK cell line BHK-21 (ATCC CCL-10), which lacks endogenous retroviruses is a preferred BHK cell line. The HEK cell line HEK293 (ATCC CRL-1573) and its derivatives, such as HEK293T (ATCC CRL-3216, which is a highly transfectable derivative of the HEK293 cell line into which the temperature-sensitive gene for SV40 T-antigen was inserted) or HEK293T/17 (ATCC® CRL-11268, which was selected for its ease of transfection) are particularly preferred. The HEK293T/17 SF cell line (ATCC ACS-4500) is a derivative of the 293T/17 cell line (ATCC CRL-11268), adapted to serum-free medium and suspension, and may be employed if desired.

The preferred base medium of the present invention for culturing such cells is Eagle's Minimum Essential Medium (ATCC Catalog No. 30-2003) or Dulbecco's Modified Eagle's Medium (DMEM; Mediatech, Manassas, VA). Fetal bovine serum (e.g., FBS; HyClone Laboratories, South Logan, UT) is added to a final concentration of 10% in order to make the complete growth medium. Eagle's Minimum Essential Medium and Dulbecco's Modified Eagle's Medium are complex media that contain amino acids, vitamins, and optionally glucose, in addition to various inorganic salts. The media differ in that Dulbecco's modified Eagle's medium contains approximately four times as much of the vitamins and amino acids present in the original formula of Eagle's Minimum Essential Medium, and two to four times as much glucose. Additionally, it contains iron in the form of ferric sulfate and phenol red for pH indication (Yao, T et al. (2017) "*Animal-Cell Culture Media: History, Characteristics, And Current Issues*," Reproduc. Med. Biol. 16(2): 99-117).

Cells to be used for such transfection are preferably passaged twice weekly to maintain them in exponential growth phase. For small-scale transfections, an aliquot of, for example, $1\times10^6$ HEK293 or BHK cells per well on a multi-well plate, or $1.5\times10^7$ HEK293 cells per 15-cm dish, may be employed. For large-scale production HEK293 or BHK cells may be collected from multiple confluent 15-cm plates, and split into two 10-layer cell stacks (Corning, Corning, NY) containing 1 liter of complete culturing medium. In one embodiment, such cells are grown for 4 days in such medium before transfection. The day before transfection, the two cell stacks may be trypsinized and the cells (e.g., approximately $6\times10^8$ cells) may be resuspended in 200 ml of medium. Preferably, the cells are allowed to attach for 24 hours before transfection. Confluency of the cell stacks may be monitored using a Diaphot inverted microscope (Nikon, Melville, NY) from which the phase-contrast hardware had been removed in order to accommodate the cell stack on the microscope stage.

In particular, the present invention thus provides a method for increasing the production titer of a recombinantly-modified AAV (rAAV) wherein such method comprises the steps:

(A) employing, as the rAAV for producing the production titer, an rAAV that has been modified to comprise an added Cis-Element in one or more of its P1, P2, P3 or P4 Domains, wherein:
  (1) the P1 Domain is 5' to a 5' ITR of the rAAV;
  (2) the P2 Domain is 3' to the 5' ITR of the rAAV and 5' to a transgene cassette of the rAAV;
  (3) the P3 Domain is 3' to the transgene cassette of the rAAV and 5' to a 3' ITR of the rAAV; and
  (4) the P4 Domain is 3' to the 3' ITR of the rAAV; and
(B) culturing cells that have been transfected with the employed rAAV, wherein the cells additionally contain an AAV helper function-providing polynucleotide and a non-AAV helper function-providing polynucleotide, and wherein the culturing is conducted in a culture medium under conditions sufficient to permit the production of rAAV;

wherein the presence of the Cis-Element in the employed rAAV causes the cells to produce the rAAV at an increased production titer relative to that which would be attained if the employed rAAV had lacked the Cis-Element.

II. Pharmaceutical Compositions of the Present Invention

The present invention provides a pharmaceutical composition that comprises:
(A) a preparation of recombinantly-modified adeno-associated virus (rAAV) that comprise a Cis-Element in one or more of its P1, P2, P3 or P4 Domains, wherein:
  (1) the P1 Domain is 5' to a 5' ITR of the rAAV;
  (2) the P2 Domain is 3' to the 5' ITR of the rAAV and 5' to a transgene cassette of the rAAV;
  (3) the P3 Domain is 3' to the transgene cassette of the rAAV and 5' to a 3' ITR of the rAAV; and
  (4) the P4 Domain is 3' to the 3' ITR of the rAAV; and
(B) a pharmaceutically acceptable carrier.

The invention additionally includes pharmaceutical compositions that comprise a pharmaceutically acceptable preparation of rAAV produced in accordance with the methods of the present invention, and a pharmaceutically acceptable carrier. The rAAV of such pharmaceutical compositions comprises a transgene cassette that encodes a protein, or comprises a transcribed nucleic acid, that is therapeutic for a genetic or heritable disease or condition, and is present in such pharmaceutical composition in an amount effective to ("effective amount")

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Suitable pharmaceutical excipients are described in U.S. Pat. Nos. 8,852,607; 8,192,975; 6,764,845; 6,759,050; and 7,598,070.

Generally, the ingredients of compositions of the invention are supplied either separately or mixed together in unit dosage form, for example, as a dry lyophilized powder or water-free concentrate, or as an aqueous solution in a hermetically sealed container such as a vial, an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline, or other diluent can be provided so that the ingredients may be mixed prior to administration.

The invention also provides a pharmaceutical pack or kit comprising one or more containers such pharmaceutical composition. Optionally associated with such container(s) can be a notice in the form prescribed by a governmental agency regulating the manufacture, use or sale of pharmaceuticals or biological products, which notice reflects approval by the agency of manufacture, use or sale for human administration.

The rAAV of such pharmaceutical compositions is preferably packaged in a hermetically sealed container, such as a vial, an ampoule or sachette indicating the quantity of the molecule, and optionally including instructions for use. In one embodiment, the rAAV of such kit is supplied as a dry sterilized lyophilized powder or water-free concentrate in a hermetically sealed container and can be reconstituted, e.g., with water, saline, or other diluent to the appropriate concentration for administration to a subject. The lyophilized material should be stored at between 2° C. and 8° C. in their original container and the material should be administered within 12 hours, preferably within 6 hours, within 5 hours, within 3 hours, or within 1 hour after being reconstituted. In another embodiment, the rAAV of such kit is supplied as an aqueous solution in a hermetically sealed container and can be diluted, e.g., with water, saline, or other diluent, to the appropriate concentration for administration to a subject. The kit can further comprise one or more other prophylactic and/or therapeutic agents useful for the treatment of the disease or condition, in one or more containers; and/or the kit can further comprise one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

III. Uses of the Invention

The methods of the present invention may be used to facilitate the production of rAAV, and may particularly be used to facilitate the production of rAAV that comprise transgene cassettes that encode a protein (e.g., an enzyme, hormone, antibody, receptor, ligand, etc.), or of rAAV that comprise a transcribed nucleic acid, that is relevant to a genetic or heritable disease or condition, such that it may be used in gene therapy to treat such disease or condition. Examples of such diseases and conditions include: achromatopsia (ACHM); alpha-1 antitrypsin (AAT) deficiency; Alzheimer's Disease; aromatic L-amino acid decarboxylase (AADC) deficiency; choroideremia (CHM); cancer; Duchenne muscular dystrophy; dysferlin deficiency; follistatin gene deficiency (BMDSIBM); hemophilia A; hemophilia B; hepatitis A; hepatitis B; hepatitis C; Huntington's disease; idiopathic Parkinson's disease; late-infantile neuronal ceroid lipofuscinosis (LINCL, an infantile form of Batten disease); Leber congenital amaurosis (LCA); Leber's hereditary optic neuropathy (LHON); limb girdle muscular dystrophy 1B (LGMD1B); limb girdle muscular dystrophy 1C (LGMD1C); limb girdle muscular dystrophy 2A (LGMD2A); limb girdle muscular dystrophy 2B (LGMD2B); limb girdle muscular dystrophy 2I (LGMD2I); limb girdle muscular dystrophy 2L (LGMD2L); lipoprotein lipase (LPL) deficiency; metachromatic leukodystrophy; neurological disability; neuromotor deficit; neuroskeletal impairment; Parkinson's disease; rheumatoid arthritis; Sanfilippo A syndrome; spinal muscular atrophy (SMA); X-linked retinoschisis (XLRS); α-sarcoglycan deficiency (LGMD2D); β-sarcoglycan deficiency (LGMD2E); γ-sarcoglycan deficiency (LGMD2C) and δ-sarcoglycan deficiency (LGMD2F).

IV. Embodiments of the Invention

The invention concerns a recombinantly-modified adeno-associated virus (AAV) helper vector that comprises an AAV helper function-providing polynucleotide, and uses and compositions thereof. It is particularly directed to the following embodiments E1-E22:

E1. A recombinantly-modified adeno-associated virus (rAAV) that comprises a Cis-Element in one or more of its P1, P2, P3 or P4 Domains, wherein:
(1) the P1 Domain is 5' to a 5' ITR of the rAAV;
(2) the P2 Domain is 3' to the 5' ITR of the rAAV and 5' to a transgene cassette of the rAAV;
(3) the P3 Domain is 3' to the transgene cassette of the rAAV and 5' to a 3' ITR of the rAAV; and
(4) the P4 Domain is 3' to the 3' ITR of the rAAV; and
wherein the presence of the Cis-Element causes rAAV-producing cells to produce the rAAV at a higher production titer than would be attained with such rAAV if lacking the Cis-Element.

E2. A pharmaceutical composition that comprises:
(A) a preparation of recombinantly-modified adeno-associated virus (rAAV) that comprise a Cis-Element in one or more of its P1, P2, P3 or P4 Domains, wherein:
(1) the P1 Domain is 5' to a 5' ITR of the rAAV;
(2) the P2 Domain is 3' to the 5' ITR of the rAAV and 5' to a transgene cassette of the rAAV;
(3) the P3 Domain is 3' to the transgene cassette of the rAAV and 5' to a 3' ITR of the rAAV; and
(4) the P4 Domain is 3' to the 3' ITR of the rAAV; and
(B) a pharmaceutically acceptable carrier.

E3. A method for increasing the production titer of recombinantly-modified adeno-associated virus (rAAV), wherein the method comprises:
(A) employing, as the rAAV for producing the production titer, an rAAV that has been modified to comprise an added Cis-Element in one or more of its P1, P2, P3 or P4 Domains, wherein:
(1) the P1 Domain is 5' to a 5' ITR of the rAAV;
(2) the P2 Domain is 3' to the 5' ITR of the rAAV and 5' to a transgene cassette of the rAAV;
(3) the P3 Domain is 3' to the transgene cassette of the rAAV and 5' to a 3' ITR of the rAAV; and
(4) the P4 Domain is 3' to the 3' ITR of the rAAV; and (B) culturing cells that have been transfected with the employed rAAV, wherein the cells additionally contain an AAV helper function-providing polynucleotide and a non-AAV helper function-providing polynucleotide, and wherein the culturing is conducted in a culture medium under conditions sufficient to permit the production of rAAV; wherein the presence of the Cis-Element in the employed rAAV causes the cells to produce the rAAV at an increased production titer relative to that which would be attained if the employed rAAV had lacked the Cis-Element.

E4. The recombinantly-modified adeno-associated virus (rAAV) of E1, the pharmaceutical composition of E2, or the method of E3, wherein the employed rAAV has been modified to comprise an added Cis-Element in its P1 Domain.

E5. The recombinantly-modified adeno-associated virus (rAAV) of E1, the pharmaceutical composition of E2, or the method of E3, wherein the employed rAAV has been modified to comprise an added Cis-Element in its P2 Domain.

E6. The recombinantly-modified adeno-associated virus (rAAV) of E1, the pharmaceutical composition of E2, or the method of E3, wherein the employed rAAV has been modified to comprise an added Cis-Element in its P3 Domain.

E7. The recombinantly-modified adeno-associated virus (rAAV) of E1, the pharmaceutical composition of E2, or the method of E3, wherein the employed rAAV has been modified to comprise an added Cis-Element in its P4 Domain.

E8. The recombinantly-modified adeno-associated virus (rAAV) of E1, the pharmaceutical composition of E2, or the method of E3, wherein the employed rAAV has been modified to comprise an added Cis-Element in its P1 Domain and in one or more of its P2, P3 or P4 Domain.

E9. The recombinantly-modified adeno-associated virus (rAAV) of E1, the pharmaceutical composition of E2, or the method of E3, wherein the employed rAAV has been modified to comprise an added Cis-Element in its P2 Domain and in one or more of its P3 or P4 Domain.

E10. The recombinantly-modified adeno-associated virus (rAAV) of E1, the pharmaceutical composition of E2, or the method of E3, wherein the employed rAAV has been modified to comprise an added Cis-Element in its P3 Domain and in its P4 Domain.

E11. The recombinantly-modified adeno-associated virus (rAAV) of any one of E1 or E4-E10, the pharmaceutical composition of any one of E2 or E4-E10, or the method of any one of E3-E10, wherein the added Cis-Element forms a G-Quadruplex Structure in the employed rAAV.

E12. The recombinantly-modified adeno-associated virus (rAAV) of any one of E1 or E4-E11, the pharmaceutical composition of any one of E2 or E4-E11, or the method of any one of E3-E11, wherein an added Cis-Element is selected from the group consisting of:
(1) a Potential G-Quadruplex Sequence of a wild type AAV genome or a Potential G-Quadruplex Sequence of a wild type AAV genome in a reversed orientation;
(2) an Actual G-Quadruplex Sequence of a wild type AAV genome or an Actual G-Quadruplex Sequence of a wild type AAV genome in a reversed orientation;

(3) a DNA sequence from wild-type AAV or a DNA sequence from wild-type AAV in a reversed orientation; and (4) a DNA sequence from another viral genome or a DNA sequence from another viral genome in a reversed orientation.

E13. The recombinantly-modified adeno-associated virus (rAAV) of any one of E1 or E4-E12, the pharmaceutical composition of any one of E2 or E4-E12, or the method of any one of E3-E12, wherein the transgene cassette encodes a protein, or comprises a transcribed nucleic acid, that is therapeutic for a genetic or heritable disease or condition.

E14. The recombinantly-modified adeno-associated virus (rAAV) of any one of E1 or E4-E13, the pharmaceutical composition of any one of E2 or E4-E13, or the method of any one of E3-E13, wherein the employed rAAV belongs to the rAAV1, rAAV2, rAAV5, rAAV6, rAAV7, rAAV8, rAAV9 or rAAV10 serotype, or to a hybrid of the serotypes.

E15. The recombinantly-modified adeno-associated virus, the pharmaceutical composition, or the method of E14, wherein the employed rAAV belongs to the rAAV2, rAAV5, or rAAV9 serotype, or to a hybrid of the serotypes.

E16. The recombinantly-modified adeno-associated virus (rAAV) of any one of E1 or E4-E15, or the method of any one of E3-E15, wherein the cells are human embryonic kidney cells.

E17. The recombinantly-modified adeno-associated virus (rAAV) of E16, or the method of E16, wherein the cells are human embryonic kidney cells.

E18. The recombinantly-modified adeno-associated virus (rAAV) of E17, or the method of E17, wherein the are HEK293 cells.

E19. The recombinantly-modified adeno-associated virus (rAAV) of E16, or the method of E16, wherein the cells are baby hamster kidney cells.

E20. The recombinantly-modified adeno-associated virus (rAAV) of E19, or the method of E19, wherein the are BHK21 cells.

E21. The recombinantly-modified adeno-associated virus (rAAV) of E16, or the method of E16, wherein the cells are sf9 insect cells.

E22. The preparation of recombinantly-modified adeno-associated virus (rAAV) of E14, or the pharmaceutical composition of E15, wherein the transgene cassette encodes a protein, or comprises a transcribed nucleic acid, that is therapeutic for a genetic or heritable disease or condition, for use in the treatment of the genetic or heritable disease or condition.

EXAMPLES

Having now generally described the invention, the same will be more readily understood through reference to the following examples, which are provided by way of illustration and are not intended to be limiting of the present invention unless specified.

Example 1

Comparison of rAAV Production Titers by Cells Transfected With rAAV Plasmid Vectors Having a Cis-Element Within the rAAV Plasmid Vector's P2 Domain In order to demonstrate the ability of the Cis-Elements of the present invention to increase rAAV production titers, the parent rAAV plasmid vector pAV-TBG-EGFP was modified to contain a cis element within its P2 Domain.

Figure 1:
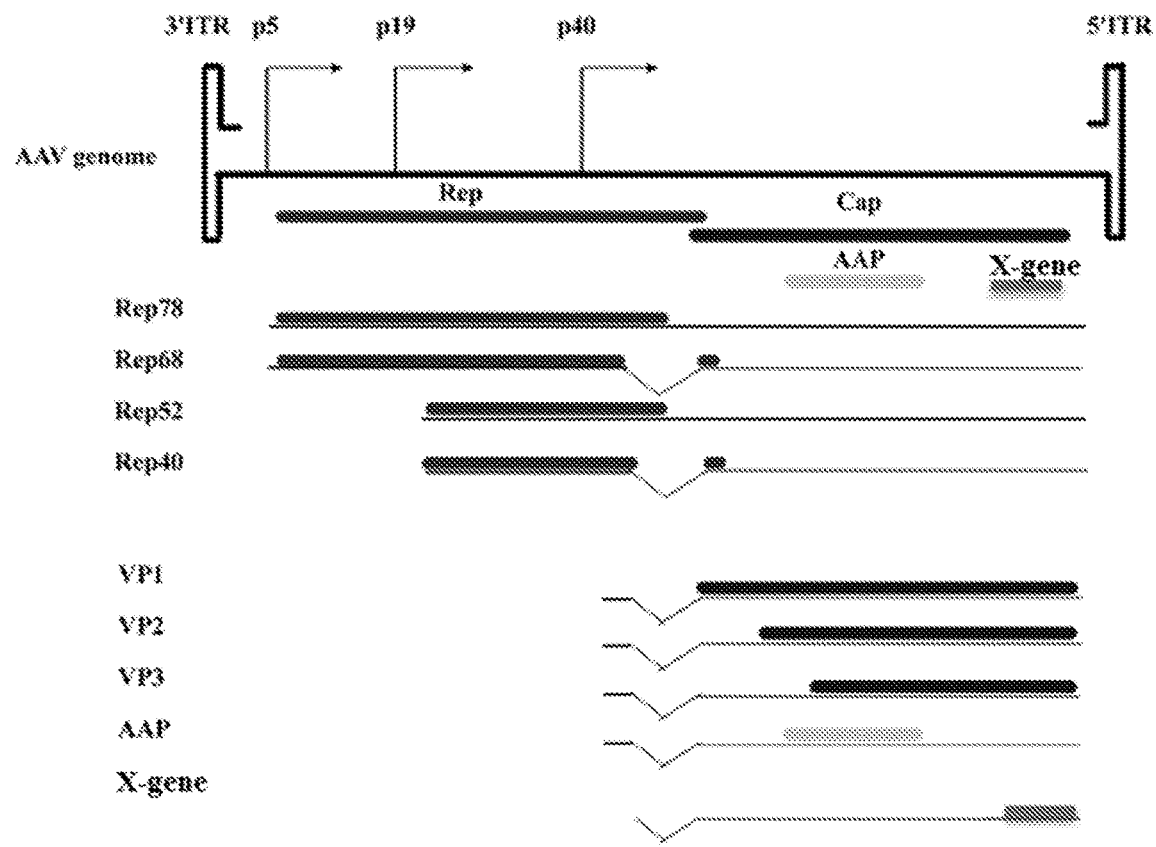
FIG. 1 provides a schematic genetic map of the wild-type (Wt) AAV genome.
Figure 2:
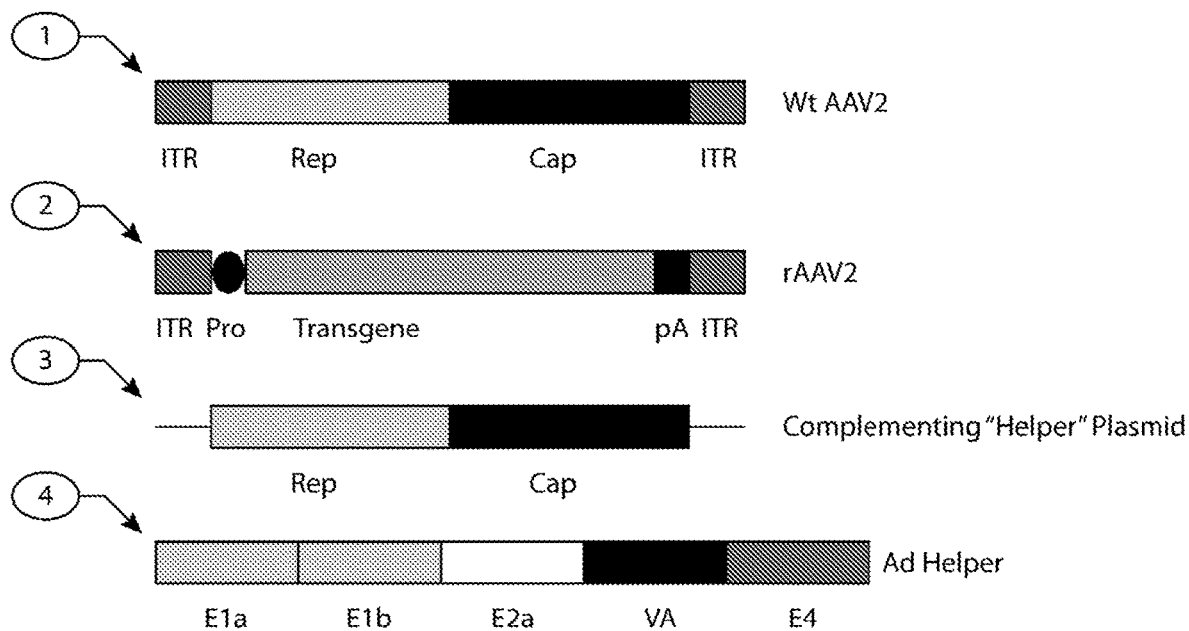
FIG. 2 provides a schematic of the structural domain of the wild-type AAV2 genome (1), a recombinant AAV (rAAV) (2), complementing "AAV helper plasmid" (3) and an adenovirus helper plasmid ("Ad helper plasmid") (4). The wild-type (Wt) AAV2 (1) is composed of AAV-specific palindromic inverted terminal repeated sequences (ITR), a 5' half containing genes that encode the Rep proteins and a 3' half containing genes that encode the Cap proteins. The rAAV (2) is formed by replacing the Rep- and Cap-encoding genes of the wild-type (Wt) AAV2 (1) with a transgene cassette that comprises a promoter (Pro), the exogenous transgene of interest, and a polyadenylation site (pA). In order to produce the rAAV (2), a complementing "AAV helper" plasmid vector (3) and an adenovirus helper plasmid vector (Ad helper plasmid) (4) are provided. The complementing AAV helper plasmid (3) provides Rep and Cap proteins. The Ad helper plasmid (4) provides adenovirus proteins E1a, E1b, E2a, VA and E4.
Figure 3A:
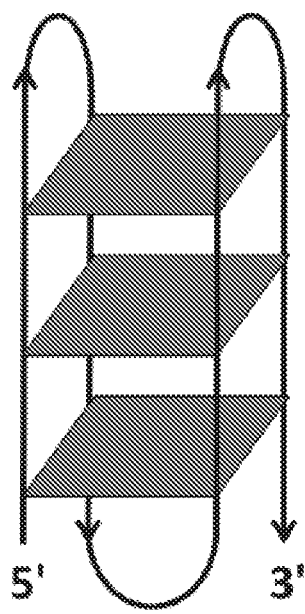
FIGS. 3A-3D show illustrative G-Quadruplex Structures formed by the stacking of multiple G-tetrads.
Figure 3B:
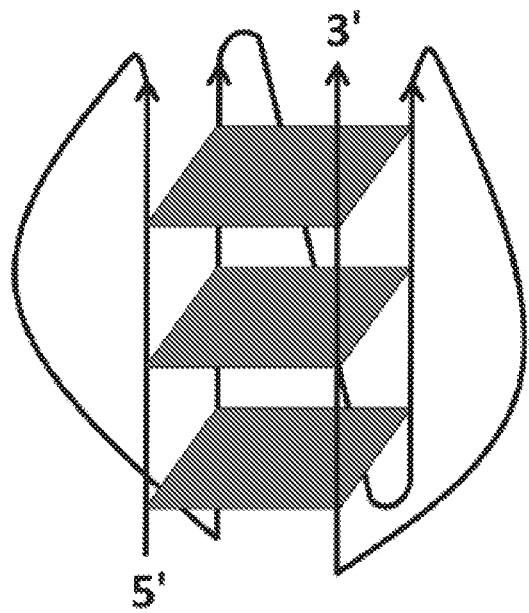
Figure 3C:
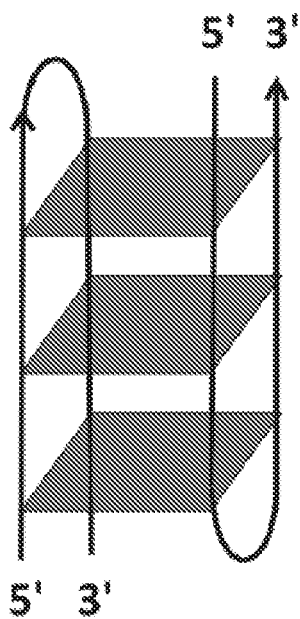
Figure 3D:
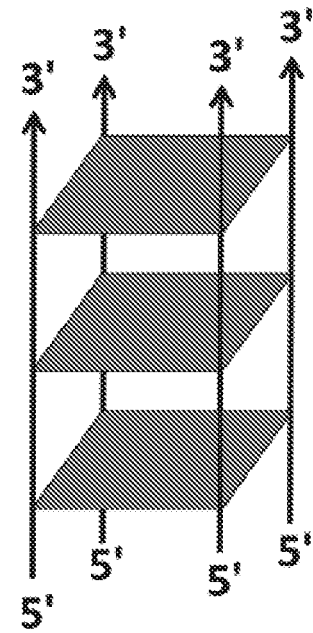
Figure 9A:
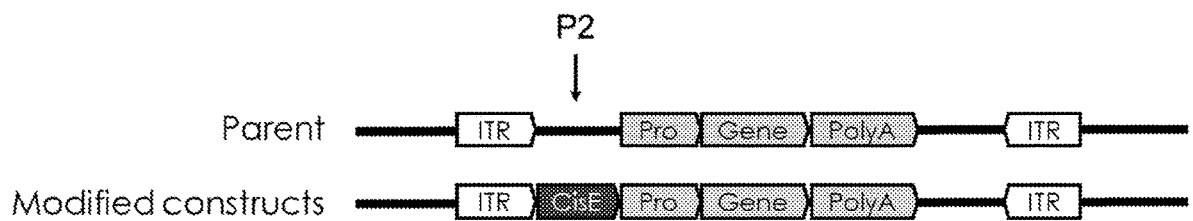
FIGS. 9A-9B show the increase in rAAV production titers obtained by introducing a Cis-Element within the P2 Domain of the rAAV plasmid vector pAV-TBG-EGFP.

A series of 27 derivatives of plasmid pAV-TBG-EGFP were constructed by inserting one of Cis-Element CisE1-CisE27 (Table 1) into the SpeI site of the plasmid that is located within the plasmid's P2 Domain (FIG. 7; FIG. 9A). The production titers of rAAV obtained using the derivative plasmids in a triple plasmid transfection system (FIG. 2) with the AAV helper plasmid pRC2 providing the AAV rep and cap functions and the Ad helper plasmid pHelper that provided the required adenoviral functions were measured and compared to those obtained with the parental pAV-TBG-EGFP plasmid.

Figure 9B:
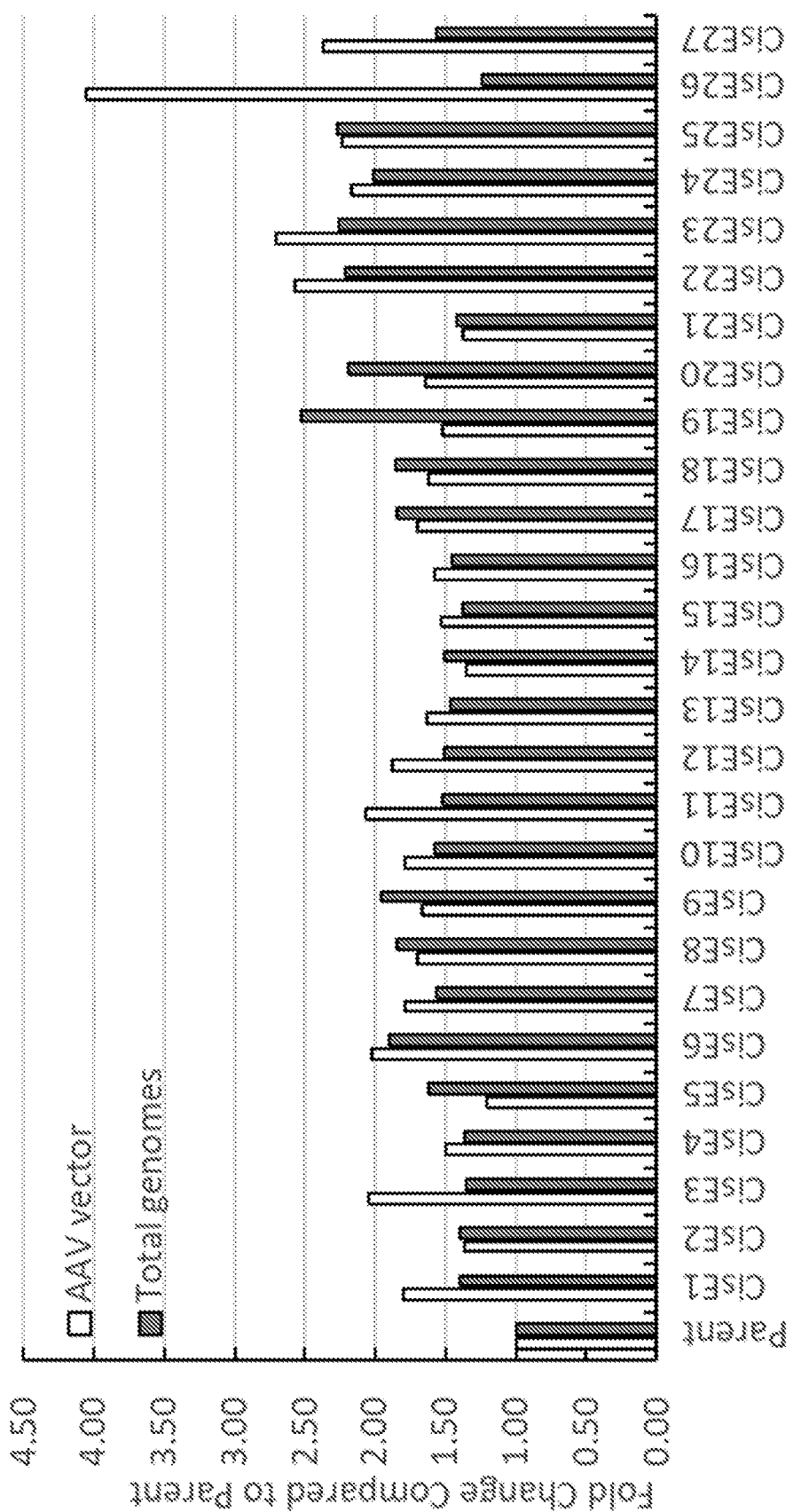

The results of the investigation are shown in FIG. 9B, and indicate that all of the Cis-Elements introduced within the P2 Domain of the rAAV plasmid vector pAV-TBG-EGFP resulted in an increase in rAAV production titer. The insertion of CisE19 into the P2 Domain of the rAAV plasmid vector was found to mediate a 2.5-fold increase in production titer. The insertion of CisE26 into the P2 Domain of the rAAV plasmid vector was found to mediate a 4-fold increase in production titer.

Example 2

Comparison of rAAV Production Titers by Cells Transfected With rAAV Plasmid Vectors Having a Cis-Element Within the rAAV Plasmid Vector's P1 Domain In order to further demonstrate the ability of the Cis-Elements of the present invention to increase rAAV production titers, the rAAV plasmid vector, pAV-TBG-EGFP was modified to contain a Cis-Element within the plasmid's P1 Domain. The effect of that modification on rAAV titer was then assessed as described above.

Figure 10A:
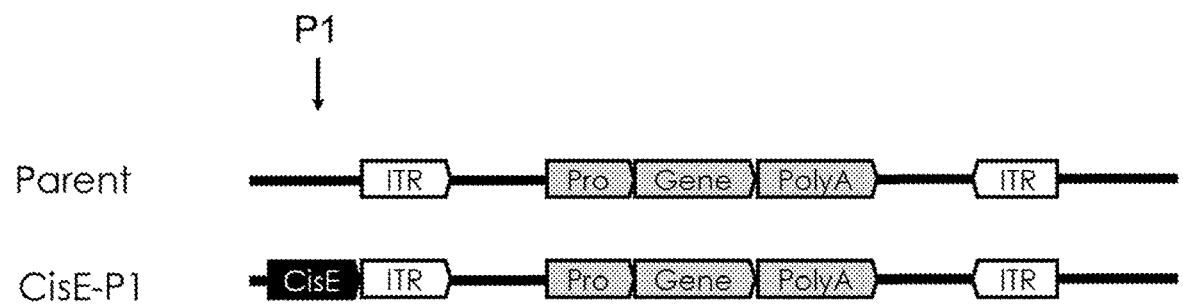
FIGS. 10A-10B show the increase in rAAV production titers obtained by introducing a Cis-Element within the P1 Domain of the rAAV plasmid vector pAV-TBG-EGFP (FIG. 10A).
Figure 10B:
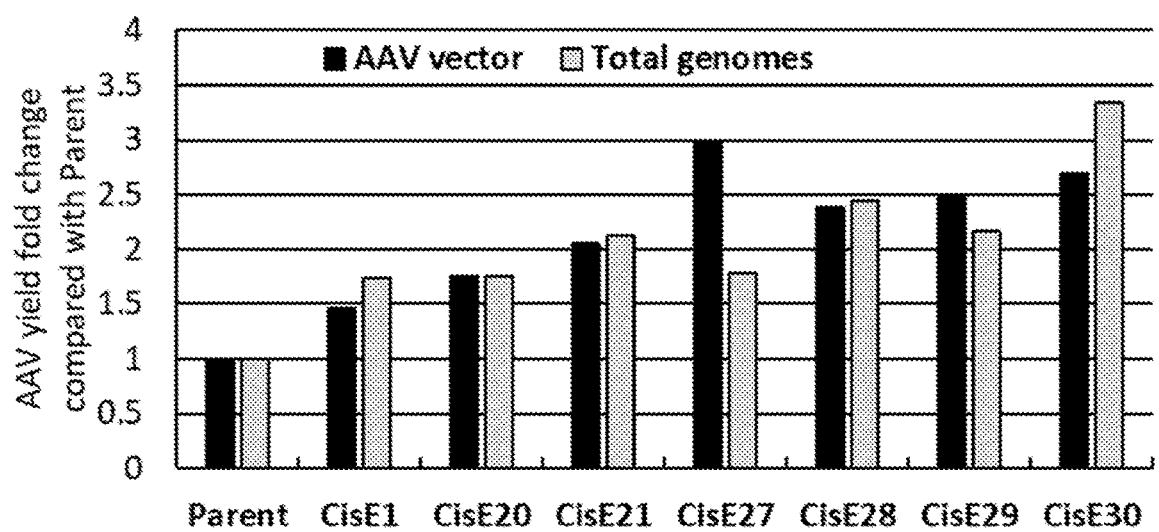

More specifically, a series of 7 derivatives of rAAV plasmid vector pAV-TBG-EGFP were constructed by inserting one of Cis-Element CisE1, CisE20, CisE21, CisE27, CisE28, CisE29, or CisE30 (Table 1) into the PciI site of the plasmid that is located within the plasmid's P1 Domain (FIG. 7; FIG. 10A). The production titers of rAAV were obtained essentially as described in Example 1 using a triple plasmid transfection system (FIG. 2) with an AAV helper plasmid providing the AAV rep and cap functions (pHelper-Kan) and an Ad helper plasmid that provided the required adenoviral functions (pRC2). The production titers were compared with those obtained with the parental pAV-TBG-EGFP plasmid. The results of the investigation are shown in FIG. 10B, and indicate that all of the Cis-Elements introduced within the P1 Domain of pAV-TBG-EGFP resulted in an increase in rAAV production titer. The insertion of CisE30 within the P1 Domain of the rAAV plasmid vector was found to mediate a 3.0-fold increase in production titer.

Example 3

Figure 11A:
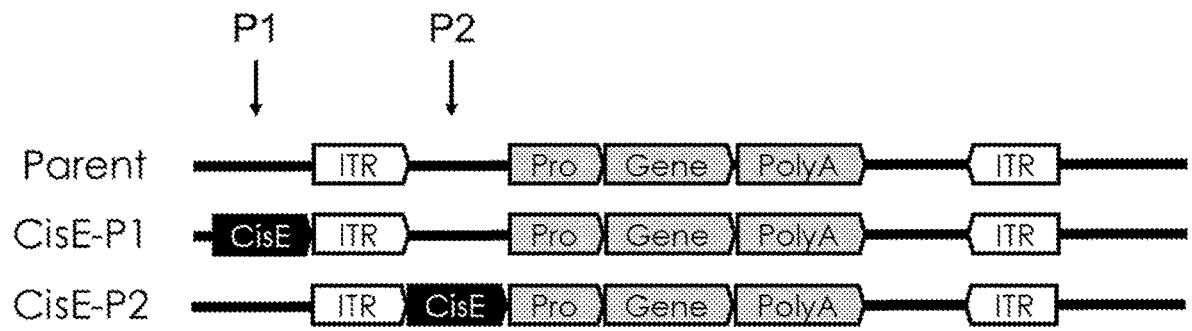
FIGS. 11A-11B show the increase in rAAV production titers obtained by introducing the same Cis-Element within the P1 Domain or P2 Domain of the rAAV plasmid vector pAV-TBG-EGFP (FIG. 11A).

Comparison of rAAV Production Titers by Cells Transfected with rAAV Plasmid Vectors Having a Cis-Element within Either the rAAV Plasmid Vector's P1 Domain or P2 Domain The effect on rAAV production titers of inserting the same Cis-Element either within the P1 Domain of an rAAV plasmid vector or within the P2 Domain of such rAAV plasmid vector was investigated by introducing Cis-Element CisE1, CisE20 or CisE21 into either the P1 Domain of the rAAV plasmid vector pAV-TBG-EGFP or within the P2 Domain of plasmid vector pAV-TBG-EGFP (FIG. 11A), essentially as described above.

Figure 11B:
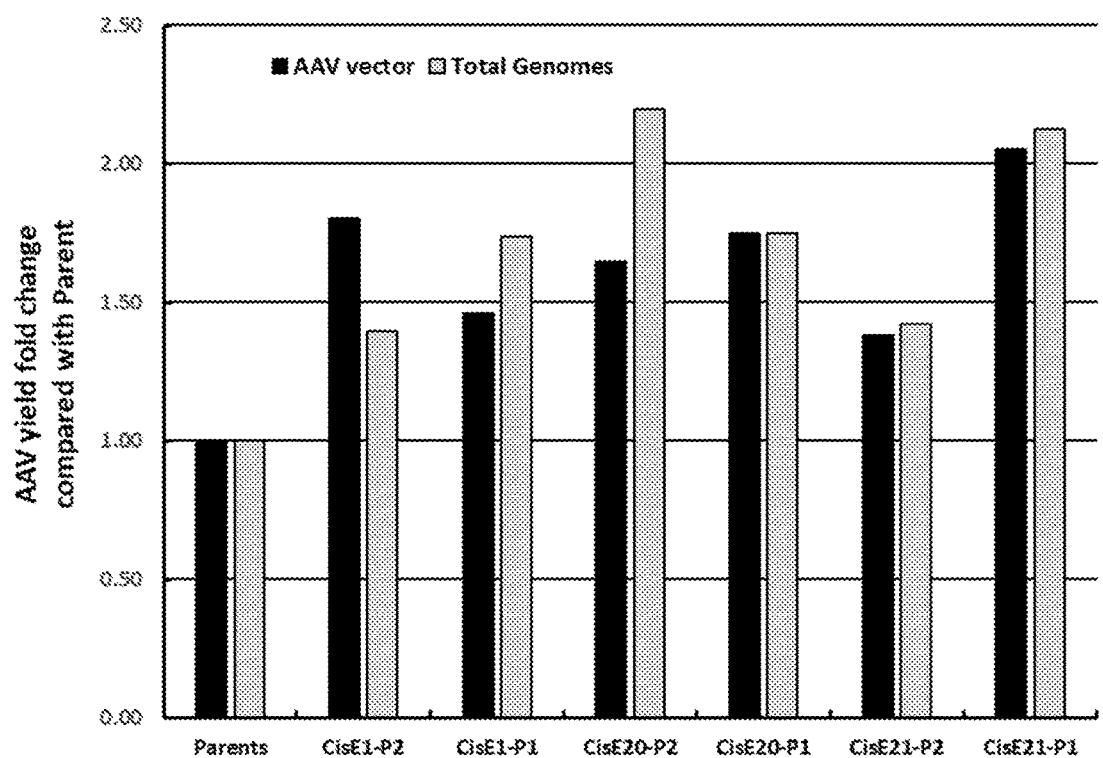

The production titers of rAAV were obtained essentially as described in Example 1 using a triple plasmid transfection system (FIG. 2) with an AAV helper plasmid providing the AAV rep and cap functions (pHelper) and an Ad helper plasmid that provided the required adenoviral functions (pRC2). The results of the investigation are shown in FIG. 11B, and indicate that positioning a Cis-Element within either the P1 or P2 Domain of an rAAV plasmid vector resulted in an increase in rAAV production titer.

Example 4

Figure 12A:
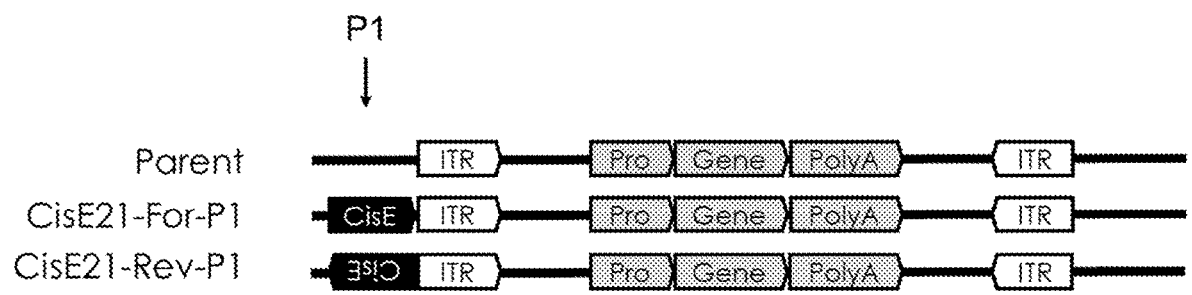
FIGS. 12A-12B show the effect of Cis-Element orientation on the ability of a Cis-Element, inserted within the P1 Domain the rAAV plasmid vector pAV-TBG-EGFP, to cause an increase in rAAV production titer (FIG. 12A).

Effect of Orientation of Cis-Elements in an rAAV Plasmid Vector on rAAV Yield Produced by Transfected Cells The effect of the orientation of a Cis-Element in an rAAV plasmid vector on rAAV production titers was investigated by inserting the Cis-Element CisE21 (Table 1) within the P1 Domain of the rAAV plasmid vector pAV-TBG-EGFP in either the "forward" orientation (SEQ ID NO:45) or in the "reverse" orientation (SEQ ID NO:46) (FIG. 12A), essentially as described above.

Figure 12B:
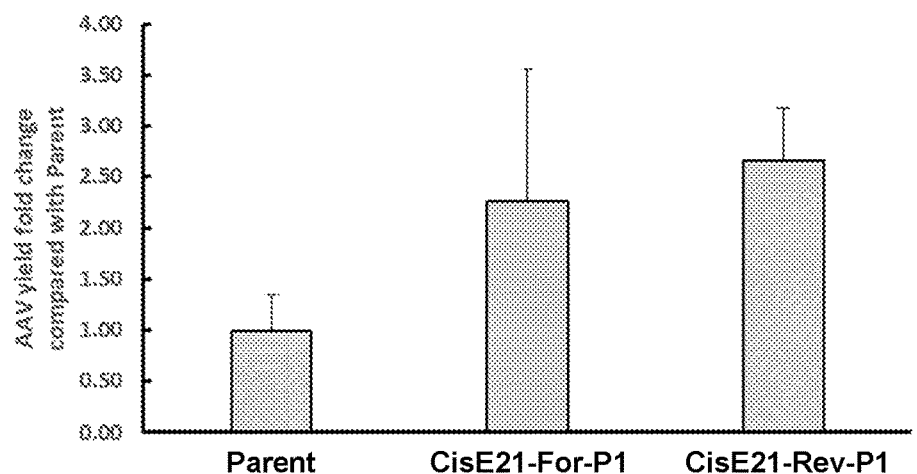

The production titers of rAAV were obtained essentially as described in Example 1 using a triple plasmid transfection system (FIG. 2) with an AAV helper plasmid (pRC2) providing the AAV rep and cap functions and an Ad helper plasmid (pHelper) that provided the required adenoviral functions. The results of the investigation are shown in FIG. 12B, and indicate that an increased rAAV production titer was obtained using rAAV plasmid vectors having either orientation of the inserted Cis-Element.

Example 5

Figure 13A:
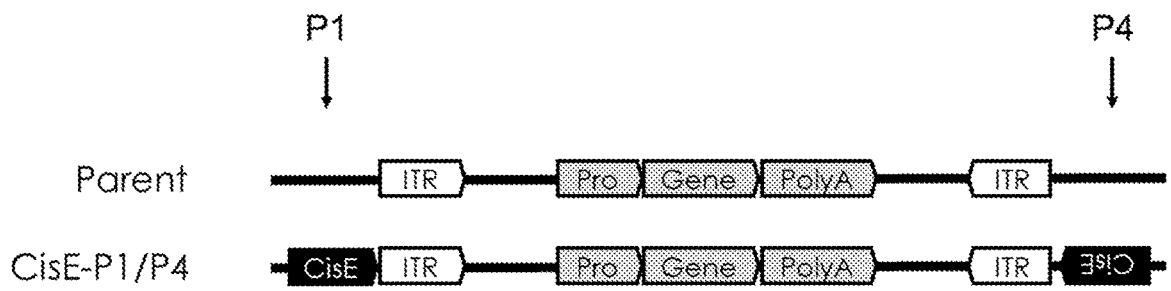
FIGS. 13A-13D show the effect of Cis-Element orientation on the ability of a Cis-Element, inserted within both the P1 Domain the rAAV plasmid vector pAV-TBG-EGFP and the P4 Domain of such plasmid vector to cause an increase in rAAV production titer (FIG. 13A).

Comparison of rAAV Production Titers by Cells Transfected with rAAV Plasmid Vectors Having a Cis-Element within the rAAV Plasmid Vector's P1 Domain and its P4 Domain The effect on rAAV production titers of inserting different Cis-Elements within the P1 Domain of an rAAV plasmid vector, while maintaining the same Cis-Element within the P4 Domain of such rAAV plasmid vector (FIG. 13A), was investigated by introducing different Cis-Elements within the P1 Domain of an rAAV plasmid vector that contained the same Cis-Element in the KasI site that is located within the P4 Domain of such rAAV plasmid vector. The production titers of rAAV were obtained essentially as described in Example 1 using a triple plasmid transfection system (FIG. 2) with an AAV helper plasmid providing the AAV rep and cap functions and an Ad helper plasmid that provided the required adenoviral functions.

Figure 13B:
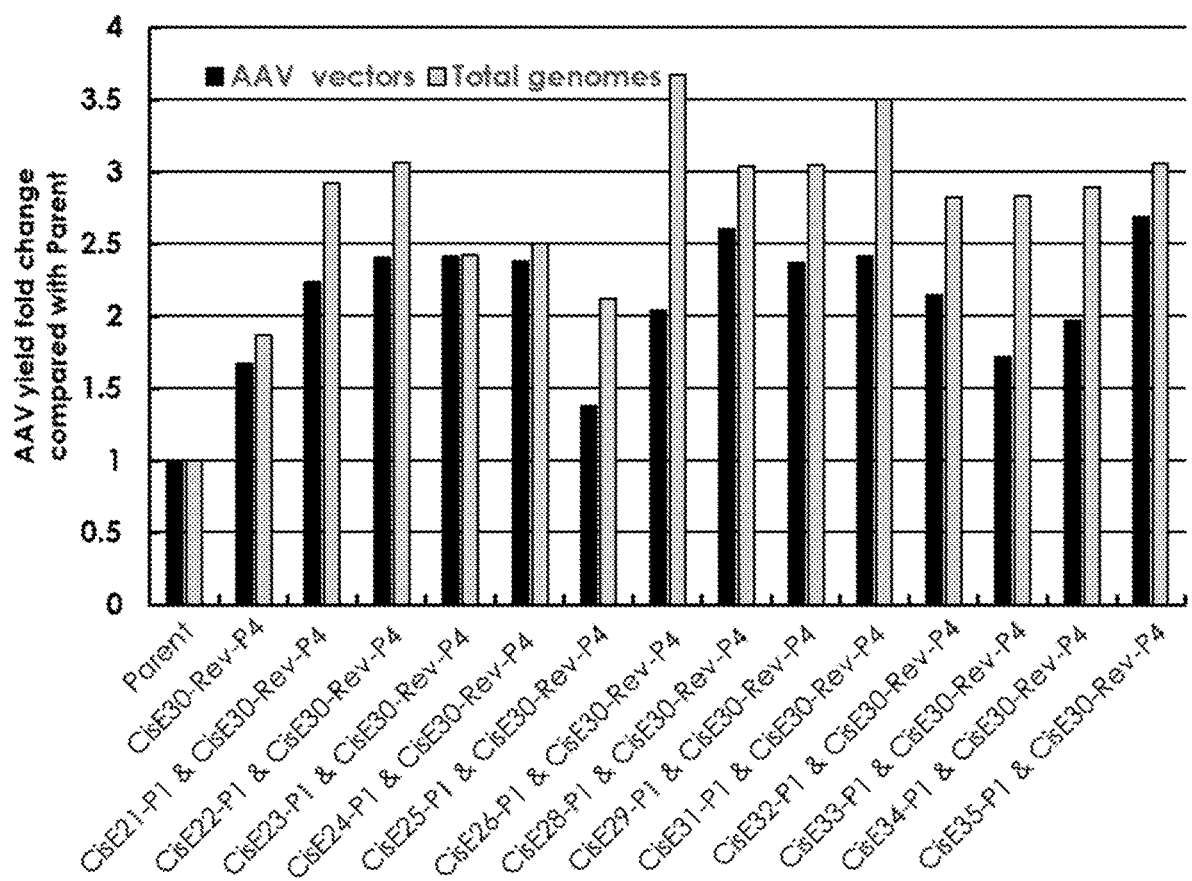
Figure 13C:
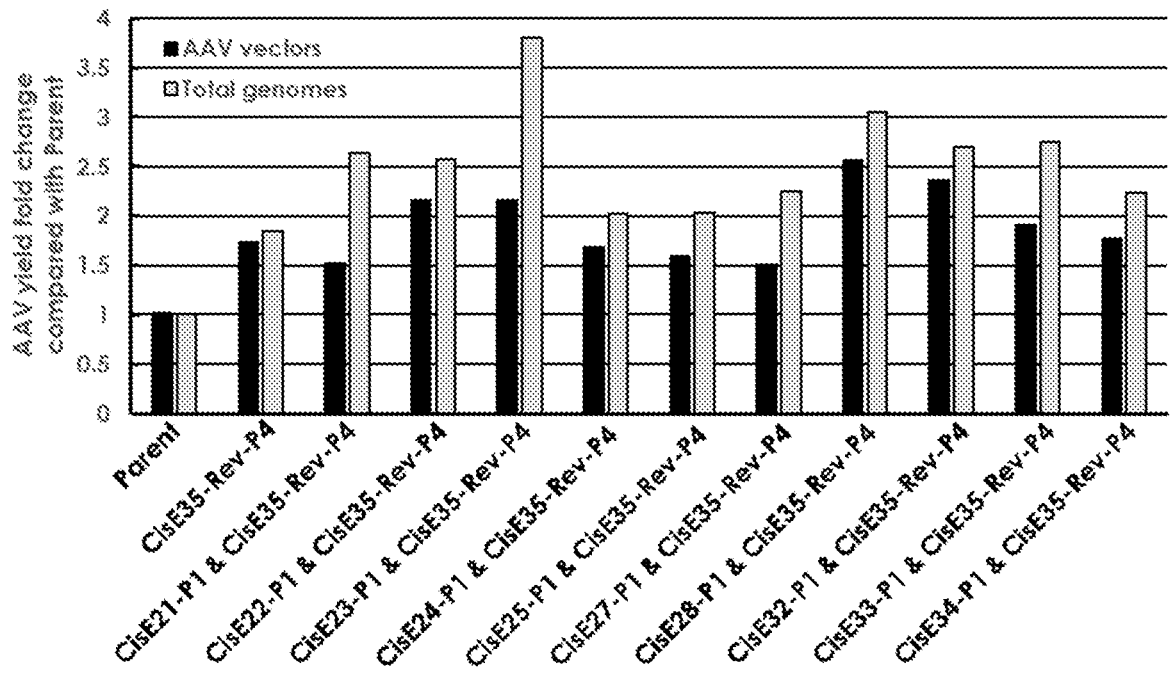

The results of the investigation are shown in FIG. 13B and FIG. 13C. FIG. 13B shows the production titers of rAAV that were obtained using plasmid vector pAV-TBG-EGFP that contained Cis-Element CisE21, CisE22, CisE23, CisE24, CisE25, CisE26, CisE28, CisE29, CisE31, CisE32, CisE33, CisE34, or CisE35 within its P1 Domain and Cis-Element CisE30-Rev within its P4 Domain. FIG. 13C shows the production titers of rAAV that were obtained using plasmid vector pAV-TBG-EGFP that contained Cis-Element CisE21, CisE22, CisE23, CisE24, CisE25, CisE27, CisE28, CisE32, CisE33, or CisE34 within its P1 Domain and Cis-Element CisE35-Rev within its P4 Domain. The results of the investigation indicate that the presence of two Cis-Elements in the rAAV plasmid vectors synergistically enhanced the increased production titer, relative to that obtained using only a single Cis-Element.

Figure 13D:
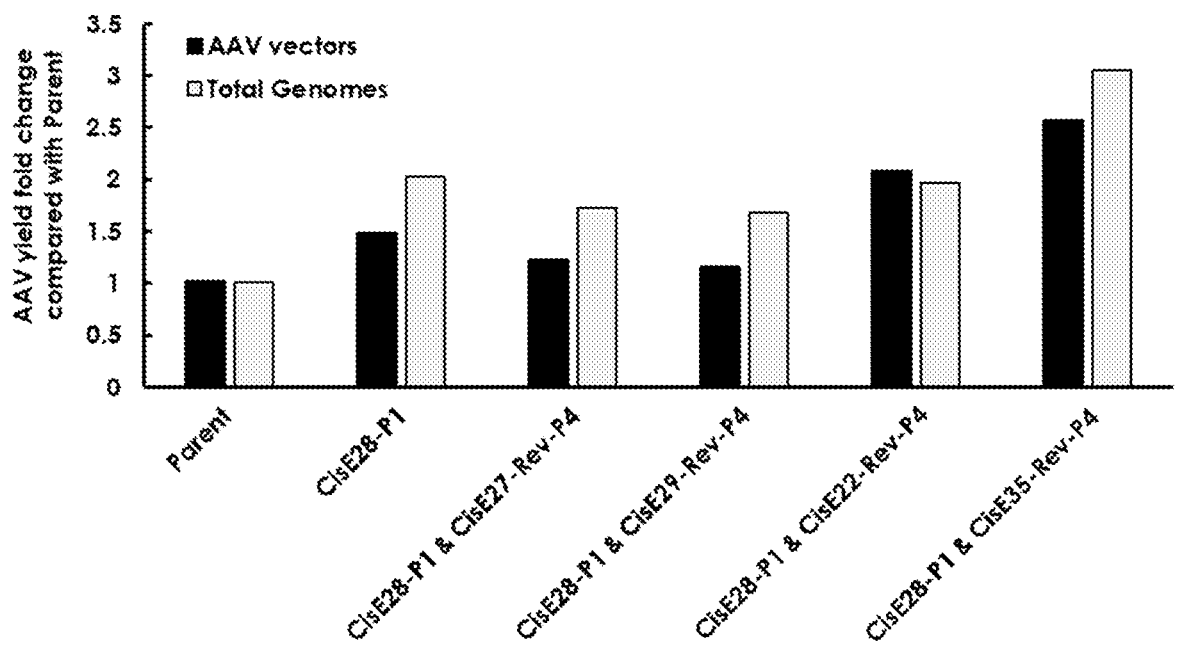

The effect on rAAV production titers of inserting different Cis-Elements within the P4 Domain of an rAAV plasmid vector, while maintaining the same Cis-Element within the P1 Domain of such rAAV plasmid vector, was investigated by introducing Cis-Element CisE28 into the P1 Domain of the rAAV plasmid vector pAV-TBG-EGFP. The plasmid vectors were then further modified to contain Cis-Element CisE22-Rev, CisE27-Rev, CisE29-Rev, or CisE35-Rev within its P4 Domain (FIG. 13D), essentially as described above. An rAAV having a Cis28 Cis-Element within its P1 Domain and a CisE35-Rev Cis-Element within its P4 Domain exhibited a 2-3 fold increased production titer relative to that of the parent rAAV.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A recombinantly-modified adeno-associated virus (rAAV) that comprises a Cis-Element in one or more of its P1, P2, P3 or P4 Domains, wherein:
   (1) said P1 Domain is 5' to a 5' ITR of said rAAV;
   (2) said P2 Domain is 3' to said 5' ITR of said rAAV and 5' to a transgene cassette of said rAAV;
   (3) said P3 Domain is 3' to said transgene cassette of said rAAV and 5' to a 3' ITR of said rAAV; and
   (4) said P4 Domain is 3' to said 3' ITR of said rAAV;
   wherein the Cis-Element comprises any of SEQ ID NOs: 45-74; and
   wherein the presence of said Cis-Element causes rAAV-producing cells to produce said rAAV at a higher production titer than would be attained with such rAAV if lacking said Cis-Element.

2. The recombinantly-modified adeno-associated virus (rAAV) of claim 1, wherein said rAAV comprises the Cis-Element in its P1 Domain.

3. The recombinantly-modified adeno-associated virus (rAAV) of claim 1, wherein said rAAV comprises the Cis-Element in its P2 Domain.

4. The recombinantly-modified adeno-associated virus (rAAV) of claim 1, wherein said rAAV comprises the Cis-Element in its P3 Domain.

5. The recombinantly-modified adeno-associated virus (rAAV) of claim 1, wherein said rAAV comprises the Cis-Element in its P4 Domain.

6. The recombinantly-modified adeno-associated virus (rAAV) of claim 1, wherein said rAAV comprises the Cis-Element in its P1 Domain and in one or more of its P2, P3 or P4 Domain.

7. The recombinantly-modified adeno-associated virus (rAAV) of claim 1, wherein said rAAV comprises the Cis-Element in its P2 Domain and in one or more of its P3 or P4 Domain.

8. The recombinantly-modified adeno-associated virus (rAAV) of claim 1, wherein said rAAV comprises the Cis-Element in its P3 Domain and its P4 Domain.

9. The recombinantly-modified adeno-associated virus (rAAV) of claim 1, wherein said transgene cassette encodes a protein, or wherein said transgene cassette comprises a transcribed nucleic acid, that is therapeutic for a genetic or heritable disease or condition.

10. The recombinantly-modified adeno-associated virus (rAAV) of claim 1, wherein said rAAV belongs to the rAAV1, rAAV2, rAAV5, rAAV6, rAAV7, rAAV8, rAAV9 or rAAV10 serotype, or to a hybrid of said serotypes.

11. A pharmaceutical composition that comprises:
(A) the recombinantly-modified adeno-associated virus (rAAV) of claim 1; and
(B) a pharmaceutically acceptable carrier.

12. The pharmaceutical composition of claim 11, wherein said rAAV belongs to the rAAV1, rAAV2, rAAV5, rAAV6, rAAV7, rAAV8, rAAV9 or rAAV10 serotype, or to a hybrid of said serotypes.

13. A method for increasing the production titer of recombinantly-modified adeno-associated virus (rAAV), wherein said method comprises:
(A) employing an rAAV that has been modified to comprise an added Cis-Element in one or more of its P1, P2, P3 or P4 Domains, wherein:
  (1) said P1 Domain is 5' to a 5' ITR of said rAAV;
  (2) said P2 Domain is 3' to said 5' ITR of said rAAV and 5' to a transgene cassette of said rAAV;
  (3) said P3 Domain is 3' to said transgene cassette of said rAAV and 5' to a 3' ITR of said rAAV; and
  (4) said P4 Domain is 3' to said 3' ITR of said rAAV;
  wherein the Cis-Element comprises any of SEQ ID NOs: 45-74; and
(B) culturing cells that have been transfected with said rAAV, wherein said cells additionally contain an AAV helper function-providing polynucleotide and a non-AAV helper function-providing polynucleotide, and wherein said culturing is conducted in a culture medium under conditions sufficient to permit the production of rAAV;
wherein the presence of said Cis-Element in said rAAV causes said cells to produce said rAAV at an increased production titer relative to that which would be attained if said rAAV had lacked said Cis-Element.

14. The method of claim 13, wherein said cells are human embryonic kidney cells or baby hamster kidney cells.

15. The method of claim 14, wherein said cells are HEK293 human embryonic kidney cells.

16. The method of claim 14, wherein said cells are BHK21 baby hamster kidney cells.

17. The method of claim 13, wherein said cells are sf9 insect cells.

* * * * *